US010344267B2

(12) United States Patent
Lewis et al.

(10) Patent No.: US 10,344,267 B2
(45) Date of Patent: Jul. 9, 2019

(54) DIRECTED EVOLUTION OF A REGIOSELECTIVE HALOGENASE FOR INCREASED THERMOSTABILITY

(71) Applicant: The University of Chicago, Chicago, IL (US)

(72) Inventors: Jared C. Lewis, Chicago, IL (US);
Catherine Poor, Chicago, IL (US);
Mary Andorfer, Chicago, IL (US);
James Payne, Chicago, IL (US)

(73) Assignee: The University of Chicago, Chicago, IL (US)

( * ) Notice: Subject to any disclaimer, the term of this patent is extended or adjusted under 35 U.S.C. 154(b) by 163 days.

(21) Appl. No.: 15/100,065

(22) PCT Filed: Nov. 26, 2014

(86) PCT No.: PCT/US2014/067661
§ 371 (c)(1),
(2) Date: May 27, 2016

(87) PCT Pub. No.: WO2015/081228
PCT Pub. Date: Jun. 4, 2015

(65) Prior Publication Data
US 2017/0002334 A1     Jan. 5, 2017

Related U.S. Application Data

(60) Provisional application No. 61/909,951, filed on Nov. 27, 2013.

(51) Int. Cl.
| | |
|---|---|
| *C12N 9/04* | (2006.01) |
| *C12N 9/02* | (2006.01) |
| *C12P 13/22* | (2006.01) |
| *C12P 17/10* | (2006.01) |
| *C12P 17/18* | (2006.01) |
| *C12P 5/00* | (2006.01) |

(52) U.S. Cl.
CPC ............ *C12N 9/0071* (2013.01); *C12P 5/005* (2013.01); *C12P 13/227* (2013.01); *C12P 17/10* (2013.01); *C12P 17/182* (2013.01); *C12Y 114/14007* (2013.01); *C12Y 114/14009* (2013.01)

(58) Field of Classification Search
CPC .................................................... C12N 9/0006
See application file for complete search history.

(56) References Cited

U.S. PATENT DOCUMENTS

| | | | |
|---|---|---|---|
| 2008/0004326 A1 | 1/2008 | Sanchez-Reillo et al. | ... 514/410 |
| 2011/0182862 A1* | 7/2011 | Green | ............. A01N 63/04 424/93.5 |

OTHER PUBLICATIONS

Tang et al., UniProt database, accession No. R4SX80, Jul. 2013.*
Adams et al. "PHENIX: a comprehensive Python-based system for macromolecular structure solution", *Acta Crystallographica*, D66: 213-221, 2010.
Anderson et al., "Molecular mechanisms of enzyme-catalysed halogenation", *Molecular Biosystems*, 2: 350-357, 2006.
Blasiak et al., "Structural Perspective on Enzymatic Halogenation", *Accounts of Chemical Research*, 42: 147-155, 2009.
Butler et al., "Mechanistic considerations of halogenating enzymes", *Nature*, 460: 848-854, 2009.
Emsley et al., "Coot: model building tools for molecular graphics", *Acta Crystallographica*, D60: 2126-2132, 2004.
Glenn et al., "Reengineering a Tryptophan Halogenase to Preferentially Chlorinate a Direct Alkaloid Precursor", *J Am Chem Soc*, 133: 19346-19349, 2011.
Heckman et al., "Gene splicing and mutagenesis by PCR-driven overlap extension", *Nature Protocols*, 2: 924-932, 2007.
McCoy et al., "Phaser crystallographic software", *Applied Crystallography*, 40: 658-674, 2007.
Otwinowski et al., "Processing of X-ray diffraction data collected in oscillation mode", *Methods in Enzymology*, 276: 307-326, 1997.
Payne et al., "Regioselective Arene Halogenation using the FAD-Dependent Halogenase RebH", *Angewandte Chemie International Edition*, 52: 5271-5274, 2013.
Petsko, "Structural basis of thermostability in hyperthermophilic proteins, or There's more than one way to skin a cat", *Methods in Enzymology*, 334: 469-478, 2001.
Vaillancourt et al., "Nature's Inventory of Halogenation Catalysts: Oxidative Strategies Predominate", *Chemical Reviews*, 106: 3364-3378, 2006.
International Search Report and Written Opinion issued in PCT/US14/67661, dated Jun. 3, 2015.

* cited by examiner

*Primary Examiner* — Maryam Monshipouri
(74) *Attorney, Agent, or Firm* — Norton Rose Fulbright US LLP

(57) ABSTRACT

Compounds and methods are providing involving RebH variants with improved properties. directed evolution based on random mutagenesis was employed to generate a series of RebH variants. RebH variants with improved thermostability and increased activity at elevated temperatures were generated.

16 Claims, 6 Drawing Sheets
Specification includes a Sequence Listing.

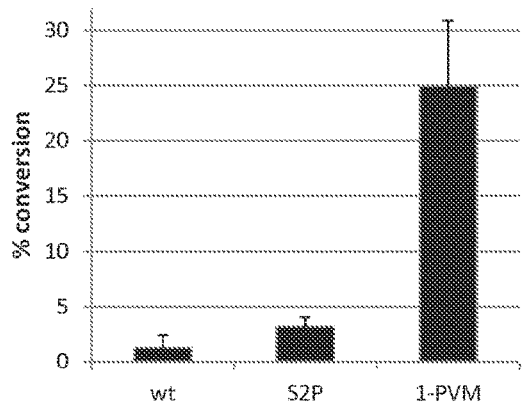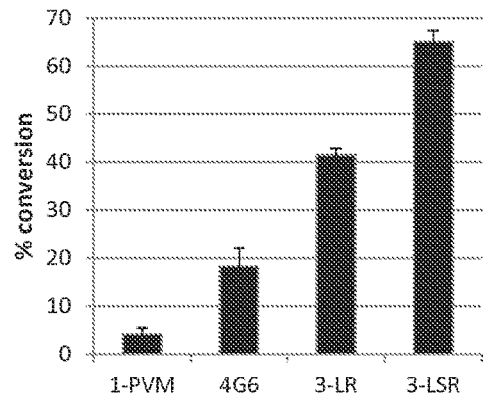
Fig. 1A    Fig. 1B
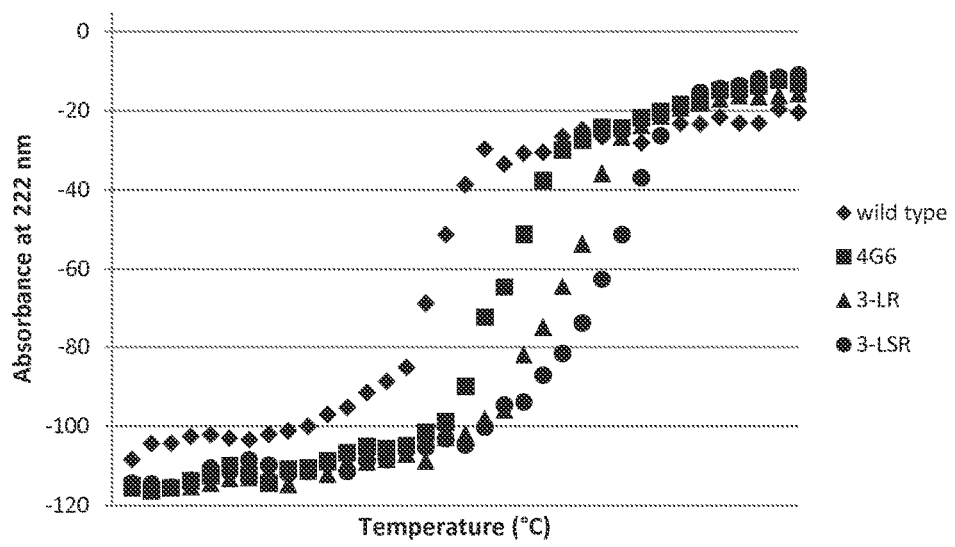
Fig. 2

| Ability of WT RebH and Variants (1 % load) to Halogenate Tryptoline (% conversion) | |
|---|---|
| wt | 2 |
| S2P M71V K145M | 4 |
| S2P M71V K145M N467T | 8 |
| S2P M71V K145M N467T N470S | 75 |
| S2P M71V K145M N467T G112S | 42 |
| S2P M71V K145M N467T G112S N470S | 100 |

Fig. 5A

| Ability of WT RebH and Variants (0.5 % load) to Halogenate Tryptoline (% conversion) | |
|---|---|
| wt | 2 |
| S2P M71V K145M E423D E461G S130L | 1 |
| S2P M71V K145M E423D E461G Q494R S130L | 2 |
| S2P M71V K145M E423D E461G Q494R S130L N166S | 2 |
| S2P M71V K145M N467T G112S N470S | 82 |
| S2P M71V K145M E423D E461G Q494R S130L N467T G112S | 3 |
| S2P M71V K145M E423D E461G Q494R S130L N467T G112S N470S | 25 |

Fig. 5B

| Ability of WT RebH and Variants (0.3 % load) to Halogenate Tryptoline (% conversion) | |
|---|---|
| S2P M71V K145M N467T G112S N470S | 51 |
| S2P M71V K145M N467T G112S N470S L114P | 28 |
| S2P M71V K145M N467T G112S N470S R400C | 43 |
| S2P M71V K145M N467T G112S N470S D203G | 57 |
| S2P M71V K145M N467T G112S N470S V225I | 59 |
| S2P M71V K145M N467T G112S N470S L426M | 46 |

Fig. 5C

| Ability of WT RebH and Variants (0.3 % load) to Halogenate Tryptoline (% conversion) | |
|---|---|
| S2P M71V K145M N467T G112S N470S | 32 |
| S2P M71V K145M N467T G112S N470S D203G | 41 |
| S2P M71V K145M N467T G112S N470S V225I | 41 |
| S2P M71V K145M N467T G112S N470S D203G V225I | 19 |

Fig. 5D

| Ability of WT RebH and Variants (1% load) to Halogenate Tryptoline (2mM substrate) (% conversion) | |
|---|---|
| S2P M71V K145M N467T G112S N470S V225I | 47 |
| S2P M71V K145M N467T G112S N470S V225I H262Y | 34 |
| S2P M71V K145M N467T G112S N470S V225I Q431R V506I | 66 |
| S2P M71V K145T N467T G112S N470S V225I Y116C L159H I361V S469G | 49 |

Fig. 5E

| Thermostability, 42 °C for 2 hours, 1% load (% conversion) | |
|---|---|
| wild type (wt) | 61 |
| S2P | 100 |
| F396Y | 87 |
| K145M | 100 |
| D203A | 91 |

Fig. 6A

| Thermostability, 42 °C for 2 hours, 1% load (% conversion) | |
|---|---|
| wt | 11 |
| M71V | 46 |
| M71T | 34 |
| M71A | 35 |
| M71C | 27 |

Fig. 6B

| Thermostability, 42 °C for 2 hours, 1% load (% conversion) | |
|---|---|
| wt | 11 |
| S2P | 59 |
| S2P, M71V | 85 |
| S2P, T213A | 56 |
| S2P, K145M | 100 |
| S2P, D203A | 63 |
| S2P, F396Y | 73 |

Fig. 6C

| Thermostability, 42 °C for 2 hours, 0.5% load (% conversion) | |
|---|---|
| wt | 5 |
| S2P | 44 |
| S2P M71V | 56 |
| S2P K145M | 82 |
| S2P M71V K145M | 95 |

Fig. 6D

| Thermostability, 51 °C for 2 hours, 0.5% load (% conversion) | |
|---|---|
| wt | 0 |
| S2P M71V K145M | 10 |
| S2P M71V K145M N467T | 3 |
| S2P M71V K145M F458S | 0 |
| S2P M71V K145M T394M | 8 |
| S2P M71V K145M E423D E461G | 16 |
| S2P M71V K145M T348A L453P A476T | 0 |
| S2P M71V K145M D264G | 3 |

Fig. 6E

| Thermostability, 49.5 °C for 2 hours, 0.5% load (% conversion) | |
|---|---|
| wt | 1 |
| S2P M71V K145M | 9 |
| S2P M71V K145M E423D E461G | 14 |
| S2P M71V K145M E423D E461G T413A Q494R | 58 |
| S2P M71V K145M E423D E461G K237E | 24 |
| S2P M71V K145M E423D E461G S130L | 85 |
| S2P M71V K145M E423D E461G T496R | 21 |
| S2P M71V K145M E423D E461G G504S | 30 |
| S2P M71V K145M E461G T258A L289P | 51 |
| S2P M71V K145M E423D E461G Q494R | 39 |
| S2P M71V K145M E423D E461G N166S | 89 |

Fig. 7A

| Thermostability, 48 °C for 2 hours, 0.5% load (% conversion) | |
|---|---|
| S2P M71V K145M E423D E461G | 13 |
| S2P M71V K145M E423D E461G Q494R | 36 |
| S2P M71V K145M E423D E461G S130L | 53 |
| S2P M71V K145M E423D E461G N166S | 38 |
| S2P M71V K145M E423D E461G Q494R S130L | 74 |
| S2P M71V K145M E423D E461G Q494R N166S | 62 |
| S2P M71V K145M E423D E461G S130L N166S | 82 |
| S2P M71V K145M E423D E461G Q494R S130L N166S | 68 |

DIRECTED EVOLUTION OF A REGIOSELECTIVE HALOGENASE FOR INCREASED THERMOSTABILITY

CROSS-REFERENCE TO RELATED APPLICATIONS

This application is a national phase application under 35 U.S.C. § 371 of International Application No. PCT/US2014/067661, filed Nov. 26, 2014, which claims priority to U.S. Provisional Application No. 61/909,951, filed on Nov. 27, 2013. The entire contents of each of the above-referenced disclosures are specifically incorporated herein by reference without disclaimer.

STATEMENT OF GOVERNMENT SUPPORT

This invention was made with government support under grant number 5R00GM087551-03 awarded by The National Institutes of Health. The government has certain rights in the invention.

FIELD OF THE INVENTION

This invention relates generally to the fields of molecular biology, biochemistry, organic chemistry and optical biophysics. More particularly, it concerns the generation of RebH mutants and analysis thereof for the halogenation of organic compounds and thermal stability.

DESCRIPTION OF RELATED ART

Halogenated organic compounds are extensively employed as building blocks, synthetic intermediates, and end use products for industrial, materials, agrochemical, and pharmaceutical applications due to their unique reactivity and physical properties. A multitude of methods for the halogenation of alkyl and alkenyl compounds have been described. These include Kharasch metal-catalyzed free radical addition of $CXCl_3$ compounds to alkenes, epoxide ring-opening by halide nucleophiles, Appel conversion of an alcohol to a halogen, the Hunsdiecker reaction to convert a carboxylic acid to a chain-shortened halide, Hell-Volhard-Zelinsky halogenation to alpha-halogenate carboxylic acids, and direct halogen addition to alkenes, among others.

Halogenated arenes comprise a particularly important class of compounds. To date, more than 3,800 halogenated natural products have been identified, several of which include halogenated arene functional groups. The therapeutic natural products Vancomycin, an important antibiotic isolated from soil fungi, Griseofulvin, an orally administered antifungal agent, chlorotetracycline, an antibiotic, and Maytansine, a potent antitumor agent include at least one halogenated arene in their structures.

Conventional approaches to arene halogenation via electrophilic aromatic substitution require harsh chemical oxidants and often suffer from poor regioselectivity. The two primary procedures for the direct halogenation of arenes proceed through relatively harsh conditions. The Sandmeyer reaction employs nitrous acid to convert an aniline to an aryl halide through a diazonium salt intermediate. Friedel-Crafts halogenation employs a metal halide, e.g. $FeCl_3$ or $AlCl_3$, to effect the halogenation of an arene. The relatively harsh conditions of the Sandmeyer and Friedel Crafts aromatic halogenation reactions are incompatible with certain functional groups. Despite the multitude of organic chemical transformations available for the halogenation of alkyl and alkenyl compounds, a method for the halogenation of arenes under mild conditions has yet to be identified.

SUMMARY

Embodiments provided herein are based on the development and characterization of RebH mutants that halogenate aromatic compounds. In a first embodiment, methods and compositions are provided for the biosynthetic halogenation of arenes. In a further embodiment, compositions comprising mutated variants of RebH demonstrate improved arene-halogenating activity. In some embodiments mutated variants of RebH exhibit increased thermal stability over wild-type RebH.

In some embodiments, there are mutated variants of the halogenase RebH. In some embodiments, the mutated variants of RebH are isolated polypeptides. In specific embodiments, a RebH variant comprises one or more amino acid substitutions selected from the group consisting of S2P; I52T; A58V; M71V, M71T, M71A, or M71C; N75K; E96V; D101G; S110P; S110L; F111L; F111S; G112S; G112D; L113D; L113N; L114P; S130L; K145M; K145R; N166S; F171I; K187R; D203A or D203G; T213A; V225I; K237E; V256I; T258A; D264G; T283A; L289P; F312L; T322I; T348A; L380F; T394M; F396L; F396Y; R400C; T413A; E423D; A442V; S448P; L453P; Y455W; F458S; F458L; E461G; F465L; F465C; N467T; N470S; A476T; A476V; V481A; Q494R; T496R; T496A; G504S; and R509Q. In particular embodiments, a RebH variant comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 of such amino acid substitutions (and any range derivable therein). SEQ ID NO:1 is the amino acid sequence of a RebH polypeptide. SEQ ID NO:2 is the underlying nucleic acid sequence for the RebH polypeptide.

In some embodiments, a RebH variant polypeptide of SEQ ID NO: 1 comprises at least one amino acid substitution, wherein the at least one amino acid substitution results in improved halogenating activity. In particular embodiments, a RebH variant polypeptide is an isolated RebH variant polypeptide. In some embodiments, a RebH mutant undergoes one or more subsequent rounds of optimization. Subsequent optimization may impart a primary mutation, i.e., a mutation of a wild type amino acid and/or a secondary mutation, i.e., a mutation of a previously mutated amino acid. The relative importance of the mutation is not reflected by the use of the term "secondary." Rather, "secondary" refers to the mutation process where a wild type amino acid is mutated in a first mutating round, then is further mutated to a secondary, different amino acid in a subsequent optimization process. For example, a RebH variant comprising a S110P mutation may be further mutated to comprise the secondary mutation P110L. The effective mutation from WT RebH is S110L. In some embodiments, secondary mutations include P110L and L111S. Subsequent optimization of a RebH mutant may impart secondary, or higher order mutations, for example, tertiary and quaternary mutations. It is specifically contemplated that substitutions need not be created in a step-wise fashion but in some embodiments the method of creating them involves serial substitutions at the same position.

In particular embodiments, a RebH variant polypeptide comprises one or more of the following substitutions as compared to SEQ ID NO:1: S2P, I52T, A58V, M71V, M71T, M71A, M71C, N75K, E96V, D101G, S110P, S110L, F111L, F111S, G112S, G112D, L113D, L113N, L114P, S130L, K145M, K145R, N166S, F171I, K187R, D203A or D203G, T213A, V225I, K237E, V256I, T258A, D264G, T283A, L289P, F312L, T322I, T348A, L380F, T394M, F396Y, F396L, R400C, T413A, E423D, A442V, S448P, L453P, Y455W, F458S, F458L, E461G, F465C, F465L, N467T, N470S, A476T, A476V, V481A, Q494R, T496R, T496A, G504S, and R509Q. In particular embodiments, a RebH variant comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 of such amino acid substitutions (and any range derivable therein). It is specifically contemplated that variations may be made in RebH polypeptides whose sequence differs from SEQ ID NO:1. A RebH polypeptide whose sequence differs from SEQ ID NO:1, for example, a polypeptide sequence that is less than 100% identical but at least 60% identical, may have any of the following amino acids substituted or combinations of amino acids substituted: the serine corresponding to S2 in SEQ ID NO:1; the methionine corresponding to M71 in SEQ ID NO:1; the asparagine corresponding to N75 in SEQ ID NO:1; the glutamic acid corresponding to E96 in SEQ ID NO:1; the aspartic acid corresponding to D101 in SEQ ID NO:1; the glycine corresponding to G112 in SEQ ID NO:1; the leucine corresponding to L114 in SEQ ID NO:1; the serine corresponding to S130 in SEQ ID NO:1; the lysine corresponding to K145 in SEQ ID NO:1; the asparagine corresponding to N166 in SEQ ID NO:1; the phenylalanine corresponding to F171 in SEQ ID NO:1; the aspartic acid corresponding to D203 in SEQ ID NO:1; the threonine corresponding to T213 in SEQ ID NO:1; the valine corresponding to V225 in SEQ ID NO:1; the lysine corresponding to K237 in SEQ ID NO:1; the valine corresponding to V256 in SEQ ID NO:1; the threonine corresponding to T258 in SEQ ID NO:1; the aspartic acid corresponding to D264 in SEQ ID NO:1; the threonine corresponding to T283 in SEQ ID NO:1; the leucine corresponding to L289 in SEQ ID NO:1; the phenylalanine corresponding to F312 in SEQ ID NO:1; the threonine corresponding to T348 in SEQ ID NO:1; the leucine corresponding to L380 in SEQ ID NO:1; the threonine corresponding to T394 in SEQ ID NO:1; the phenylalanine corresponding to F396 in SEQ ID NO:1; the arginine corresponding to R400 in SEQ ID NO:1; the threonine corresponding to T413 in SEQ ID NO:1; the glutamic acid corresponding to E423 in SEQ ID NO:1; the leucine corresponding to L453 in SEQ ID NO:1; the phenylalanine corresponding to F458 in SEQ ID NO:1; the glutamic acid corresponding to E461 in SEQ ID NO:1; the phenylalanine corresponding to F465 in SEQ ID NO:1; the asparagine corresponding to N467 in SEQ ID NO:1; the asparagine corresponding to N470 in SEQ ID NO:1; the alanine corresponding to A476 in SEQ ID NO:1; the glutamine corresponding to Q494 in SEQ ID NO:1; the threonine corresponding to T496 in SEQ ID NO:1; and/or, the glycine corresponding to G504 in SEQ ID NO:1. These substitutions may be with any amino acid or the amino acid indicated for that position in the following list: S2P, I52T, A58V, M71V, M71T, M71A, M71C, N75K, E96V, D101G, S110P, S110L, F111L, F111S, G112S, G112D, L113D, L113N, L114P, S130L, K145M, K145R, N166S, F171I, K187R, D203A or D203G, T213A, V225I, K237E, V256I, T258A, D264G, T283A, L289P, F312L, T322I, T348A, L380F, T394M, F396Y, F396L, R400C, T413A, E423D, A442V, S448P, L453P, Y455W, F458S, F458L, E461G, F465C, F465L, N467T, N470S, A476T, A476V, V481A, Q494R, T496R, T496A, G504S, and R509Q. In a particular embodiment, a RebH variant comprises the amino acid substitutions S2P, M71V, K145M, N467T, N470S, and G112S.

In some embodiments, a RebH variant has 1, 2, 3, 4, 5, 6, 7, 8, 9, 10 or more serine substitutions (and any range derivable therein), which may or may not be at positions 1 and/or 130 in SEQ ID NO:1. In some embodiments, a RebH variant has 1, 2, 3, 4, 5, 6, 7, 8, 9, 10 or more methionine substitutions, which may or may not be at position 71 in SEQ ID NO:1. In some embodiments, a RebH variant has 1, 2, 3, 4, 5, 6, 7, 8, 9, 10 or more glutamic acid substitutions (and any range derivable therein), which may or may not be at positions 96, 423, and/or 461 in SEQ ID NO:1. In some embodiments, a RebH variant has 1, 2, 3, 4, 5, 6, 7, 8, 9, 10 or more aspartic acid substitutions (and any range derivable therein), which may or may not be at positions 101, 203, and/or 264 in SEQ ID NO:1. In some embodiments, a RebH variant has 1, 2, 3, 4, 5, 6, 7, 8, 9, 10 or more glycine substitutions (and any range derivable therein), which may or may not be at positions 112 and/or 504 in SEQ ID NO:1. In some embodiments, a RebH variant has 1, 2, 3, 4, 5, 6, 7, 8, 9, 10 or more lysine substitutions (and any range derivable therein), which may or may not be at positions 145 and/or 237 in SEQ ID NO:1. In some embodiments, a RebH variant has 1, 2, 3, 4, 5, 6, 7, 8, 9, 10 or more asparagine substitutions (and any range derivable therein), which may or may not be at positions 166, 467, and/or 470 in SEQ ID NO:1. In some embodiments, a RebH variant has 1, 2, 3, 4, 5, 6, 7, 8, 9, 10 or more phenylalanine substitutions (and any range derivable therein), which may or may not be at positions 171, 312, 396, 458, and/or 465 in SEQ ID NO:1. In some embodiments, a RebH variant has 1, 2, 3, 4, 5, 6, 7, 8, 9, 10 or more threonine substitutions (and any range derivable therein), which may or may not be at positions 213, 258, 283, 348, 394, 413, and/or 496 in SEQ ID NO:1. In some embodiments, a RebH variant has 1, 2, 3, 4, 5, 6, 7, 8, 9, 10 or more valine substitution (and any range derivable therein), which may or may not be at positions 225 and/or 256 in SEQ ID NO:1. In some embodiments, a RebH variant has 1, 2, 3, 4, 5, 6, 7, 8, 9, 10 or more leucine substitutions (and any range derivable therein), which may or may not be at positions 289, 380, and/or 453 in SEQ ID NO:1. In some embodiments, a RebH variant has 1, 2, 3, 4, 5, 6, 7, 8, 9, 10 or more arginine substitutions (and any range derivable therein), which may or may not be at position 400 in SEQ ID NO:1. In some embodiments, a RebH variant has 1, 2, 3, 4, 5, 6, 7, 8, 9, 10 or more alanine substitutions, which may or may not be at position 476 in SEQ ID NO:1. In some embodiments, a RebH variant has 1, 2, 3, 4, 5, 6, 7, 8, 9, 10 or more glutamine substitutions (and any range derivable therein), which may or may not be at position 494 in SEQ ID NO:1.

In some embodiments, a RebH variant polypeptide comprises at least one amino acid substitution at position 2, 52, 58, 71, 75, 96, 101, 110, 111, 112, 113, 114, 130, 145, 166, 171, 187, 203, 213, 225, 237, 256, 258, 264, 283, 289, 312, 322, 348, 380, 394, 396, 400, 413, 423, 442, 448, 453, 455, 458, 461, 465, 467, 470, 476, 481, 494, 496, 504 and/or 509 in SEQ ID NO:1. In further embodiments, a RebH variant polypeptide comprises at least 3 amino acid substitutions at positions 2, 52, 58, 71, 75, 96, 101, 110, 111, 112, 113, 114, 130, 145, 166, 171, 187, 203, 213, 225, 237, 256, 258, 264, 283, 289, 312, 322, 348, 380, 394, 396, 400, 413, 423, 442, 448, 453, 455, 458, 461, 465, 467, 470, 476, 481, 494, 496, 504 and/or 509 in SEQ ID NO: 1. In other embodiments, a RebH variant polypeptide comprises at least 5 amino acid substitutions at positions 2, 52, 58, 71, 75, 96, 101, 110, 111, 112, 113, 114, 130, 145, 166, 171, 187, 203, 213, 225, 237, 256, 258, 264, 283, 289, 312, 322, 348, 380, 394, 396, 400, 413, 423, 442, 448, 453, 455, 458, 461, 465, 467, 470, 476, 481, 494, 496, 504 and/or 509 in SEQ ID NO: 1. In particular embodiments, a RebH variant comprises or comprises at least or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 amino acid substitutions (and any range derivable therein) at position 2, 71, 75, 96, 101, 112, 114, 130, 145, 166, 171, 203, 213, 225, 237, 256, 258, 264, 283, 289, 312, 348, 380, 394, 396, 400, 413, 423, 453, 458, 461, 465, 467, 470, 476, 494, 496, and/or 504 in SEQ ID NO: 1.

In additional embodiments, a RebH variant polypeptide comprises at least one amino acid substitution at position 2, 52, 58, 71, 75, 96, 101, 110, 111, 112, 113, 114, 130, 145, 166, 171, 187, 203, 213, 225, 237, 256, 258, 264, 283, 289, 312, 322, 348, 380, 394, 396, 400, 413, 423, 442, 448, 453, 455, 458, 461, 465, 467, 470, 476, 481, 494, 496, 504 and/or 509 in SEQ ID NO:1, wherein the RebH variant polypeptide is at least 60% identical to SEQ ID NO:1. In additional embodiments, a RebH variant polypeptide comprises at least or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 amino acid substitution(s) at position 2, 52, 58, 71, 75, 96, 101, 110, 111, 112, 113, 114, 130, 145, 166, 171, 187, 203, 213, 225, 237, 256, 258, 264, 283, 289, 312, 322, 348, 380, 394, 396, 400, 413, 423, 442, 448, 453, 455, 458, 461, 465, 467, 470, 476, 481, 494, 496, 504 and/or 509 in SEQ ID NO:1, wherein the RebH variant polypeptide is at least or at most 60%, 65%, 70%, 75%, 80%, 85%, 90%, 95%, 98%, 99% or 100% identical to SEQ ID NO:1 (or any range derivable therein). It is specifically contemplated that there may be substitutions at other positions in SEQ ID NO:1. Additionally, a version of RebH may be used such that it is missing at most or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100 or more total or contiguous amino acids (or any range derivable therein) from SEQ ID NO:1.

In some embodiments, a RebH variant polypeptide can halogenate aromatic substrates. In some embodiments, a RebF reductase is employed with a RebH variant polypeptide. In particular embodiments, a RebH variant polypeptide regioselectively halogenates aromatic substrates. In further embodiments, a RebH variant polypeptide halogenates aromatic substrates to create novel compounds. In further embodiments, a RebH variant polypeptide halogenates aromatic substrates in the presence of functional groups not amenable to existing aromatic chlorination methods. In particular embodiments, a RebH polypeptide variant is used to append halogen isotopes to organic compounds. In further embodiments, a RebH polypeptide variant is used to isotopically label organic compounds. In some embodiments, a RebH variant polypeptide displays improved thermostability over wild-type RebH. In other embodiments, a RebH variant polypeptide displays increased halogenating activity at an elevated temperature. In some embodiments, a RebH variant polypeptide's increased halogenating activity includes higher product conversion and/or increased reaction kinetics over wild-type RebH. In yet other embodiments, a RebH variant polypeptide displays improved catalytic efficiency over wild-type RebH. In further embodiments, a RebH variant polypeptide halogenates with higher substrate conversion than existing aromatic chlorination methods.

In some embodiments, a RebH variant polypeptide halogenates aryl compounds. In particular embodiments, a RebH variant polypeptide halogenates the wild-type RebH native substrate tryptophan. In other embodiments, a RebH variant polypeptide halogenates non-native substrates. In yet other embodiments, a RebH variant polypeptide halogenates indole, tryptoline, and 2-methyltryptamine. In particular embodiments, a RebH variant polypeptide halogenates using a halide selected from the group consisting of fluoride, chloride, bromide and iodide. In some embodiments, halogenating conditions comprise a mixture of HEPES, lysate, NaCl, NAD, FAD, glucose, RebF, glucose dehydrogenase and RebH or a RebH variant polypeptide.

In some embodiments, a RebH variant polypeptide displays prolonged catalyst lifetime over wild-type RebH. In some embodiments, a RebH variant polypeptide displays increased tolerance to proteolysis over wild-type RebH. In other embodiments, a RebH variant polypeptide displays increased tolerance to organic solvents over wild-type RebH. In some embodiments, the halogenation reaction proceeds in the absence of a harsh chemical oxidant, for example aluminum chloride, iron (III) chloride or nitrous acid.

In any of the embodiments involving RebH variants, it is contemplated that a RebH variant is one that has less than 100% amino acid identity to SEQ ID NO:1. In different embodiments, and in the context of any other RebH embodiment discussed herein, the RebH variant has, has at least, or has at most 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, or 99.8 percent identity (or any range derivable therein) to SEQ ID NO:1. Additionally or alternatively, RebH variants may have or have at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, or 510 contiguous amino acids (and any range derivable therein) from SEQ ID NO:1. In certain embodiments, there are or are at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 different regions of contiguous amino acids (and any range derivable therein) in a RebH variant that have, have at most, or have at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 contiguous amino acids from SEQ ID NO:1 (and any range derivable therein).

In some embodiments, a process for halogenating an aromatic substrate comprises employing a RebH variant polypeptide. In other embodiments, a process for halogenating an aromatic substrate comprises mixing an isolated RebH variant polypeptide with the aromatic substrate and at least one halide source under halogenating conditions. In some embodiments, a RebH variant polypeptide displays at least 98% sequence homology to SEQ ID NO: 1.

In some embodiments, a RebH variant polypeptide is used in a method to produce a library of halogenated aromatic compounds. In other embodiments, a method for producing a library of halogenated aromatic compounds comprises reacting a plurality of different aromatic compounds with an isolated RebH variant polypeptide and at least one halide source under halogenating conditions. In particular embodiments, the isolated RebH variant polypeptide has at least 98% sequence homology to SEQ ID NO: 1. In some embodiments, the isolated RebH variant polypeptide comprises at least one amino acid substitution at position 2, 52, 58, 71, 75, 96, 101, 110, 111, 112, 113, 114, 130, 145, 166, 171, 187, 203, 213, 225, 237, 256, 258, 264, 283, 289, 312, 322, 348, 380, 394, 396, 400, 413, 423, 442, 448, 453, 455, 458, 461, 465, 467, 470, 476, 481, 494, 496, 504 and/or 509 in SEQ ID NO:1.

In some embodiments, the RebH variant comprises any combination of substitutions of one or more amino acids in SEQ ID NO. 1, selected from the group consisting of: S2P, I52T, A58V, M71V, M71T, M71A, M71C, N75K, E96V, D101G, S110P, S110L, F111L, F111S, G112S, G112D, L113D, L113N, L114P, S130L, K145M, K145R, N166S, F171I, K187R, D203A or D203G, T213A, V225I, K237E, V256I, T258A, D264G, T283A, L289P, F312L, T322I, T348A, L380F, T394M, F396Y, F396L, R400C, T413A, E423D, A442V, S448P, L453P, Y455W, F458S, F458L, E461G, F465C, F465L, N467T, N470S, A476T, A476V, V481A, Q494R, T496R, T496A, G504S, and R509Q.

In some embodiments, the RebH variant comprises a combination of substitutions in SEQ ID NO: 1 selected from the following combinations of substitutions (separated by a semicolon): S2P, M71V; S2P, M71T; S2P, M71A; S2P, M71C; S2P, N75K; S2P, E96V; S2P, D101G; S2P, G112S; S2P, L114P; S2P, S130L; S2P, K145M; S2P, N166S; S2P, F171I; S2P, D203A; S2P, D203G; S2P, T213A; S2P, V225I; S2P, K237E; S2P, V256I; S2P, T258A; S2P, D264G; S2P, T283A; S2P, L289P; S2P, F312L; S2P, T348A; S2P, L380F; S2P, T394M; S2P, F396Y; S2P, R400C; S2P, T413A; S2P, E423D; S2P, L453P; S2P, F458S; S2P, E461G; S2P, F465C; S2P, N467T; S2P, N470S; S2P, A476T; S2P, Q494R; S2P, T496R; S2P, G504S; M71V, N75K; M71V, E96V; M71V, D101G; M71V, G112S; M71V, L114P; M71V, S130L; M71V, K145M; M71V, N166S; M71V, F171I; M71V, D203A; M71V, D203G; M71V, T213A; M71V, V225I; M71V, K237E; M71V, V256I; M71V, T258A; M71V, D264G; M71V, T283A; M71V, L289P; M71V, F312L; M71V, T348A; M71V, L380F; M71V, T394M; M71V, F396Y; M71V, R400C; M71V, T413A; M71V, E423D; M71V, L453P; M71V, F458S; M71V, E461G; M71V, F465C; M71V, N467T; M71V, N470S; M71V, A476T; M71V, Q494R; M71V, T496R; M71V, G504S; M71T, N75K; M71T, E96V; M71T, D101G; M71T, G112S; M71T, L114P; M71T, S130L; M71T, K145M; M71T, N166S; M71T, F171I; M71T, D203A; M71T, D203G; M71T, T213A; M71T, V225I; M71T, K237E; M71T, V256I; M71T, T258A; M71T, D264G; M71T, T283A; M71T, L289P; M71T, F312L; M71T, T348A; M71T, L380F; M71T, T394M; M71T, F396Y; M71T, R400C; M71T, T413A; M71T, E423D; M71T, L453P; M71T, F458S; M71T, E461G; M71T, F465C; M71T, N467T; M71T, N470S; M71T, A476T; M71T, Q494R; M71T, T496R; M71T, G504S; M71A, N75K; M71A, E96V; M71A, D101G; M71A, G112S; M71A, L114P; M71A, S130L; M71A, K145M; M71A, N166S; M71A, F171I; M71A, D203A; M71A, D203G; M71A, T213A; M71A, V225I; M71A, K237E; M71A, V256I; M71A, T258A; M71A, D264G; M71A, T283A; M71A, L289P; M71A, F312L; M71A, T348A; M71A, L380F; M71A, T394M; M71A, F396Y; M71A, R400C; M71A, T413A; M71A, E423D; M71A, L453P; M71A, F458S; M71A, E461G; M71A, F465C; M71A, N467T; M71A, N470S; M71A, A476T; M71A, Q494R; M71A, T496R; M71A, G504S; M71C, N75K; M71C, E96V; M71C, D101G; M71C, G112S; M71C, L114P; M71C, S130L; M71C, K145M; M71C, N166S; M71C, F171I; M71C, D203A; M71C, D203G; M71C, T213A; M71C, V225I; M71C, K237E; M71C, V256I; M71C, T258A; M71C, D264G; M71C, T283A; M71C, L289P; M71C, F312L; M71C, T348A; M71C, L380F; M71C, T394M; M71C, F396Y; M71C, R400C; M71C, T413A; M71C, E423D; M71C, L453P; M71C, F458S; M71C, E461G; M71C, F465C; M71C, N467T; M71C, N470S; M71C, A476T; M71C, Q494R; M71C, T496R; M71C, G504S; N75K, E96V; N75K, D101G; N75K, G112S; N75K, L114P; N75K, S130L; N75K, K145M; N75K, N166S; N75K, F171I; N75K, D203A; N75K, D203G; N75K, T213A; N75K, V225I; N75K, K237E; N75K, V256I; N75K, T258A; N75K, D264G; N75K, T283A; N75K, L289P; N75K, F312L; N75K, T348A; N75K, L380F; N75K, T394M; N75K, F396Y; N75K, R400C; N75K, T413A; N75K, E423D; N75K, L453P; N75K, F458S; N75K, E461G; N75K, F465C; N75K, N467T; N75K, N470S; N75K, A476T; N75K, Q494R; N75K, T496R; N75K, G504S; E96V, D101G; E96V, G112S; E96V, L114P; E96V, S130L; E96V, K145M; E96V, N166S; E96V, F171I; E96V, D203A; E96V, D203G; E96V, T213A; E96V, V225I; E96V, K237E; E96V, V256I; E96V, T258A; E96V, D264G; E96V, T283A; E96V, L289P; E96V, F312L; E96V, T348A; E96V, L380F; E96V, T394M; E96V, F396Y; E96V, R400C; E96V, T413A; E96V, E423D; E96V, L453P; E96V, F458S; E96V, E461G; E96V, F465C; E96V, N467T; E96V, N470S; E96V, A476T; E96V, Q494R; E96V, T496R; E96V, G504S; D101G, G112S; D101G, L114P; D101G, S130L; D101G, K145M; D101G, N166S; D101G, F171I; D101G, D203A; D101G, D203G; D101G, T213A; D101G, V225I; D101G, K237E; D101G, V256I; D101G, T258A; D101G, D264G; D101G, T283A; D101G, L289P; D101G, F312L; D101G, T348A; D101G, L380F; D101G, T394M; D101G, F396Y; D101G, R400C; D101G, T413A; D101G, E423D; D101G, L453P; D101G, F458S; D101G, E461G; D101G, F465C; D101G, N467T; D101G, N470S; D101G, A476T; D101G, Q494R; D101G, T496R; D101G, G504S; G112S, L114P; G112S, S130L; G112S, K145M; G112S, N166S; G112S, F171I; G112S, D203A; G112S, D203G; G112S, T213A; G112S, V225I; G112S, K237E; G112S, V256I; G112S, T258A; G112S, D264G; G112S, T283A; G112S, L289P; G112S, F312L; G112S, T348A; G112S, L380F; G112S, T394M; G112S, F396Y; G112S, R400C; G112S, T413A; G112S, E423D; G112S, L453P; G112S, F458S; G112S, E461G; G112S, F465C; G112S, N467T; G112S, N470S; G112S, A476T; G112S, Q494R; G112S, T496R; G112S, G504S; L114P, S130L; L114P, K145M; L114P, N166S; L114P, F171I; L114P, D203A; L114P, D203G; L114P, T213A; L114P, V225I; L114P, K237E; L114P, V256I; L114P, T258A; L114P, D264G; L114P, T283A; L114P, L289P; L114P, F312L; L114P, T348A; L114P, L380F; L114P, T394M; L114P, F396Y; L114P, R400C; L114P, T413A; L114P, E423D; L114P, L453P; L114P, F458S; L114P, E461G; L114P, F465C; L114P, N467T; L114P, N470S; L114P, A476T; L114P, Q494R; L114P, T496R; L114P, G504S; S130L, K145M; S130L, N166S; S130L, F171I; S130L, D203A; S130L, D203G; S130L, T213A; S130L, V225I; S130L, K237E; S130L, V256I; S130L, T258A; S130L, D264G; S130L, T283A; S130L, L289P; S130L, F312L; S130L, T348A; S130L, L380F; S130L, T394M; S130L, F396Y; S130L, R400C; S130L, T413A; S130L, E423D; S130L, L453P;

S130L, F458S; S130L, E461G; S130L, F465C; S130L, N467T; S130L, N470S; S130L, A476T; S130L, Q494R; S130L, T496R; S130L, G504S; K145M, N166S; K145M, F171I; K145M, D203G; K145M, T213A; K145M, V225I; K145M, K237E; K145M, V256I; K145M, T258A; K145M, D264G; K145M, T283A; K145M, L289P; K145M, F312L; K145M, T348A; K145M, L380F; K145M, T394M; K145M, F396Y; K145M, R400C; K145M, T413A; K145M, E423D; K145M, L453P; K145M, F458S; K145M, E461G; K145M, F465C; K145M, N467T; K145M, N470S; K145M, A476T; K145M, Q494R; K145M, T496R; K145M, G504S; N166S, F171I; N166S, D203A; N166S, D203G; N166S, T213A; N166S, V225I; N166S, K237E; N166S, V256I; N166S, T258A; N166S, D264G; N166S, T283A; N166S, L289P; N166S, F312L; N166S, T348A; N166S, L380F; N166S, T394M; N166S, F396Y; N166S, R400C; N166S, T413A; N166S, E423D; N166S, L453P; N166S, F458S; N166S, E461G; N166S, F465C; N166S, N467T; N166S, N470S; N166S, A476T; N166S, Q494R; N166S, T496R; N166S, G504S; F171I, D203A; F171I, D203G; F171I, T213A; F171I, V225I; F171I, K237E; F171I, V256I; F171I, T258A; F171I, D264G; F171I, T283A; F171I, L289P; F171I, F312L; F171I, T348A; F171I, L380F; F171I, T394M; F171I, F396Y; F171I, R400C; F171I, T413A; F171I, E423D; F171I, L453P; F171I, F458S; F171I, E461G; F171I, F465C; F171I, N467T; F171I, N470S; F171I, A476T; F171I, Q494R; F171I, T496R; F171I, G504S; D203A, T213A; D203A, V225I; D203A, K237E; D203A, V256I; D203A, T258A; D203A, D264G; D203A, T283A; D203A, L289P; D203A, F312L; D203A, T348A; D203A, L380F; D203A, T394M; D203A, F396Y; D203A, R400C; D203A, T413A; D203A, E423D; D203A, L453P; D203A, F458S; D203A, E461G; D203A, F465C; D203A, N467T; D203A, N470S; D203A, A476T; D203A, Q494R; D203A, T496R; D203A, G504S; D203G, T213A; D203G, V225I; D203G, K237E; D203G, V256I; D203G, T258A; D203G, D264G; D203G, T283A; D203G, L289P; D203G, F312L; D203G, T348A; D203G, L380F; D203G, T394M; D203G, F396Y; D203G, R400C; D203G, T413A; D203G, E423D; D203G, L453P; D203G, F458S; D203G, E461G; D203G, F465C; D203G, N467T; D203G, N470S; D203G, A476T; D203G, Q494R; D203G, T496R; D203G, G504S; T213A, V225I; T213A, K237E; T213A, V256I; T213A, T258A; T213A, D264G; T213A, T283A; T213A, L289P; T213A, F312L; T213A, T348A; T213A, L380F; T213A, T394M; T213A, F396Y; T213A, R400C; T213A, T413A; T213A, E423D; T213A, L453P; T213A, F458S; T213A, E461G; T213A, F465C; T213A, N467T; T213A, N470S; T213A, A476T; T213A, Q494R; T213A, T496R; T213A, G504S; V225I, K237E; V225I, V256I; V225I, T258A; V225I, D264G; V225I, T283A; V225I, L289P; V225I, F312L; V225I, T348A; V225I, L380F; V225I, T394M; V225I, F396Y; V225I, R400C; V225I, T413A; V225I, E423D; V225I, L453P; V225I, F458S; V225I, E461G; V225I, F465C; V225I, N467T; V225I, N470S; V225I, A476T; V225I, Q494R; V225I, T496R; V225I, G504S; K237E, V256I; K237E, T258A; K237E, D264G; K237E, T283A; K237E, L289P; K237E, F312L; K237E, T348A; K237E, L380F; K237E, T394M; K237E, F396Y; K237E, R400C; K237E, T413A; K237E, E423D; K237E, L453P; K237E, F458S; K237E, E461G; K237E, F465C; K237E, N467T; K237E, N470S; K237E, A476T; K237E, Q494R; K237E, T496R; K237E, G504S; V256I, T258A; V256I, D264G; V256I, T283A; V256I, L289P; V256I, F312L; V256I, T348A; V256I, L380F; V256I, T394M; V256I, F396Y; V256I, R400C; V256I, T413A; V256I, E423D; V256I, L453P; V256I, F458S; V256I, E461G; V256I, F465C; V256I, N467T; V256I, N470S; V256I, A476T; V256I, Q494R; V256I, T496R; V256I, G504S; T258A, D264G; T258A, T283A; T258A, L289P; T258A, F312L; T258A, T348A; T258A, L380F; T258A, T394M; T258A, F396Y; T258A, R400C; T258A, T413A; T258A, E423D; T258A, L453P; T258A, F458S; T258A, E461G; T258A, F465C; T258A, N467T; T258A, N470S; T258A, A476T; T258A, Q494R; T258A, T496R; T258A, G504S; T283A, D264G; D264G, L289P; D264G, F312L; D264G, T348A; D264G, L380F; D264G, T394M; D264G, F396Y; D264G, R400C; D264G, T413A; D264G, E423D; D264G, L453P; D264G, F458S; D264G, E461G; D264G, F465C; D264G, N467T; D264G, N470S; D264G, A476T; D264G, Q494R; D264G, T496R; D264G, G504S; T283A, L289P; T283A, F312L; T283A, T348A; T283A, L380F; T283A, T394M; T283A, F396Y; T283A, R400C; T283A, T413A; T283A, E423D; T283A, L453P; T283A, F458S; T283A, E461G; T283A, F465C; T283A, N467T; T283A, N470S; T283A, A476T; T283A, Q494R; T283A, T496R; T283A, G504S; L289P, F312L; L289P, T348A; L289P, L380F; L289P, T394M; L289P, F396Y; L289P, R400C; L289P, T413A; L289P, E423D; L289P, L453P; L289P, F458S; L289P, E461G; L289P, F465C; L289P, N467T; L289P, N470S; L289P, A476T; L289P, Q494R; L289P, T496R; L289P, G504S; F312L, T348A; F312L, L380F; F312L, T394M; F312L, F396Y; F312L, R400C; F312L, T413A; F312L, E423D; F312L, L453P; F312L, F458S; F312L, E461G; F312L, F465C; F312L, N467T; F312L, N470S; F312L, A476T; F312L, Q494R; F312L, T496R; F312L, G504S; T348A, L380F; T348A, T394M; T348A, F396Y; T348A, R400C; T348A, T413A; T348A, E423D; T348A, L453P; T348A, 458S; T348A, E461G; T348A, F465C; T348A, N467T; T348A, N470S; T348A, A476T; T348A, Q494R; T348A, T496R; T348A, G504S; L380F, T394M; L380F, F396Y; L380F, R400C; L380F, T413A; L380F, E423D; L380F, L453P; L380F, F458S; L380F, E461G; L380F, F465C; L380F, N467T; L380F, N470S; L380F, A476T; L380F, Q494R; L380F, T496R; L380F, G504S; T394M, F396Y; T394M, R400C; T394M, T413A; T394M, E423D; T394M, L453P; T394M, F458S; T394M, E461G; T394M, F465C; T394M, N467T; T394M, N470S; T394M, A476T; T394M, Q494R; T394M, T496R; T394M, G504S; F396Y, R400C; F396Y, T413A; F396Y, E423D; F396Y, L453P; F396Y, F458S; F396Y, E461G; F396Y, F465C; F396Y, N467T; F396Y, N470S; F396Y, A476T; F396Y, Q494R; F396Y, T496R; F396Y, G504S; R400C, T413A; R400C, E423D; R400C, L453P; R400C, F458S; R400C, E461G; R400C, F465C; R400C, N467T; R400C, N470S; R400C, A476T; R400C, Q494R; R400C, T496R; R400C, 504S; T413A, E423D; T413A, L453P; T413A, F458S; T413A, E461G; T413A, F465C; T413A, N467T; T413A, N470S; T413A, A476T; T413A, Q494R; T413A, T496R; T413A, G504S; E423D, L453P; E423D, F458S; E423D, E461G; E423D, F465C; E423D, N467T; E423D, N470S; E423D, A476T; E423D, Q494R; E423D, T496R; E423D, G504S; L453P, F458S; L453P, E461G; L453P, F465C; L453P, N467T; L453P, N470S; L453P, A476T; L453P, Q494R; L453P, T496R; L453P, G504S; F458S, E461G; F458S, F465C; F458S, N467T; F458S, N470S; F458S, A476T; F458S, Q494R; F458S, T496R; F458S, G504S; E461G, F465C; E461G, N467T; E461G, N470S; E461G, A476T; E461G, Q494R; E461G, T496R; E461G, G504S; F465C, N467T; F465C, N470S; F465C, A476T; F465C, Q494R; F465C, T496R; F465C, G504S; N467T, N470S; N467T, A476T; N467T, Q494R; N467T, T496R; N467T, G504S; N470S, A476T; N470S, Q494R; N470S, T496R; N470S, G504S; A476T, Q494R; A476T, T496R; A476T, G504S;

Q494R, T496R; Q494R, G504S; T496R, G504S; S2P, M71V, E96V; S2P, M71V, D101G; S2P, M71V, G112S; S2P, M71V, L114P; S2P, M71V, S130L; S2P, M71V, K145M; S2P, M71V, N166S; S2P, M71V, F171I; S2P, M71V, D203A; S2P, M71V, D203G; S2P, M71V, T213A; S2P, M71V, V225I; S2P, M71V, K237E; S2P, M71V, V256I; S2P, M71V, T258A; S2P, M71V, D264G; S2P, M71V, T283A; S2P, M71V, L289P; S2P, M71V, F312L; S2P, M71V, T348A; S2P, M71V, L380F; S2P, M71V, T394M; S2P, M71V, F396Y; S2P, M71V, R400C; S2P, M71V, T413A; S2P, M71V, E423D; S2P, M71V, L453P; S2P, M71V, F458S; S2P, M71V, E461G; S2P, M71V, F465C; S2P, M71V, N467T; S2P, M71V, N470S; S2P, M71V, A476T; S2P, M71V, Q494R; S2P, M71V, T496R; S2P, M71V, G504S; S2P, M71T, E96V; S2P, M71T, D101G; S2P, M71T, G112S; S2P, M71T, L114P; S2P, M71T, S130L; S2P, M71T, K145M; S2P, M71T, N166S; S2P, M71T, F171I; S2P, M71T, D203A; S2P, M71T, D203G; S2P, M71T, T213A; S2P, M71T, V225I; S2P, M71T, K237E; S2P, M71T, V256I; S2P, M71T, T258A; S2P, M71T, D264G; S2P, M71T, T283A; S2P, M71T, L289P; S2P, M71T, F312L; S2P, M71T, T348A; S2P, M71T, L380F; S2P, M71T, T394M; S2P, M71T, 396Y; S2P, M71T, R400C; S2P, M71T, T413A; S2P, M71T, E423D; S2P, M71T, L453P; S2P, M71T, F458S; S2P, M71T, E461G; S2P, M71T, F465C; S2P, M71T, N467T; S2P, M71T, N470S; S2P, M71T, A476T; S2P, M71T, Q494R; S2P, M71T, T496R; S2P, M71T, G504S; S2P, M71A, E96V; S2P, M71A, D101G; S2P, M71A, G112S; S2P, M71A, L114P; S2P, M71A, S130L; S2P, M71A, K145M; S2P, M71A, N166S; S2P, M71A, F171I; S2P, M71A, D203A; S2P, M71A, D203G; S2P, M71A, T213A; S2P, M71A, V225I; S2P, M71A, K237E; S2P, M71A, V256I; S2P, M71A, T258A; S2P, M71A, D264G; S2P, M71A, T283A; S2P, M71A, L289P; S2P, M71A, F312L; S2P, M71A, T348A; S2P, M71A, L380F; S2P, M71A, T394M; S2P, M71A, F396Y; S2P, M71A, R400C; S2P, M71A, T413A; S2P, M71A, E423D; S2P, M71A, L453P; S2P, M71A, F458S; S2P, M71A, E461G; S2P, M71A, F465C; S2P, M71A, N467T; S2P, M71A, N470S; S2P, M71A, A476T; S2P, M71A, Q494R; S2P, M71A, T496R; S2P, M71A, G504S; S2P, M71C, E96V; S2P, M71C, D101G; S2P, M71C, G112S; S2P, M71C, L114P; S2P, M71C, S130L; S2P, M71C, K145M; S2P, M71C, N166S; S2P, M71C, F171I; S2P, M71C, D203A; S2P, M71C, D203G; S2P, M71C, T213A; S2P, M71C, V225I; S2P, M71C, K237E; S2P, M71C, V256I; S2P, M71C, T258A; S2P, M71C, D264G; S2P, M71C, T283A; S2P, M71C, L289P; S2P, M71C, F312L; S2P, M71C, T348A; S2P, M71C, L380F; S2P, M71C, T394M; S2P, M71C, F396Y; S2P, M71C, R400C; S2P, M71C, T413A; S2P, M71C, E423D; S2P, M71C, L453P; S2P, M71C, F458S; S2P, M71C, E461G; S2P, M71C, F465C; S2P, M71C, N467T; S2P, M71C, N470S; S2P, M71C, A476T; S2P, M71C, Q494R; S2P, M71C, T496R; S2P, M71C, G504S; S2P, M71V, N75K; S2P, M71T, N75K; S2P, M71A, N75K; S2P, M71C, N75K; S2P, N75K, E96V; S2P, N75K, D101G; S2P, N75K, G112S; S2P, N75K, L114P; S2P, N75K, S130L; S2P, N75K, K145M; S2P, N75K, N166S; S2P, N75K, F171I; S2P, N75K, 203A; S2P, N75K, D203G; S2P, N75K, T213A; S2P, N75K, V225I; S2P, N75K, K237E; S2P, N75K, V256I; S2P, N75K, T258A; S2P, N75K, D264G; S2P, N75K, T283A; S2P, N75K, L289P; S2P, N75K, F312L; S2P, N75K, T348A; S2P, N75K, L380F; S2P, N75K, T394M; S2P, N75K, 396Y; S2P, N75K, R400C; S2P, N75K, T413A; S2P, N75K, E423D; S2P, N75K, L453P; S2P, N75K, F458S; S2P, N75K, E461G; S2P, N75K, F465C; S2P, N75K, N467T; S2P, N75K, 470S; S2P, N75K, A476T; S2P, N75K, Q494R; S2P, N75K, T496R;

S2P, N75K, G504S; M71V, 75K, E96V; M71V, N75K, D101G; M71V, N75K, G112S; M71V, N75K, L114P; M71V, N75K, S130L; M71V, N75K, K145M; M71V, N75K, N166S; M71V, N75K, F171I; M71V, N75K, D203A; M71V, N75K, D203G; M71V, N75K, T213A; M71V, N75K, V225I; M71V, N75K, K237E; M71V, N75K, V256I; M71V, N75K, T258A; M71V, N75K, D264G; M71V, N75K, T283A; M71V, N75K, L289P; M71V, N75K, F312L; M71V, N75K, T348A; M71V, N75K, L380F; M71V, N75K, T394M; M71V, N75K, F396Y; M71V, N75K, R400C; M71V, N75K, T413A; M71V, N75K, E423D; M71V, N75K, L453P; M71V, N75K, F458S; M71V, N75K, E461G; M71V, N75K, F465C; M71V, N75K, N467T; M71V, N75K, N470S; M71V, N75K, A476T; M71V, N75K, Q494R; M71V, N75K, T496R; M71V, N75K, G504S; M71T, N75K, E96V; M71T, N75K, D101G; M71T, N75K, G112S; M71T, N75K, L114P; M71T, N75K, S130L; M71T, N75K, K145M; M71T, N75K, N166S; M71T, N75K, F171I; M71T, N75K, D203A; M71T, N75K, D203G; M71T, N75K, T213A; M71T, N75K, V225I; M71T, N75K, K237E; M71T, N75K, V256I; M71T, N75K, T258A; M71T, N75K, D264G; M71T, N75K, T283A; M71T, N75K, L289P; M71T, N75K, F312L; M71T, N75K, T348A; M71T, N75K, L380F; M71T, N75K, T394M; M71T, N75K, F396Y; M71T, N75K, R400C; M71T, N75K, T413A; M71T, N75K, E423D; M71T, N75K, L453P; M71T, N75K, F458S; M71T, N75K, E461G; M71T, N75K, F465C; M71T, N75K, N467T; M71T, N75K, N470S; M71T, N75K, A476T; M71T, N75K, Q494R; M71T, N75K, T496R; M71T, N75K, G504S; M71A, N75K, E96V; M71A, N75K, D101G; M71A, N75K, G112S; M71A, N75K, L114P; M71A, N75K, S130L; M71A, N75K, K145M; M71A, N75K, N166S; M71A, N75K, F171I; M71A, N75K, D203A; M71A, N75K, D203G; M71A, N75K, T213A; M71A, N75K, V225I; M71A, N75K, K237E; M71A, N75K, V256I; M71A, N75K, T258A; M71A, N75K, D264G; M71A, N75K, T283A; M71A, N75K, L289P; M71A, N75K, F312L; M71A, N75K, T348A; M71A, N75K, L380F; M71A, N75K, T394M; M71A, N75K, F396Y; M71A, N75K, R400C; M71A, N75K, T413A; M71A, N75K, E423D; M71A, N75K, L453P; M71A, N75K, F458S; M71A, N75K, E461G; M71A, N75K, F465C; M71A, N75K, N467T; M71A, N75K, N470S; M71A, N75K, A476T; M71A, N75K, Q494R; M71A, N75K, T496R; M71A, N75K, G504S; M71C, N75K, E96V; M71C, N75K, D101G; M71C, N75K, G112S; M71C, N75K, L114P; M71C, N75K, S130L; M71C, N75K, K145M; M71C, N75K, N166S; M71C, N75K, F171I; M71C, N75K, D203A; M71C, N75K, D203G; M71C, N75K, T213A; M71C, N75K, V225I; M71C, N75K, K237E; M71C, N75K, V256I; M71C, N75K, T258A; M71C, N75K, D264G; M71C, N75K, T283A; M71C, N75K, L289P; M71C, N75K, F312L; M71C, N75K, T348A; M71C, N75K, L380F; M71C, N75K, T394M; M71C, N75K, F396Y; M71C, N75K, R400C; M71C, N75K, T413A; M71C, N75K, E423D; M71C, N75K, L453P; M71C, N75K, F458S; M71C, N75K, E461G; M71C, N75K, F465C; M71C, N75K, N467T; M71C, N75K, N470S; M71C, N75K, A476T; M71C, N75K, Q494R; M71C, N75K, T496R; M71C, N75K, G504S; N75K, E96V, D101G; N75K, E96V, G112S; N75K, E96V, L114P; N75K, E96V, S130L; N75K, E96V, K145M; N75K, E96V, N166S; N75K, E96V, F171I; N75K, E96V, D203A; N75K, E96V, D203G; N75K, E96V, T213A; N75K, E96V, V225I; N75K, E96V, K237E; N75K, E96V, V256I; N75K, E96V, T258A; N75K, E96V, D264G; N75K, E96V, T283A; N75K, E96V, L289P; N75K, E96V, F312L; N75K, E96V, T348A; N75K, E96V, L380F; N75K, E96V, T394M; N75K, E96V, F396Y;

N75K, E96V, R400C; N75K, E96V, T413A; N75K, E96V, E423D; N75K, E96V, L453P; N75K, E96V, F458S; N75K, E96V, E461G; N75K, E96V, F465C; N75K, E96V, N467T; N75K, E96V, N470S; N75K, E96V, A476T; N75K, E96V, Q494R; N75K, E96V, T496R; N75K, E96V, G504S; E96V, D101G, G112S; E96V, D101G, L114P; E96V, D101G, S130L; E96V, D101G, K145M; E96V, D101G, N166S; E96V, D101G, F171I; E96V, D101G, D203A; E96V, D101G, D203G; E96V, D101G, T213A; E96V, D101G, V225I; E96V, D101G, K237E; E96V, D101G, V256I; E96V, D101G, T258A; E96V, D101G, D264G; E96V, D101G, T283A; E96V, D101G, L289P; E96V, D101G, F312L; E96V, D101G, T348A; E96V, D101G, L380F; E96V, D101G, T394M; E96V, D101G, F396Y; E96V, D101G, R400C; E96V, D101G, T413A; E96V, D101G, E423D; E96V, D101G, L453P; E96V, D101G, F458S; E96V, D101G, E461G; E96V, D101G, F465C; E96V, D101G, N467T; E96V, D101G, N470S; E96V, D101G, A476T; E96V, D101G, Q494R; E96V, D101G, T496R; E96V, D101G, G504S; D101G, G112S, L114P; D101G, G112S, S130L; D101G, G112S, K145M; D101G, G112S, N166S; D101G, G112S, F171I; D101G, G112S, D203A; D101G, G112S, D203G; D101G, G112S, T213A; D101G, G112S, V225I; D101G, G112S, K237E; D101G, G112S, V256I; D101G, G112S, T258A; D101G, G112S, D264G; D101G, G112S, T283A; D101G, G112S, L289P; D101G, G112S, F312L; D101G, G112S, T348A; D101G, G112S, L380F; D101G, G112S, T394M; D101G, G112S, F396Y; D101G, G112S, R400C; D101G, G112S, T413A; D101G, G112S, E423D; D101G, G112S, L453P; D101G, G112S, F458S; D101G, G112S, E461G; D101G, G112S, F465C; D101G, G112S, N467T; D101G, G112S, N470S; D101G, G112S, A476T; D101G, G112S, Q494R; D101G, G112S, T496R; D101G, G112S, G504S; G112S, L114P, S130L; G112S, L114P, K145M; G112S, L114P, N166S; G112S, L114P, F171I; G112S, L114P, D203A; G112S, L114P, D203G; G112S, L114P, T213A; G112S, L114P, V225I; G112S, L114P, K237E; G112S, L114P, V256I; G112S, L114P, T258A; G112S, L114P, D264G; G112S, L114P, T283A; G112S, L114P, L289P; G112S, L114P, F312L; G112S, L114P, T348A; G112S, L114P, L380F; G112S, L114P, T394M; G112S, L114P, F396Y; G112S, L114P, R400C; G112S, L114P, T413A; G112S, L114P, E423D; G112S, L114P, L453P; G112S, L114P, F458S; G112S, L114P, E461G; G112S, L114P, F465C; G112S, L114P, N467T; G112S, L114P, N470S; G112S, L114P, A476T; G112S, L114P, Q494R; G112S, L114P, T496R; G112S, L114P, G504S; L114P, S130L, K145M; L114P, S130L, N166S; L114P, S130L, F171I, L114P, S130L, D203A; L114P, S130L, D203G; L114P, S130L, T213A; L114P, S130L, V225I; L114P, S130L, K237E; L114P, S130L, V256I; L114P, S130L, T258A; L114P, S130L, D264G; L114P, S130L, T283A; L114P, S130L, L289P; L114P, S130L, F312L; L114P, S130L, T348A; L114P, S130L, L380F; L114P, S130L, T394M; L114P, S130L, F396Y; L114P, S130L, R400C; L114P, S130L, T413A; L114P, S130L, E423D; L114P, S130L, L453P; L114P, S130L, F458S; L114P, S130L, E461G; L114P, S130L, F465C; L114P, S130L, N467T; L114P, S130L, N470S; L114P, S130L, A476T; L114P, S130L, Q494R; L114P, S130L, T496R; L114P, S130L, G504S; S130L, K145M, N166S; S130L, K145M, F171I; S130L, K145M, D203A; S130L, K145M, D203G; S130L, K145M, T213A; S130L, K145M, V225I; S130L, K145M, K237E; S130L, K145M, V256I; S130L, K145M, T258A; S130L, K145M, D264G; S130L, K145M, T283A; S130L, K145M, L289P; S130L, K145M, F312L; S130L, K145M, T348A; S130L, K145M, L380F; S130L, K145M, T394M; S130L, K145M, F396Y; S130L, K145M, R400C; S130L, K145M, T413A; S130L, K145M, E423D; S130L, K145M, L453P; S130L, K145M, F458S; S130L, K145M, E461G; S130L, K145M, F465C; S130L, K145M, N467T; S130L, K145M, N470S; S130L K145M, A476T; S130L, K145M, Q494R; S130L, K145M, T496R; S130L, K145M, G504S; K145M, N166S, F171I; K145M, N166S, D203A; K145M, N166S, D203G; K145M, N166S, T213A; K145M, N166S, V225I; K145M, N166S, K237E; K145M, N166S, V256I; K145M, N166S, T258A; K145M, N166S, D264G; K145M, N166S, T283A; K145M, N166S, L289P; K145M, N166S, F312L; K145M, N166S, T348A; K145M, N166S, L380F; K145M, N166S, 394M; K145M, N166S, F396Y; K145M, N166S, R400C; K145M, N166S, T413A; K145M, N166S, E423D; K145M, N166S, L453P; K145M, N166S, F458S; K145M, N166S, E461G; K145M, N166S, F465C; K145M, N166S, N467T; K145M, N166S, N470S; K145M, N166S, A476T; K145M, N166S, Q494R; K145M, N166S, T496R; K145M, N166S, G504S; N166S, F171I, D203A; N166S, F171I, D203G; N166S, F171I, T213A; N166S, F171I, V225I; N166S, F171I, K237E; N166S, F171I, V256I; N166S, F171I, T258A; N166S, F171I, D264G; N166S, F171I, T283A; N166S, F171I, L289P; N166S, F171I, F312L; N166S, F171I, T348A; N166S, F171I, L380F; N166S, F171I, T394M; N166S, F171I, F396Y; N166S, F171I, R400C; N166S, F171I, T413A; N166S, F171I, E423D; N166S, F171I, L453P; N166S, F171I, F458S; N166S, F171I, E461G; N166S, F171I, F465C; N166S, F171I, N467T; N166S, F171I, N470S; N166S, F171I, A476T; N166S, F171I, Q494R; N166S, F171I, T496R; N166S, F171I, G504S; F171I, D203A, D203G; F171I, D203A, T213A; F171I, D203A, V225I; F171I, D203A, K237E; F171I, D203A, V256I; F171I, D203A, T258A; F171I, D203A, D264G; F171I, D203A, T283A; F171I, D203A, L289P; F171I, D203A, F312L; F171I, D203A, T348A; F171I, D203A, L380F; F171I, D203A, T394M; F171I, D203A, F396Y; F171I, D203A, R400C; F171I, D203A, T413A; F171I, D203A, E423D; F171I, D203A, L453P; F171I, D203A, F458S; F171I, D203A, E461G; F171I, D203A, F465C; F171I, D203A, N467T; F171I, D203A, N470S; F171I, D203A, A476T; F171I, D203A, Q494R; F171I, D203A, T496R; F171I, D203A, G504S; D203A, T213A, V225I; D203A, T213A, K237E; D203A, T213A, V256I; D203A, T213A, T258A; D203A, T213A, D264G; D203A, T213A, T283A; D203A, T213A, L289P; D203A, T213A, F312L; D203A, T213A, T348A; D203A, T213A, L380F; D203A, T213A, T394M; D203A, T213A, F396Y; D203A, T213A, R400C; D203A, T213A, T413A; D203A, T213A, E423D; D203A, T213A, L453P; D203A, T213A, F458S; D203A, T213A, E461G; D203A, T213A, F465C; D203A, T213A, N467T; D203A, T213A, N470S; D203A, T213A, A476T; D203A, T213A, Q494R; D203A, T213A, T496R; D203A, T213A, G504S; D203C, T213A, V225I; D203C, T213A, K237E; D203C, T213A, V256I; D203C, T213A, T258A; D203C, T213A, D264G; D203C, T213A, T283A; D203C, T213A, L289P; D203C, T213A, F312L; D203C, T213A, T348A; D203C, T213A, L380F; D203C, T213A, T394M; D203C, T213A, F396Y; D203C, T213A, R400C; D203C, T213A, T413A; D203C, T213A, E423D; D203C, T213A, L453P; D203C, T213A, F458S; D203C, T213A, E461G; D203C, T213A, F465C; D203C, T213A, N467T; D203C, T213A, N470S; D203C, T213A, A476T; D203C, T213A, Q494R; D203C, T213A, T496R; D203C, T213A, G504S; T213A, V225I, K237E; T213A, V225I, V256I; T213A, V225I, T258A; T213A, V225I, D264G; T213A, V225I, T283A; T213A, V225I, L289P; T213A, V225I, F312L; T213A, V225I,

T348A; T213A, V225I, L380F; T213A, V225I, T394M; T213A, V225I, F396Y; T213A, V225I, R400C; T213A, V225I, T413A; T213A, V225I, E423D; T213A, V225I, L453P; T213A, V225I, F458S; T213A, V225I, E461G; T213A, V225I, F465C; T213A, V225I, N467T; T213A, V225I, N470S; T213A, V225I, A476T; T213A, V225I, Q494R; T213A, V225I, T496R; T213A, V225I, G504S; V225I, K237E, V256I; V225I, K237E, T258A; V225I, K237E, D264G; V225I, K237E, T283A; V225I, K237E, L289P; V225I, K237E, F312L; V225I, K237E, T348A; V225I, K237E, L380F; V225I, K237E, T394M; V225I, K237E, F396Y; V225I, K237E, R400C; V225I, K237E, T413A; V225I, K237E, E423D; V225I, K237E, L453P; V225I, K237E, F458S; V225I, K237E, E461G; V225I, K237E, F465C; V225I, K237E, N467T; V225I, K237E, N470S; V225I, K237E, A476T; V225I, K237E, Q494R; V225I, K237E, T496R; V225I, K237E, G504S; K237E, V256I, T258A; K237E, V256I, D264G; K237E, V256I, T283A; K237E, V256I, L289P; K237E, V256I, F312L; K237E, V256I, T348A; K237E, V256I, L380F; K237E, V256I, T394M; K237E, V256I, F396Y; K237E, V256I, R400C; K237E, V256I, T413A; K237E, V256I, E423D; K237E, V256I, L453P; K237E, V256I, F458S; K237E, V256I, E461G; K237E, V256I, F465C; K237E, V256I, N467T; K237E, V256I, N470S; K237E, V256I, A476T; K237E, V256I, Q494R; K237E, V256I, T496R; K237E, V256I, G504S; V256I, T258A, D264G; V256I, T258A, T283A; V256I, T258A, L289P; V256I, T258A, F312L; V256I, T258A, T348A; V256I, T258A, L380F; V256I, T258A, T394M; V256I, T258A, F396Y; V256I, T258A, R400C; V256I, T258A, T413A; V256I, T258A, E423D; V256I, T258A, L453P; V256I, T258A, F458S; V256I, T258A, E461G; V256I, T258A, F465C; V256I, T258A, N467T; V256I, T258A, N470S; V256I, T258A, A476T; V256I, T258A, Q494R; V256I, T258A, T496R; V256I, T258A, G504S; T258A, D264G, T283A; T258A, D264G, L289P; T258A, D264G, F312L; T258A, D264G, T348A; T258A, D264G, L380F; T258A, D264G, T394M; T258A, D264G, F396Y; T258A, D264G, R400C; T258A, D264G, T413A; T258A, D264G, E423D; T258A, D264G, L453P; T258A, D264G, F458S; T258A, D264G, E461G; T258A, D264G, F465C; T258A, D264G, N467T; T258A, D264G, N470S; T258A, D264G, A476T; T258A, D264G, Q494R; T258A, D264G, T496R; T258A, D264G, G504S; D264G, T283A, L289P; D264G, T283A, F312L; D264G, T283A, T348A; D264G, T283A, L380F; D264G, T283A, T394M; D264G, T283A, F396Y; D264G, T283A, R400C; D264G, T283A, T413A; D264G, T283A, E423D; D264G, T283A, L453P; D264G, T283A, F458S; D264G, T283A, E461G; D264G, T283A, F465C; D264G, T283A, N467T; D264G, T283A, N470S; D264G, T283A, A476T; D264G, T283A, Q494R; D264G, T283A, T496R; D264G, T283A, G504S; T283A, L289P, F312L; T283A, L289P, T348A; T283A, L289P, L380F; T283A, L289P, T394M; T283A, L289P, F396Y; T283A, L289P, R400C; T283A, L289P, T413A; T283A, L289P, E423D; T283A, L289P, L453P; T283A, L289P, F458S; T283A, L289P, E461G; T283A, L289P, F465C; T283A, L289P, N467T; T283A, L289P, N470S; T283A, L289P, A476T; T283A, L289P, Q494R; T283A, L289P, T496R; T283A, L289P, G504S; L289P, F312L, T348A; L289P, F312L, L380F; L289P, F312L, T394M; L289P, F312L, F396Y; L289P, F312L, R400C; L289P, F312L, T413A; L289P, F312L, E423D; L289P, F312L, L453P; L289P, F312L, F458S; L289P, F312L, E461G; L289P, F312L, F465C; L289P, F312L, N467T; L289P, F312L, N470S; L289P, F312L, A476T; L289P, F312L, Q494R; L289P, F312L, T496R; L289P, F312L, G504S; F312L, T348A, L380F; F312L, T348A, T394M; F312L, T348A, F396Y; F312L, T348A, R400C; F312L, T348A, T413A; F312L, T348A, E423D; F312L, T348A, L453P; F312L, T348A, F458S; F312L, T348A, E461G; F312L, T348A, F465C; F312L, T348A, N467T; F312L, T348A, N470S; F312L, T348A, A476T; F312L, T348A, Q494R; F312L, T348A, T496R; F312L, T348A, G504S; T348A, L380F, T394M; T348A, L380F, F396Y; T348A, L380F, R400C; T348A, L380F, T413A; T348A, L380F, E423D; T348A, L380F, L453P; T348A, L380F, F458S; T348A, L380F, E461G; T348A, L380F, F465C; T348A, L380F, N467T; T348A, L380F, N470S; T348A, L380F, A476T; T348A, L380F, Q494R; T348A, L380F, T496R; T348A, L380F, G504S; L380F, T394M, F396Y; L380F, T394M, R400C; L380F, T394M, T413A; L380F, T394M, E423D; L380F, T394M, L453P; L380F, T394M, F458S; L380F, T394M, E461G; L380F, T394M, F465C; L380F, T394M, N467T; L380F, T394M, N470S; L380F, T394M, A476T; L380F, T394M, Q494R; L380F, T394M, T496R; L380F, T394M, G504S; T394M, F396Y, R400C; T394M, F396Y, T413A; T394M, F396Y, E423D; T394M, F396Y, L453P; T394M, F396Y, F458S; T394M, F396Y, E461G; T394M, F396Y, F465C; T394M, F396Y, N467T; T394M, F396Y, N470S; T394M, F396Y, A476T; T394M, F396Y, Q494R; T394M, F396Y, T496R; T394M, F396Y, G504S; F396Y, R400C, T413A; F396Y, R400C, E423D; F396Y, R400C, L453P; F396Y, R400C, F458S; F396Y, R400C, E461G; F396Y, R400C, F465C; F396Y, R400C, N467T; F396Y, R400C, N470S; F396Y, R400C, A476T; F396Y, R400C, Q494R; F396Y, R400C, T496R; F396Y, R400C, G504S; R400C, T413A, E423D; R400C, T413A, L453P; R400C, T413A, F458S; R400C, T413A, E461G; R400C, T413A, F465C; R400C, T413A, N467T; R400C, T413A, N470S; R400C, T413A, A476T; R400C, T413A, Q494R; R400C, T413A, T496R; R400C, T413A, G504S; T413A, E423D, L453P; T413A, E423D, F458S; T413A, E423D, E461G; T413A, E423D, F465C; T413A, E423D, N467T; T413A, E423D, N470S; T413A, E423D, A476T; T413A, E423D, Q494R; T413A, E423D, T496R; T413A, E423D, G504S; E423D, L453P, F458S; E423D, L453P, E461G; E423D, L453P, F465C; E423D, L453P, N467T; E423D, L453P, N470S; E423D, L453P, A476T; E423D, L453P, Q494R; E423D, L453P, T496R; E423D, L453P, G504S; L453P, F458S, E461G; L453P, F458S, F465C; L453P, F458S, N467T; L453P, F458S, N470S; L453P, F458S, A476T; L453P, F458S, Q494R; L453P, F458S, T496R; L453P, F458S, G504S; F458S, E461G, F465C; F458S, E461G, N467T; F458S, E461G, N470S; F458S, E461G, A476T; F458S, E461G, Q494R; F458S, E461G, T496R; F458S, E461G, G504S; E461G, F465C, N467T; E461G, F465C, N470S; E461G, F465C, A476T; E461G, F465C, Q494R; E461G, F465C, T496R; E461G, F465C, G504S; F465C, N467T, N470S; F465C, N467T, A476T; F465C, N467T, Q494R; F465C, N467T, T496R; F465C, N467T, G504S; N467T, N470S, A476T; N467T, N470S, Q494R; N467T, N470S, T496R; N467T, N470S, G504S; N470S, A476T, Q494R; N470S, A476T, T496R; N470S, A476T, G504S; A476T, Q494R, T496R; A476T, Q494R, G504S; Q494R, T496R, G504S; S2P, M71V, N75K, E96V; S2P, M71V, E96V, D101G; S2P, M71V, E96V, G112S; S2P, M71V, E96V, L114P; S2P, M71V, E96V, S130L; S2P, M71V, E96V, K145M; S2P, M71V, E96V, N166S; S2P, M71V, E96V, F171I; S2P, M71V, E96V, D203A; S2P, M71V, E96V, D203G; S2P, M71V, E96V, T213A; S2P, M71V, E96V, V225I; S2P, M71V, E96V, K237E; S2P, M71V, E96V, V256I; S2P, M71V, E96V, T258A; S2P, M71V, E96V, D264G; S2P, M71V, E96V, T283A; S2P, M71V, E96V,

L289P; S2P, M71V, E96V, F312L; S2P, M71V, E96V, T348A; S2P, M71V, E96V, L380F; S2P, M71V, E96V, T394M; S2P, M71V, E96V, F396Y; S2P, M71V, E96V, R400C; S2P, M71V, E96V, T413A; S2P, M71V, E96V, E423D; S2P, M71V, E96V, L453P; S2P, M71V, E96V, F458S; S2P, M71V, E96V, E461G; S2P, M71V, E96V, F465C; S2P, M71V, E96V, N467T; S2P, M71V, E96V, N470S; S2P, M71V, E96V, A476T; S2P, M71V, E96V, Q494R; S2P, M71V, E96V, T496R; S2P, M71V, E96V, G504S; S2P, M71T, E96V, D101G; S2P, M71T, E96V, G112S; S2P, M71T, E96V, L114P; S2P, M71T, E96V, S130L; S2P, M71T, E96V, K145M; S2P, M71T, E96V, N166S; S2P, M71T, E96V, F171I; S2P, M71T, E96V, D203A; S2P, M71T, E96V, D203G; S2P, M71T, E96V, T213A; S2P, M71T, E96V, V225I; S2P, M71T, E96V, K237E; S2P, M71T, E96V, V256I; S2P, M71T, E96V, T258A; S2P, M71T, E96V, D264G; S2P, M71T, E96V, T283A; S2P, M71T, E96V, L289P; S2P, M71T, E96V, F312L; S2P, M71T, E96V, T348A; S2P, M71T, E96V, L380F; S2P, M71T, E96V, T394M; S2P, M71T, E96V, F396Y; S2P, M71T, E96V, R400C; S2P, M71T, E96V, T413A; S2P, M71T, E96V, E423D; S2P, M71T, E96V, L453P; S2P, M71T, E96V, F458S; S2P, M71T, E96V, E461G; S2P, M71T, E96V, F465C; S2P, M71T, E96V, N467T; S2P, M71T, E96V, N470S; S2P, M71T, E96V, A476T; S2P, M71T, E96V, Q494R; S2P, M71T, E96V, T496R; S2P, M71T, E96V, G504S; S2P, M71A, E96V, D101G; S2P, M71A, E96V, G112S; S2P, M71A, E96V, L114P; S2P, M71A, E96V, S130L; S2P, M71A, E96V, K145M; S2P, M71A, E96V, N166S; S2P, M71A, E96V, F171I; S2P, M71A, E96V, D203A; S2P, M71A, E96V, D203G; S2P, M71A, E96V, T213A; S2P, M71A, E96V, V225I; S2P, M71A, E96V, K237E; S2P, M71A, E96V, V256I; S2P, M71A, E96V, T258A; S2P, M71A, E96V, D264G; S2P, M71A, E96V, T283A; S2P, M71A, E96V, L289P; S2P, M71A, E96V, F312L; S2P, M71A, E96V, T348A; S2P, M71A, E96V, L380F; S2P, M71A, E96V, T394M; S2P, M71A, E96V, F396Y; S2P, M71A, E96V, R400C; S2P, M71A, E96V, T413A; S2P, M71A, E96V, E423D; S2P, M71A, E96V, L453P; S2P, M71A, E96V, F458S; S2P, M71A, E96V, E461G; S2P, M71A, E96V, F465C; S2P, M71A, E96V, N467T; S2P, M71A, E96V, N470S; S2P, M71A, E96V, A476T; S2P, M71A, E96V, Q494R; S2P, M71A, E96V, T496R; S2P, M71A, E96V, G504S; S2P, M71C, E96V, D101G; S2P, M71C, E96V, G112S; S2P, M71C, E96V, L114P; S2P, M71C, E96V, S130L; S2P, M71C, E96V, K145M; S2P, M71C, E96V, N166S; S2P, M71C, E96V, F171I; S2P, M71C, E96V, D203A; S2P, M71C, E96V, D203G; S2P, M71C, E96V, T213A; S2P, M71C, E96V, V225I; S2P, M71C, E96V, K237E; S2P, M71C, E96V, V256I; S2P, M71C, E96V, T258A; S2P, M71C, E96V, D264G; S2P, M71C, E96V, T283A; S2P, M71C, E96V, L289P; S2P, M71C, E96V, F312L; S2P, M71C, E96V, T348A; S2P, M71C, E96V, L380F; S2P, M71C, E96V, T394M; S2P, M71C, E96V, F396Y; S2P, M71C, E96V, R400C; S2P, M71C, E96V, T413A; S2P, M71C, E96V, E423D; S2P, M71C, E96V, L453P; S2P, M71C, E96V, F458S; S2P, M71C, E96V, E461G; S2P, M71C, E96V, F465C; S2P, M71C, E96V, N467T; S2P, M71C, E96V, N470S; S2P, M71C, E96V, A476T; S2P, M71C, E96V, Q494R; S2P, M71C, E96V, T496R; S2P, M71C, E96V, G504S; S2P, M71V, D101G, G112S; S2P, M71V, D101G, L114P; S2P, M71V, D101G, S130L; S2P, M71V, D101G, K145M; S2P, M71V, D101G, N166S; S2P, M71V, D101G, F171I; S2P, M71V, D101G, D203A; S2P, M71V, D101G, D203G; S2P, M71V, D101G, T213A; S2P, M71V, D101G, V225I; S2P, M71V, D101G, K237E; S2P, M71V, D101G, V256I; S2P, M71V, D101G, T258A; S2P, M71V, D101G, D264G; S2P, M71V, D101G, T283A; S2P, M71V, D101G, L289P; S2P, M71V, D101G, F312L; S2P, M71V, D101G, T348A; S2P, M71V, D101G, L380F; S2P, M71V, D101G, T394M; S2P, M71V, D101G, F396Y; S2P, M71V, D101G, R400C; S2P, M71V, D101G, T413A; S2P, M71V, D101G, E423D; S2P, M71V, D101G, L453P; S2P, M71V, D101G, F458S; S2P, M71V, D101G, E461G; S2P, M71V, D101G, F465C; S2P, M71V, D101G, N467T; S2P, M71V, D101G, N470S; S2P, M71V, D101G, A476T; S2P, M71V, D101G, Q494R; S2P, M71V, D101G, T496R; S2P, M71V, D101G, G504S; S2P, M71T, D101G, G112S; S2P, M71T, D101G, L114P; S2P, M71T, D101G, S130L; S2P, M71T, D101G, K145M; S2P, M71T, D101G, N166S; S2P, M71T, D101G, F171I; S2P, M71T, D101G, D203A; S2P, M71T, D101G, D203G; S2P, M71T, D101G, T213A; S2P, M71T, D101G, V225I; S2P, M71T, D101G, K237E; S2P, M71T, D101G, V256I; S2P, M71T, D101G, T258A; S2P, M71T, D101G, D264G; S2P, M71T, D101G, T283A; S2P, M71T, D101G, L289P; S2P, M71T, D101G, F312L; S2P, M71T, D101G, T348A; S2P, M71T, D101G, L380F; S2P, M71T, D101G, T394M; S2P, M71T, D101G, F396Y; S2P, M71T, D101G, R400C; S2P, M71T, D101G, T413A; S2P, M71T, D101G, E423D; S2P, M71T, D101G, L453P; S2P, M71T, D101G, F458S; S2P, M71T, D101G, E461G; S2P, M71T, D101G, F465C; S2P, M71T, D101G, N467T; S2P, M71T, D101G, N470S; S2P, M71T, D101G, A476T; S2P, M71T, D101G, Q494R; S2P, M71T, D101G, T496R; S2P, M71T, D101G, G504S; S2P, M71A, D101G, G112S; S2P, M71A, D101G, L114P; S2P, M71A, D101G, S130L; S2P, M71A, D101G, K145M; S2P, M71A, D101G, N166S; S2P, M71A, D101G, F171I; S2P, M71A, D101G, D203A; S2P, M71A, D101G, D203G; S2P, M71A, D101G, T213A; S2P, M71A, D101G, V225I; S2P, M71A, D101G, K237E; S2P, M71A, D101G, V256I; S2P, M71A, D101G, T258A; S2P, M71A, D101G, D264G; S2P, M71A, D101G, T283A; S2P, M71A, D101G, L289P; S2P, M71A, D101G, F312L; S2P, M71A, D101G, T348A; S2P, M71A, D101G, L380F; S2P, M71A, D101G, T394M; S2P, M71A, D101G, F396Y; S2P, M71A, D101G, R400C; S2P, M71A, D101G, T413A; S2P, M71A, D101G, E423D; S2P, M71A, D101G, L453P; S2P, M71A, D101G, F458S; S2P, M71A, D101G, E461G; S2P, M71A, D101G, F465C; S2P, M71A, D101G, N467T; S2P, M71A, D101G, N470S; S2P, M71A, D101G, A476T; S2P, M71A, D101G, Q494R; S2P, M71A, D101G, T496R; S2P, M71A, D101G, G504S; S2P, M71C, D101G, G112S; S2P, M71C, D101G, L114P; S2P, M71C, D101G, S130L; S2P, M71C, D101G, K145M; S2P, M71C, D101G, N166S; S2P, M71C, D101G, F171I; S2P, M71C, D101G, D203A; S2P, M71C, D101G, D203G; S2P, M71C, D101G, T213A; S2P, M71C, D101G, V225I; S2P, M71C, D101G, K237E; S2P, M71C, D101G, V256I; S2P, M71C, D101G, T258A; S2P, M71C, D101G, D264G; S2P, M71C, D101G, T283A; S2P, M71C, D101G, L289P; S2P, M71C, D101G, F312L; S2P, M71C, D101G, T348A; S2P, M71C, D101G, L380F; S2P, M71C, D101G, T394M; S2P, M71C, D101G, F396Y; S2P, M71C, D101G, R400C; S2P, M71C, D101G, T413A; S2P, M71C, D101G, E423D; S2P, M71C, D101G, L453P; S2P, M71C, D101G, F458S; S2P, M71C, D101G, E461G; S2P, M71C, D101G, F465C; S2P, M71C, D101G, N467T; S2P, M71C, D101G, N470S; S2P, M71C, D101G, A476T; S2P, M71C, D101G, Q494R; S2P, M71C, D101G, T496R; S2P, M71C, D101G, G504S; S2P, M71V, G112S, L114P; S2P, M71V, G112S, S130L; S2P, M71V, G112S, K145M; S2P, M71V, G112S, N166S; S2P, M71V, G112S, F171I; S2P, M71V, G112S, D203A; S2P, M71V, G112S, D203G; S2P, M71V, G112S, T213A; S2P, M71V, G112S,

V225I; S2P, M71V, G112S, K237E; S2P, M71V, G112S, V256I; S2P, M71V, G112S, T258A; S2P, M71V, G112S, D264G; S2P, M71V, G112S, T283A; S2P, M71V, G112S, L289P; S2P, M71V, G112S, F312L; S2P, M71V, G112S, T348A; S2P, M71V, G112S, L380F; S2P, M71V, G112S, T394M; S2P, M71V, G112S, F396Y; S2P, M71V, G112S, R400C; S2P, M71V, G112S, T413A; S2P, M71V, G112S, E423D; S2P, M71V, G112S, L453P; S2P, M71V, G112S, F458S; S2P, M71V, G112S, E461G; S2P, M71V, G112S, F465C; S2P, M71V, G112S, N467T; S2P, M71V, G112S, N470S; S2P, M71V, G112S, A476T; S2P, M71V, G112S, Q494R; S2P, M71V, G112S, T496R; S2P, M71V, G112S, G504S; S2P, M71T, G112S, L114P; S2P, M71T, G112S, S130L; S2P, M71T, G112S, K145M; S2P, M71T, G112S, N166S; S2P, M71T, G112S, F171I; S2P, M71T, G112S, D203A; S2P, M71T, G112S, D203G; S2P, M71T, G112S, T213A; S2P, M71T, G112S, V225I; S2P, M71T, G112S, K237E; S2P, M71T, G112S, V256I; S2P, M71T, G112S, T258A; S2P, M71T, G112S, D264G; S2P, M71T, G112S, T283A; S2P, M71T, G112S, L289P; S2P, M71T, G112S, F312L; S2P, M71T, G112S, T348A; S2P, M71T, G112S, L380F; S2P, M71T, G112S, T394M; S2P, M71T, G112S, F396Y; S2P, M71T, G112S, R400C; S2P, M71T, G112S, T413A; S2P, M71T, G112S, E423D; S2P, M71T, G112S, L453P; S2P, M71T, G112S, F458S; S2P, M71T, G112S, E461G; S2P, M71T, G112S, F465C; S2P, M71T, G112S, N467T; S2P, M71T, G112S, N470S; S2P, M71T, G112S, A476T; S2P, M71T, G112S, Q494R; S2P, M71T, G112S, T496R; S2P, M71T, G112S, G504S; S2P, M71A, G112S, L114P; S2P, M71A, G112S, S130L; S2P, M71A, G112S, K145M; S2P, M71A, G112S, N166S; S2P, M71A, G112S, F171I; S2P, M71A, G112S, D203A; S2P, M71A, G112S, D203G; S2P, M71A, G112S, T213A; S2P, M71A, G112S, V225I; S2P, M71A, G112S, K237E; S2P, M71A, G112S, V256I; S2P, M71A, G112S, T258A; S2P, M71A, G112S, D264G; S2P, M71A, G112S, T283A; S2P, M71A, G112S, L289P; S2P, M71A, G112S, F312L; S2P, M71A, G112S, T348A; S2P, M71A, G112S, L380F; S2P, M71A, G112S, T394M; S2P, M71A, G112S, F396Y; S2P, M71A, G112S, R400C; S2P, M71A, G112S, T413A; S2P, M71A, G112S, E423D; S2P, M71A, G112S, L453P; S2P, M71A, G112S, F458S; S2P, M71A, G112S, E461G; S2P, M71A, G112S, F465C; S2P, M71A, G112S, N467T; S2P, M71A, G112S, N470S; S2P, M71A, G112S, A476T; S2P, M71A, G112S, Q494R; S2P, M71A, G112S, T496R; S2P, M71A, G112S, G504S; S2P, M71C, G112S, L114P; S2P, M71C, G112S, S130L; S2P, M71C, G112S, K145M; S2P, M71C, G112S, N166S; S2P, M71C, G112S, F171I; S2P, M71C, G112S, D203A; S2P, M71C, G112S, D203G; S2P, M71C, G112S, T213A; S2P, M71C, G112S, V225I; S2P, M71C, G112S, K237E; S2P, M71C, G112S, V256I; S2P, M71C, G112S, T258A; S2P, M71C, G112S, D264G; S2P, M71C, G112S, T283A; S2P, M71C, G112S, L289P; S2P, M71C, G112S, F312L; S2P, M71C, G112S, T348A; S2P, M71C, G112S, L380F; S2P, M71C, G112S, T394M; S2P, M71C, G112S, F396Y; S2P, M71C, G112S, R400C; S2P, M71C, G112S, T413A; S2P, M71C, G112S, E423D; S2P, M71C, G112S, L453P; S2P, M71C, G112S, F458S; S2P, M71C, G112S, E461G; S2P, M71C, G112S, F465C; S2P, M71C, G112S, N467T; S2P, M71C, G112S, N470S; S2P, M71C, G112S, A476T; S2P, M71C, G112S, Q494R; S2P, M71C, G112S, T496R; S2P, M71C, G112S, G504S; S2P, M71V, L114P, S130L; S2P, M71V, L114P, K145M; S2P, M71V, L114P, N166S; S2P, M71V, L114P, F171I; S2P, M71V, L114P, D203A; S2P, M71V, L114P, D203G; S2P, M71V, L114P, T213A; S2P, M71V, L114P, V225I; S2P, M71V, L114P, K237E; S2P, M71V, L114P, V256I; S2P, M71V, L114P,

T258A; S2P, M71V, L114P, D264G; S2P, M71V, L114P, T283A; S2P, M71V, L114P, L289P; S2P, M71V, L114P, F312L; S2P, M71V, L114P, T348A; S2P, M71V, L114P, L380F; S2P, M71V, L114P, T394M; S2P, M71V, L114P, F396Y; S2P, M71V, L114P, R400C; S2P, M71V, L114P, T413A; S2P, M71V, L114P, E423D; S2P, M71V, L114P, L453P; S2P, M71V, L114P, F458S; S2P, M71V, L114P, E461G; S2P, M71V, L114P, F465C; S2P, M71V, L114P, N467T; S2P, M71V, L114P, N470S; S2P, M71V, L114P, A476T; S2P, M71V, L114P, Q494R; S2P, M71V, L114P, T496R; S2P, M71V, L114P, G504S; S2P, M71T, L114P, S130L; S2P, M71T, L114P, K145M; S2P, M71T, L114P, N166S; S2P, M71T, L114P, F171I; S2P, M71T, L114P, D203A; S2P, M71T, L114P, D203G; S2P, M71T, L114P, T213A; S2P, M71T, L114P, V225I; S2P, M71T, L114P, K237E; S2P, M71T, L114P, V256I; S2P, M71T, L114P, T258A; S2P, M71T, L114P, D264G; S2P, M71T, L114P, T283A; S2P, M71T, L114P, L289P; S2P, M71T, L114P, F312L; S2P, M71T, L114P, T348A; S2P, M71T, L114P, L380F; S2P, M71T, L114P, T394M; S2P, M71T, L114P, F396Y; S2P, M71T, L114P, R400C; S2P, M71T, L114P, T413A; S2P, M71T, L114P, E423D; S2P, M71T, L114P, L453P; S2P, M71T, L114P, F458S; S2P, M71T, L114P, E461G; S2P, M71T, L114P, F465C; S2P, M71T, L114P, N467T; S2P, M71T, L114P, N470S; S2P, M71T, L114P, A476T; S2P, M71T, L114P, Q494R; S2P, M71T, L114P, T496R; S2P, M71T, L114P, G504S; S2P, M71A, L114P, S130L; S2P, M71A, L114P, K145M; S2P, M71A, L114P, N166S; S2P, M71A, L114P, F171I; S2P, M71A, L114P, D203A; S2P, M71A, L114P, D203G; S2P, M71A, L114P, T213A; S2P, M71A, L114P, V225I; S2P, M71A, L114P, K237E; S2P, M71A, L114P, V256I; S2P, M71A, L114P, T258A; S2P, M71A, L114P, D264G; S2P, M71A, L114P, T283A; S2P, M71A, L114P, L289P; S2P, M71A, L114P, F312L; S2P, M71A, L114P, T348A; S2P, M71A, L114P, L380F; S2P, M71A, L114P, T394M; S2P, M71A, L114P, F396Y; S2P, M71A, L114P, R400C; S2P, M71A, L114P, T413A; S2P, M71A, L114P, E423D; S2P, M71A, L114P, L453P; S2P, M71A, L114P, F458S; S2P, M71A, L114P, E461G; S2P, M71A, L114P, F465C; S2P, M71A, L114P, N467T; S2P, M71A, L114P, N470S; S2P, M71A, L114P, A476T; S2P, M71A, L114P, Q494R; S2P, M71A, L114P, T496R; S2P, M71A, L114P, G504S; S2P, M71C, L114P, S130L; S2P, M71C, L114P, K145M; S2P, M71C, L114P, N166S; S2P, M71C, L114P, F171I; S2P, M71C, L114P, D203A; S2P, M71C, L114P, D203G; S2P, M71C, L114P, T213A; S2P, M71C, L114P, V225I; S2P, M71C, L114P, K237E; S2P, M71C, L114P, V256I; S2P, M71C, L114P, T258A; S2P, M71C, L114P, D264G; S2P, M71C, L114P, T283A; S2P, M71C, L114P, L289P; S2P, M71C, L114P, F312L; S2P, M71C, L114P, T348A; S2P, M71C, L114P, L380F; S2P, M71C, L114P, T394M; S2P, M71C, L114P, F396Y; S2P, M71C, L114P, R400C; S2P, M71C, L114P, T413A; S2P, M71C, L114P, E423D; S2P, M71C, L114P, L453P; S2P, M71C, L114P, F458S; S2P, M71C, L114P, E461G; S2P, M71C, L114P, F465C; S2P, M71C, L114P, N467T; S2P, M71C, L114P, N470S; S2P, M71C, L114P, A476T; S2P, M71C, L114P, Q494R; S2P, M71C, L114P, T496R; S2P, M71C, L114P, G504S; S2P, M71V, S130L, K145M; S2P, M71V, S130L, N166S; S2P, M71V, S130L, F171I; S2P, M71V, S130L, D203A; S2P, M71V, S130L, D203G; S2P, M71V, S130L, T213A; S2P, M71V, S130L, V225I; S2P, M71V, S130L, K237E; S2P, M71V, S130L, V256I; S2P, M71V, S130L, T258A; S2P, M71V, S130L, D264G; S2P, M71V, S130L, T283A; S2P, M71V, S130L, L289P; S2P, M71V, S130L, F312L; S2P, M71V, S130L, T348A; S2P, M71V, S130L, L380F; S2P, M71V, S130L,

T394M; S2P, M71V, S130L, F396Y; S2P, M71V, S130L, R400C; S2P, M71V, S130L, T413A; S2P, M71V, S130L, E423D; S2P, M71V, S130L, L453P; S2P, M71V, S130L, F458S; S2P, M71V, S130L, E461G; S2P, M71V, S130L, F465C; S2P, M71V, S130L, N467T; S2P, M71V, S130L, N470S; S2P, M71V, S130L, A476T; S2P, M71V, S130L, Q494R; S2P, M71V, S130L, T496R; S2P, M71V, S130L, G504S; S2P, M71T, S130L, K145M; S2P, M71T, S130L, N166S; S2P, M71T, S130L, F171I; S2P, M71T, S130L, D203A; S2P, M71T, S130L, D203G; S2P, M71T, S130L, T213A; S2P, M71T, S130L, V225I; S2P, M71T, S130L, K237E; S2P, M71T, S130L, V256I; S2P, M71T, S130L, T258A; S2P, M71T, S130L, D264G; S2P, M71T, S130L, T283A; S2P, M71T, S130L, L289P; S2P, M71T, S130L, F312L; S2P, M71T, S130L, T348A; S2P, M71T, S130L, L380F; S2P, M71T, S130L, T394M; S2P, M71T, S130L, F396Y; S2P, M71T, S130L, R400C; S2P, M71T, S130L, T413A; S2P, M71T, S130L, E423D; S2P, M71T, S130L, L453P; S2P, M71T, S130L, F458S; S2P, M71T, S130L, E461G; S2P, M71T, S130L, F465C; S2P, M71T, S130L, N467T; S2P, M71T, S130L, N470S; S2P, M71T, S130L, A476T; S2P, M71T, S130L, Q494R; S2P, M71T, S130L, T496R; S2P, M71T, S130L, G504S; S2P, M71A, S130L, K145M; S2P, M71A, S130L, N166S; S2P, M71A, S130L, F171I; S2P, M71A, S130L, D203A; S2P, M71A, S130L, D203G; S2P, M71A, S130L, T213A; S2P, M71A, S130L, V225I; S2P, M71A, S130L, K237E; S2P, M71A, S130L, V256I; S2P, M71A, S130L, T258A; S2P, M71A, S130L, D264G; S2P, M71A, S130L, T283A; S2P, M71A, S130L, L289P; S2P, M71A, S130L, F312L; S2P, M71A, S130L, T348A; S2P, M71A, S130L, L380F; S2P, M71A, S130L, T394M; S2P, M71A, S130L, F396Y; S2P, M71A, S130L, R400C; S2P, M71A, S130L, T413A; S2P, M71A, S130L, E423D; S2P, M71A, S130L, L453P; S2P, M71A, S130L, F458S; S2P, M71A, S130L, E461G; S2P, M71A, S130L, F465C; S2P, M71A, S130L, N467T; S2P, M71A, S130L, N470S; S2P, M71A, S130L, A476T; S2P, M71A, S130L, Q494R; S2P, M71A, S130L, T496R; S2P, M71A, S130L, G504S; S2P, M71C, S130L, K145M; S2P, M71C, S130L, N166S; S2P, M71C, S130L, F171I; S2P, M71C, S130L, D203A; S2P, M71C, S130L, D203G; S2P, M71C, S130L, T213A; S2P, M71C, S130L, V225I; S2P, M71C, S130L, K237E; S2P, M71C, S130L, V256I; S2P, M71C, S130L, T258A; S2P, M71C, S130L, D264G; S2P, M71C, S130L, T283A; S2P, M71C, S130L, L289P; S2P, M71C, S130L, F312L; S2P, M71C, S130L, T348A; S2P, M71C, S130L, L380F; S2P, M71C, S130L, T394M; S2P, M71C, S130L, F396Y; S2P, M71C, S130L, R400C; S2P, M71C, S130L, T413A; S2P, M71C, S130L, E423D; S2P, M71C, S130L, L453P; S2P, M71C, S130L, F458S; S2P, M71C, S130L, E461G; S2P, M71C, S130L, F465C; S2P, M71C, S130L, N467T; S2P, M71C, S130L, N470S; S2P, M71C, S130L, A476T; S2P, M71C, S130L, Q494R; S2P, M71C, S130L, T496R; S2P, M71C, S130L, G504S; S2P, M71V, K145M, N166S; S2P, M71V, K145M, F171I; S2P, M71V, K145M, D203A; S2P, M71V, K145M, D203G; S2P, M71V, K145M, T213A; S2P, M71V, K145M, V225I; S2P, M71V, K145M, K237E; S2P, M71V, K145M, V256I; S2P, M71V, K145M, T258A; S2P, M71V, K145M, D264G; S2P, M71V, K145M, T283A; S2P, M71V, K145M, L289P; S2P, M71V, K145M, F312L; S2P, M71V, K145M, T348A; S2P, M71V, K145M, L380F; S2P, M71V, K145M, T394M; S2P, M71V, K145M, F396Y; S2P, M71V, K145M, R400C; S2P, M71V, K145M, T413A; S2P, M71V, K145M, E423D; S2P, M71V, K145M, L453P; S2P, M71V, K145M, F458S; S2P, M71V, K145M, E461G; S2P, M71V, K145M, F465C; S2P, M71V, K145M, N467T; S2P, M71V, K145M, N470S; S2P, M71V, K145M, A476T; S2P, M71V, K145M, Q494R; S2P, M71V, K145M, T496R; S2P, M71V, K145M, G504S; S2P, M71T, K145M, N166S; S2P, M71T, K145M, F171I; S2P, M71T, K145M, D203A; S2P, M71T, K145M, D203G; S2P, M71T, K145M, T213A; S2P, M71T, K145M, V225I; S2P, M71T, K145M, K237E; S2P, M71T, K145M, V256I; S2P, M71T, K145M, T258A; S2P, M71T, K145M, D264G; S2P, M71T, K145M, T283A; S2P, M71T, K145M, L289P; S2P, M71T, K145M, F312L; S2P, M71T, K145M, T348A; S2P, M71T, K145M, L380F; S2P, M71T, K145M, T394M; S2P, M71T, K145M, F396Y; S2P, M71T, K145M, R400C; S2P, M71T, K145M, T413A; S2P, M71T, K145M, E423D; S2P, M71T, K145M, L453P; S2P, M71T, K145M, F458S; S2P, M71T, K145M, E461G; S2P, M71T, K145M, F465C; S2P, M71T, K145M, N467T; S2P, M71T, K145M, N470S; S2P, M71T, K145M, A476T; S2P, M71T, K145M, Q494R; S2P, M71T, K145M, T496R; S2P, M71T, K145M, G504S; S2P, M71A, K145M, N166S; S2P, M71A, K145M, F171I; S2P, M71A, K145M, D203A; S2P, M71A, K145M, D203G; S2P, M71A, K145M, T213A; S2P, M71A, K145M, V225I; S2P, M71A, K145M, K237E; S2P, M71A, K145M, V256I; S2P, M71A, K145M, T258A; S2P, M71A, K145M, D264G; S2P, M71A, K145M, T283A; S2P, M71A, K145M, L289P; S2P, M71A, K145M, F312L; S2P, M71A, K145M, T348A; S2P, M71A, K145M, L380F; S2P, M71A, K145M, T394M; S2P, M71A, K145M, F396Y; S2P, M71A, K145M, R400C; S2P, M71A, K145M, T413A; S2P, M71A, K145M, E423D; S2P, M71A, K145M, L453P; S2P, M71A, K145M, F458S; S2P, M71A, K145M, E461G; S2P, M71A, K145M, F465C; S2P, M71A, K145M, N467T; S2P, M71A, K145M, N470S; S2P, M71A, K145M, A476T; S2P, M71A, K145M, Q494R; S2P, M71A, K145M, T496R; S2P, M71A, K145M, G504S; S2P, M71C, K145M, N166S; S2P, M71C, K145M, F171I; S2P, M71C, K145M, D203A; S2P, M71C, K145M, D203G; S2P, M71C, K145M, T213A; S2P, M71C, K145M, V225I, S2P, M71C, K145M, K237E, S2P, M71C, K145M, V256I, S2P, M71C, K145M, T258A, S2P, M71C, K145M, D264G, S2P, M71C, K145M, T283A; S2P, M71C, K145M, L289P; S2P, M71C, K145M, F312L; S2P, M71C, K145M, T348A; S2P, M71C, K145M, L380F; S2P, M71C, K145M, T394M; S2P, M71C, K145M, F396Y; S2P, M71C, K145M, R400C; S2P, M71C, K145M, T413A; S2P, M71C, K145M, E423D; S2P, M71C, K145M, L453P; S2P, M71C, K145M, F458S; S2P, M71C, K145M, E461G; S2P, M71C, K145M, F465C; S2P, M71C, K145M, N467T; S2P, M71C, K145M, N470S; S2P, M71C, K145M, A476T; S2P, M71C, K145M, Q494R; S2P, M71C, K145M, T496R; S2P, M71C, K145M, G504S; S2P, M71V, D203A, N166S; S2P, M71V, D203A, F171I; S2P, M71V, D203A, T213A; S2P, M71V, D203A, V225I; S2P, M71V, D203A, K237E; S2P, M71V, D203A, V256I; S2P, M71V, D203A, T258A; S2P, M71V, D203A, D264G; S2P, M71V, D203A, T283A; S2P, M71V, D203A, L289P; S2P, M71V, D203A, F312L; S2P, M71V, D203A, T348A; S2P, M71V, D203A, L380F; S2P, M71V, D203A, T394M; S2P, M71V, D203A, F396Y; S2P, M71V, D203A, R400C; S2P, M71V, D203A, T413A; S2P, M71V, D203A, E423D; S2P, M71V, D203A, L453P; S2P, M71V, D203A, F458S; S2P, M71V, D203A, E461G; S2P, M71V, D203A, F465C; S2P, M71V, D203A, N467T; S2P, M71V, D203A, N470S; S2P, M71V, D203A, A476T; S2P, M71V, D203A, Q494R; S2P, M71V, D203A, T496R; S2P, M71V, D203A, G504S; S2P, M71T, D203A, N166S; S2P, M71T, D203A, F171I; S2P, M71T, D203A, T213A; S2P, M71T, D203A, V225I; S2P, M71T, D203A, K237E; S2P, M71T, D203A, V256I; S2P, M71T, D203A, T258A; S2P, M71T, D203A, D264G; S2P, M71T, D203A, T283A; S2P, M71T, D203A, L289P; S2P, M71T, D203A, F312L; S2P, M71T, D203A, T348A; S2P, M71T, D203A,

L380F; S2P, M71T, D203A, T394M; S2P, M71T, D203A, F396Y; S2P, M71T, D203A, R400C; S2P, M71T, D203A, T413A; S2P, M71T, D203A, E423D; S2P, M71T, D203A, L453P; S2P, M71T, D203A, F458S; S2P, M71T, D203A, E461G; S2P, M71T, D203A, F465C; S2P, M71T, D203A, N467T; S2P, M71T, D203A, N470S; S2P, M71T, D203A, A476T; S2P, M71T, D203A, Q494R; S2P, M71T, D203A, T496R; S2P, M71T, D203A, G504S; S2P, M71A, D203A, N166S; S2P, M71A, D203A, T213A; S2P, M71A, D203A, V225I; S2P, M71A, D203A, K237E; S2P, M71A, D203A, V256I; S2P, M71A, D203A, T258A; S2P, M71A, D203A, D264G; S2P, M71A, D203A, T283A; S2P, M71A, D203A, L289P; S2P, M71A, D203A, F312L; S2P, M71A, D203A, T348A; S2P, M71A, D203A, L380F; S2P, M71A, D203A, T394M; S2P, M71A, D203A, F396Y; S2P, M71A, D203A, R400C; S2P, M71A, D203A, T413A; S2P, M71A, D203A, E423D; S2P, M71A, D203A, L453P; S2P, M71A, D203A, F458S; S2P, M71A, D203A, E461G; S2P, M71A, D203A, F465C; S2P, M71A, D203A, N467T; S2P, M71A, D203A, N470S; S2P, M71A, D203A, A476T; S2P, M71A, D203A, Q494R; S2P, M71A, D203A, T496R; S2P, M71A, D203A, G504S; S2P, M71C, D203A, N166S; S2P, M71C, D203A, F171I; S2P, M71C, D203A, T213A; S2P, M71C, D203A, V225I; S2P, M71C, D203A, K237E; S2P, M71C, D203A, V256I; S2P, M71C, D203A, T258A; S2P, M71C, D203A, D264G; S2P, M71C, D203A, T283A; S2P, M71C, D203A, L289P; S2P, M71C, D203A, F312L; S2P, M71C, D203A, T348A; 2P, M71C, D203A, L380F; S2P, M71C, D203A, T394M; S2P, M71C, D203A, F396Y; S2P, M71C, D203A, R400C; S2P, M71C, D203A, T413A; S2P, M71C, D203A, E423D; S2P, M71C, D203A, L453P; S2P, M71C, D203A, F458S; S2P, M71C, D203A, E461G; S2P, M71C, D203A, F465C; S2P, M71C, D203A, N467T; S2P, M71C, D203A, N470S; S2P, M71C, D203A, A476T; S2P, M71C, D203A, Q494R; S2P, M71C, D203A, T496R; S2P, M71C, D203A, G504S; S2P, M71V, D203C, N166S; S2P, M71V, D203C, F171I; S2P, M71V, D203C, T213A; S2P, M71V, D203C, V225I; S2P, M71V, D203C, K237E; S2P, M71V, D203C, V256I; S2P, M71V, D203C, T258A; S2P, M71V, D203C, D264G; S2P, M71V, D203C, T283A; S2P, M71V, D203C, L289P; S2P, M71V, D203C, F312L; S2P, M71V, D203C, T348A; S2P, M71V, D203C, L380F; S2P, M71V, D203C, T394M; S2P, M71V, D203C, F396Y; S2P, M71V, D203C, R400C; S2P, M71V, D203C, T413A; S2P, M71V, D203C, E423D; S2P, M71V, D203C, L453P; S2P, M71V, D203C, F458S; 2P, M71V, D203C, E461G; S2P, M71V, D203C, F465C; S2P, M71V, D203C, N467T; S2P, M71V, D203C, N470S; S2P, M71V, D203C, A476T; S2P, M71V, D203C, Q494R; S2P, M71V, D203C, T496R; S2P, M71V, D203C, G504S; S2P, M71T, D203C, N166S; S2P, M71T, D203C, F171I; S2P, M71T, D203C, T213A; S2P, M71T, D203C, V225I; S2P, M71T, D203C, K237E; S2P, M71T, D203C, V256I; S2P, M71T, D203C, T258A; S2P, M71T, D203C, D264G; S2P, M71T, D203C, T283A; S2P, M71T, D203C, L289P; S2P, M71T, D203C, F312L; S2P, M71T, D203C, T348A; S2P, M71T, D203C, L380F; S2P, M71T, D203C, T394M; S2P, M71T, D203C, F396Y; S2P, M71T, D203C, R400C; S2P, M71T, D203C, T413A; S2P, M71T, D203C, E423D; S2P, M71T, D203C, L453P; S2P, M71T, D203C, F458S; S2P, M71T, D203C, E461G; S2P, M71T, D203C, F465C; S2P, M71T, D203C, N467T; S2P, M71T, D203C, N470S; S2P, M71T, D203C, A476T; S2P, M71T, D203C, Q494R; S2P, M71T, D203C, T496R; S2P, M71T, D203C, G504S; S2P, M71A, D203C, N166S; S2P, M71A, D203C, T213A; S2P, M71A, D203C, V225I; S2P, M71A, D203C, K237E; S2P, M71A, D203C, V256I; S2P, M71A, D203C, T258A; S2P, M71A, D203C, D264G; S2P, M71A, D203C, T283A; S2P, M71A, D203C, L289P; S2P, M71A, D203C, F312L; S2P, M71A, D203C, T348A; S2P, M71A, D203C, L380F; S2P, M71A, D203C, T394M; S2P, M71A, D203C, F396Y; S2P, M71A, D203C, R400C; S2P, M71A, D203C, T413A; S2P, M71A, D203C, E423D; S2P, M71A, D203C, L453P; S2P, M71A, D203C, F458S; S2P, M71A, D203C, E461G; S2P, M71A, D203C, F465C; S2P, M71A, D203C, N467T; S2P, M71A, D203C, N470S; S2P, M71A, D203C, A476T; S2P, M71A, D203C, Q494R; S2P, M71A, D203C, T496R; S2P, M71A, D203C, G504S; S2P, M71C, D203C, N166S; S2P, M71C, D203C, F171I; S2P, M71C, D203C, T213A; S2P, M71C, D203C, V225I; S2P, M71C, D203C, K237E; S2P, M71C, D203C, V256I; S2P, M71C, D203C, T258A; S2P, M71C, D203C, D264G; S2P, M71C, D203C, T283A; S2P, M71C, D203C, L289P; S2P, M71C, D203C, F312L; S2P, M71C, D203C, T348A; S2P, M71C, D203C, L380F; S2P, M71C, D203C, T394M; S2P, M71C, D203C, F396Y; S2P, M71C, D203C, R400C; S2P, M71C, D203C, T413A; S2P, M71C, D203C, E423D; S2P, M71C, D203C, L453P; S2P, M71C, D203C, F458S; S2P, M71C, D203C, E461G; S2P, M71C, D203C, F465C; S2P, M71C, D203C, N467T; S2P, M71C, D203C, N470S; S2P, M71C, D203C, A476T; S2P, M71C, D203C, Q494R; S2P, M71C, D203C, T496R; S2P, M71C, D203C, G504S; S2P, M71V, T213A, V225I; S2P, M71V, T213A, K237E; S2P, M71V, T213A, V256I; S2P, M71V, T213A, T258A; S2P, M71V, T213A, D264G; S2P, M71V, T213A, T283A; S2P, M71V, T213A, L289P; S2P, M71V, T213A, F312L; S2P, M71V, T213A, T348A; S2P, M71V, T213A, L380F; S2P, M71V, T213A, T394M; S2P, M71V, T213A, F396Y; S2P, M71V, T213A, R400C; S2P, M71V, T213A, T413A; S2P, M71V, T213A, E423D; S2P, M71V, T213A, L453P; S2P, M71V, T213A, F458S; S2P, M71V, T213A, E461G; S2P, M71V, T213A, F465C; S2P, M71V, T213A, N467T; S2P, M71V, T213A, N470S; S2P, M71V, T213A, A476T; S2P, M71V, T213A, Q494R; S2P, M71V, T213A, T496R; S2P, M71V, T213A, G504S; S2P, M71T, T213A, N166S; S2P, M71T, T213A, F171I; S2P, M71T, T213A, V225I; S2P, M71T, T213A, K237E; S2P, M71T, T213A, V256I; S2P, M71T, T213A, T258A; S2P, M71T, T213A, D264G; S2P, M71T, T213A, T283A; S2P, M71T, T213A, L289P; S2P, M71T, T213A, F312L; S2P, M71T, T213A, T348A; S2P, M71T, T213A, L380F; S2P, M71T, T213A, T394M; S2P, M71T, T213A, F396Y; S2P, M71T, T213A, R400C; S2P, M71T, T213A, T413A; S2P, M71T, T213A, E423D; S2P, M71T, T213A, L453P; S2P, M71T, T213A, F458S; S2P, M71T, T213A, E461G; S2P, M71T, T213A, F465C; S2P, M71T, T213A, N467T; S2P, M71T, T213A, N470S; S2P, M71T, T213A, A476T; S2P, M71T, T213A, Q494R; S2P, M71T, T213A, T496R; S2P, M71T, T213A, G504S; S2P, M71A, T213A, N166S; S2P, M71A, T213A, V225I; S2P, M71A, T213A, K237E; S2P, M71A, T213A, V256I; S2P, M71A, T213A, T258A; S2P, M71A, T213A, D264G; S2P, M71A, T213A, T283A; S2P, M71A, T213A, L289P; S2P, M71A, T213A, F312L; S2P, M71A, T213A, T348A; S2P, M71A, T213A, L380F; S2P, M71A, T213A, T394M; S2P, M71A, T213A, F396Y; S2P, M71A, T213A, R400C; S2P, M71A, T213A, T413A; S2P, M71A, T213A, E423D; S2P, M71A, T213A, L453P; S2P, M71A, T213A, F458S; S2P, M71A, T213A, E461G; S2P, M71A, T213A, F465C; S2P, M71A, T213A, N467T; S2P, M71A, T213A, N470S; S2P, M71A, T213A, A476T; S2P, M71A, T213A, Q494R; S2P, M71A, T213A, T496R; S2P, M71A, T213A, G504S; S2P, M71C, T213A, N166S; S2P, M71C, T213A, F171I; S2P, M71C, T213A, V225I; S2P, M71C, T213A, K237E; S2P, M71C, T213A, V256I; S2P, M71C, T213A, T258A; S2P, M71C, T213A, D264G; S2P, M71C, T213A, T283A; S2P, M71C, T213A,

L289P; S2P, M71C, T213A, F312L; S2P, M71C, T213A, T348A; S2P, M71C, T213A, L380F; S2P, M71C, T213A, T394M; S2P, M71C, T213A, F396Y; S2P, M71C, T213A, R400C; S2P, M71C, T213A, T413A; S2P, M71C, T213A, E423D; S2P, M71C, T213A, L453P; S2P, M71C, T213A, F458S; S2P, M71C, T213A, E461G; S2P, M71C, T213A, F465C; S2P, M71C, T213A, N467T; S2P, M71C, T213A, N470S; S2P, M71C, T213A, A476T; S2P, M71C, T213A, Q494R; S2P, M71C, T213A, T496R; S2P, M71C, T213A, G504S; S2P, M71V, V225I, K237E; S2P, M71V, V225I, V256I; S2P, M71V, V225I, T258A; S2P, M71V, V225I, D264G; S2P, M71V, V225I, T283A; S2P, M71V, V225I, L289P; S2P, M71V, V225I, F312L; S2P, M71V, V225I, T348A; S2P, M71V, V225I, L380F; S2P, M71V, V225I, T394M; S2P, M71V, V225I, F396Y; S2P, M71V, V225I, R400C; S2P, M71V, V225I, T413A; S2P, M71V, V225I, E423D; S2P, M71V, V225I, L453P; S2P, M71V, V225I, F458S; S2P, M71V, V225I, E461G; S2P, M71V, V225I, F465C; S2P, M71V, V225I, N467T; S2P, M71V, V225I, N470S; S2P, M71V, V225I, A476T; S2P, M71V, V225I, Q494R; S2P, M71V, V225I, T496R; S2P, M71V, V225I, G504S; S2P, M71T, V225I, N166S; S2P, M71T, V225I, F171I; S2P, M71T, V225I, K237E; S2P, M71T, V225I, V256I; S2P, M71T, V225I, T258A; S2P, M71T, V225I, D264G; S2P, M71T, V225I, T283A; S2P, M71T, V225I, L289P; S2P, M71T, V225I, F312L; S2P, M71T, V225I, T348A; S2P, M71T, V225I, L380F; S2P, M71T, V225I, T394M; S2P, M71T, V225I, F396Y; S2P, M71T, V225I, R400C; S2P, M71T, V225I, T413A; S2P, M71T, V225I, E423D; S2P, M71T, V225I, L453P; S2P, M71T, V225I, F458S; S2P, M71T, V225I, E461G; S2P, M71T, V225I, F465C; S2P, M71T, V225I, N467T; S2P, M71T, V225I, N470S; S2P, M71T, V225I, A476T; S2P, M71T, V225I, Q494R; S2P, M71T, V225I, T496R; S2P, M71T, V225I, G504S; S2P, M71A, V225I, N166S; S2P, M71A, V225I, K237E; S2P, M71A, V225I, V256I; S2P, M71A, V225I, T258A; S2P, M71A, V225I, D264G; S2P, M71A, V225I, T283A; S2P, M71A, V225I, L289P; S2P, M71A, V225I, F312L; S2P, M71A, V225I, T348A; S2P, M71A, V225I, L380F; S2P, M71A, V225I, T394M; S2P, M71A, V225I, F396Y; S2P, M71A, V225I, R400C; S2P, M71A, V225I, T413A; S2P, M71A, V225I, E423D; S2P, M71A, V225I, L453P; S2P, M71A, V225I, F458S; S2P, M71A, V225I, E461G; S2P, M71A, V225I, F465C; S2P, M71A, V225I, N467T; S2P, M71A, V225I, N470S; S2P, M71A, V225I, A476T; S2P, M71A, V225I, Q494R; S2P, M71A, V225I, T496R; S2P, M71A, V225I, G504S; S2P, M71C, V225I, N166S; S2P, M71C, V225I, F171I; S2P, M71C, V225I, K237E; S2P, M71C, V225I, V256I; S2P, M71C, V225I, T258A; S2P, M71C, V225I, D264G; S2P, M71C, V225I, T283A; S2P, M71C, V225I, L289P; S2P, M71C, V225I, F312L; S2P, M71C, V225I, T348A; S2P, M71C, V225I, L380F; S2P, M71C, V225I, T394M; S2P, M71C, V225I, F396Y; S2P, M71C, V225I, R400C; S2P, M71C, V225I, T413A; S2P, M71C, V225I, E423D; S2P, M71C, V225I, L453P; S2P, M71C, V225I, F458S; S2P, M71C, V225I, E461G; S2P, M71C, V225I, F465C; S2P, M71C, V225I, N467T; S2P, M71C, V225I, N470S; S2P, M71C, V225I, A476T; S2P, M71C, V225I, Q494R; S2P, M71C, V225I, T496R; S2P, M71C, V225I, G504S; S2P, M71V, K237E, V256I; S2P, M71V, K237E, T258A; S2P, M71V, K237E, D264G; S2P, M71V, K237E, T283A; S2P, M71V, K237E, L289P; S2P, M71V, K237E, F312L; S2P, M71V, K237E, T348A; S2P, M71V, K237E, L380F; S2P, M71V, K237E, T394M; S2P, M71V, K237E, F396Y; S2P, M71V, K237E, R400C; S2P, M71V, K237E, T413A; S2P, M71V, K237E, E423D; S2P, M71V, K237E, L453P; S2P, M71V, K237E, F458S; S2P, M71V, K237E, E461G; S2P, M71V, K237E, F465C; S2P, M71V, K237E, N467T; S2P, M71V, K237E, N470S; S2P, M71V, K237E, A476T; S2P, M71V, K237E, Q494R; S2P, M71V, K237E, T496R; S2P, M71V, K237E, G504S; S2P, M71T, K237E, V256I; S2P, M71T, K237E, T258A; S2P, M71T, K237E, D264G; S2P, M71T, K237E, T283A; S2P, M71T, K237E, L289P; S2P, M71T, K237E, F312L; S2P, M71T, K237E, T348A; S2P, M71T, K237E, L380F; S2P, M71T, K237E, T394M; S2P, M71T, K237E, F396Y; S2P, M71T, K237E, R400C; S2P, M71T, K237E, T413A; S2P, M71T, K237E, E423D; S2P, M71T, K237E, L453P; S2P, M71T, K237E, F458S; S2P, M71T, K237E, E461G; S2P, M71T, K237E, F465C; S2P, M71T, K237E, N467T; S2P, M71T, K237E, N470S; S2P, M71T, K237E, A476T; S2P, M71T, K237E, Q494R; S2P, M71T, K237E, T496R; S2P, M71T, K237E, G504S; S2P, M71A, K237E, V256I; S2P, M71A, K237E, T258A; S2P, M71A, K237E, D264G; S2P, M71A, K237E, T283A; S2P, M71A, K237E, L289P; S2P, M71A, K237E, F312L; S2P, M71A, K237E, T348A; S2P, M71A, K237E, L380F; S2P, M71A, K237E, T394M; S2P, M71A, K237E, F396Y; S2P, M71A, K237E, R400C; S2P, M71A, K237E, T413A; S2P, M71A, K237E, E423D; S2P, M71A, K237E, L453P; S2P, M71A, K237E, F458S; S2P, M71A, K237E, E461G; S2P, M71A, K237E, F465C; S2P, M71A, K237E, N467T; S2P, M71A, K237E, N470S; S2P, M71A, K237E, A476T; S2P, M71A, K237E, Q494R; S2P, M71A, K237E, T496R; S2P, M71A, K237E, G504S; S2P, M71C, K237E, V256I; S2P, M71C, K237E, T258A; S2P, M71C, K237E, D264G; S2P, M71C, K237E, T283A; S2P, M71C, K237E, L289P; S2P, M71C, K237E, F312L; S2P, M71C, K237E, T348A; S2P, M71C, K237E, L380F; S2P, M71C, K237E, T394M; S2P, M71C, K237E, F396Y; S2P, M71C, K237E, R400C; S2P, M71C, K237E, T413A; S2P, M71C, K237E, E423D; S2P, M71C, K237E, L453P; S2P, M71C, K237E, F458S; S2P, M71C, K237E, E461G; S2P, M71C, K237E, F465C; S2P, M71C, K237E, N467T; S2P, M71C, K237E, N470S; S2P, M71C, K237E, A476T; S2P, M71C, K237E, Q494R; S2P, M71C, K237E, T496R; S2P, M71C, K237E, G504S; S2P, M71V, V256I, T258A; S2P, M71V, V256I, D264G; S2P, M71V, V256I, T283A; S2P, M71V, V256I, L289P; S2P, M71V, V256I, F312L; S2P, M71V, V256I, T348A; S2P, M71V, V256I, L380F; S2P, M71V, V256I, T394M; S2P, M71V, V256I, F396Y; S2P, M71V, V256I, R400C; S2P, M71V, V256I, T413A; S2P, M71V, V256I, E423D; S2P, M71V, V256I, L453P; S2P, M71V, V256I, F458S; S2P, M71V, V256I, E461G; S2P, M71V, V256I, F465C; S2P, M71V, V256I, N467T; S2P, M71V, V256I, N470S; S2P, M71V, V256I, A476T; S2P, M71V, V256I, Q494R; S2P, M71V, V256I, T496R; S2P, M71V, V256I, G504S; S2P, M71T, V256I, T258A; S2P, M71T, V256I, D264G; S2P, M71T, V256I, T283A; S2P, M71T, V256I, L289P; S2P, M71T, V256I, F312L; S2P, M71T, V256I, T348A; S2P, M71T, V256I, L380F; S2P, M71T, V256I, T394M; S2P, M71T, V256I, F396Y; S2P, M71T, V256I, R400C; S2P, M71T, V256I, T413A; S2P, M71T, V256I, E423D; S2P, M71T, V256I, L453P; S2P, M71T, V256I, F458S; S2P, M71T, V256I, E461G; S2P, M71T, V256I, F465C; S2P, M71T, V256I, N467T; S2P, M71T, V256I, N470S; S2P, M71T, V256I, A476T; S2P, M71T, V256I, Q494R; S2P, M71T, V256I, T496R; S2P, M71T, V256I, G504S; S2P, M71A, V256I, T258A; S2P, M71A, V256I, D264G; S2P, M71A, V256I, T283A; S2P, M71A, V256I, L289P; S2P, M71A, V256I, F312L; S2P, M71A, V256I, T348A; S2P, M71A, V256I, L380F; S2P, M71A, V256I, T394M; S2P, M71A, V256I, F396Y; S2P, M71A, V256I, R400C; S2P, M71A, V256I, T413A; S2P, M71A, V256I, E423D; S2P, M71A, V256I,

L453P; S2P, M71A, V256I, F458S; S2P, M71A, V256I, E461G; S2P, M71A, V256I, F465C; S2P, M71A, V256I, N467T; S2P, M71A, V256I, N470S; S2P, M71A, V256I, A476T; S2P, M71A, V256I, Q494R; S2P, M71A, V256I, T496R; S2P, M71A, V256I, G504S; S2P, M71C, V256I, T258A; S2P, M71C, V256I, D264G; S2P, M71C, V256I, T283A; S2P, M71C, V256I, L289P; S2P, M71C, V256I, F312L; S2P, M71C, V256I, T348A; S2P, M71C, V256I, L380F; S2P, M71C, V256I, T394M; S2P, M71C, V256I, F396Y; S2P, M71C, V256I, R400C; S2P, M71C, V256I, T413A; S2P, M71C, V256I, E423D; S2P, M71C, V256I, L453P; S2P, M71C, V256I, F458S; S2P, M71C, V256I, E461G; S2P, M71C, V256I, F465C; S2P, M71C, V256I, N467T; S2P, M71C, V256I, N470S; S2P, M71C, V256I, A476T; S2P, M71C, V256I, Q494R; S2P, M71C, V256I, T496R; S2P, M71C, V256I, G504S; S2P, M71V, T258A, D264G; S2P, M71V, T258A, T283A; S2P, M71V, T258A, L289P; S2P, M71V, T258A, F312L; S2P, M71V, T258A, T348A; S2P, M71V, T258A, L380F; S2P, M71V, T258A, T394M; S2P, M71V, T258A, F396Y; S2P, M71V, T258A, R400C; S2P, M71V, T258A, T413A; S2P, M71V, T258A, E423D; S2P, M71V, T258A, L453P; S2P, M71V, T258A, F458S; S2P, M71V, T258A, E461G; S2P, M71V, T258A, F465C; S2P, M71V, T258A, N467T; S2P, M71V, T258A, N470S; S2P, M71V, T258A, A476T; S2P, M71V, T258A, Q494R; S2P, M71V, T258A, T496R; S2P, M71V, T258A, G504S; S2P, M71T, T258A, D264G; S2P, M71T, T258A, T283A; S2P, M71T, T258A, L289P; S2P, M71T, T258A, F312L; S2P, M71T, T258A, T348A; S2P, M71T, T258A, L380F; S2P, M71T, T258A, T394M; S2P, M71T, T258A, F396Y; S2P, M71T, T258A, R400C; S2P, M71T, T258A, T413A; S2P, M71T, T258A, E423D; S2P, M71T, T258A, L453P; S2P, M71T, T258A, F458S; S2P, M71T, T258A, E461G; S2P, M71T, T258A, F465C; S2P, M71T, T258A, N467T; S2P, M71T, T258A, N470S; S2P, M71T, T258A, A476T; S2P, M71T, T258A, Q494R; S2P, M71T, T258A, T496R; S2P, M71T, T258A, G504S; S2P, M71A, T258A, D264G; S2P, M71A, T258A, T283A; S2P, M71A, T258A, L289P; S2P, M71A, T258A, F312L; S2P, M71A, T258A, T348A; S2P, M71A, T258A, L380F; S2P, M71A, T258A, T394M; S2P, M71A, T258A, F396Y; S2P, M71A, T258A, R400C; S2P, M71A, T258A, T413A; S2P, M71A, T258A, E423D; S2P, M71A, T258A, L453P; S2P, M71A, T258A, F458S; S2P, M71A, T258A, E461G; S2P, M71A, T258A, F465C; S2P, M71A, T258A, N467T; S2P, M71A, T258A, N470S; S2P, M71A, T258A, A476T; S2P, M71A, T258A, Q494R; S2P, M71A, T258A, T496R; S2P, M71A, T258A, G504S; S2P, M71C, T258A, D264G; S2P, M71C, T258A, T283A; S2P, M71C, T258A, L289P; S2P, M71C, T258A, F312L; S2P, M71C, T258A, T348A; S2P, M71C, T258A, L380F; S2P, M71C, T258A, T394M; S2P, M71C, T258A, F396Y; S2P, M71C, T258A, R400C; S2P, M71C, T258A, T413A; S2P, M71C, T258A, E423D; S2P, M71C, T258A, L453P; S2P, M71C, T258A, F458S; S2P, M71C, T258A, E461G; S2P, M71C, T258A, F465C; S2P, M71C, T258A, N467T; S2P, M71C, T258A, N470S; S2P, M71C, T258A, A476T; S2P, M71C, T258A, Q494R; S2P, M71C, T258A, T496R; S2P, M71C, T258A, G504S; S2P, M71V, D264G, T283A; S2P, M71V, D264G, L289P; S2P, M71V, D264G, F312L; S2P, M71V, D264G, T348A; S2P, M71V, D264G, L380F; S2P, M71V, D264G, T394M; S2P, M71V, D264G, F396Y; S2P, M71V, D264G, R400C; S2P, M71V, D264G, T413A; S2P, M71V, D264G, E423D; S2P, M71V, D264G, L453P; S2P, M71V, D264G, F458S; S2P, M71V, D264G, E461G; S2P, M71V, D264G, F465C; S2P, M71V, D264G, N467T; S2P, M71V, D264G, N470S; S2P, M71V, D264G, A476T; S2P, M71V, D264G, Q494R; S2P, M71V, D264G, T496R; S2P, M71V, D264G, G504S; S2P, M71T, D264G, T283A; S2P, M71T, D264G, L289P; S2P, M71T, D264G, F312L; S2P, M71T, D264G, T348A; S2P, M71T, D264G, L380F; S2P, M71T, D264G, T394M; S2P, M71T, D264G, F396Y; S2P, M71T, D264G, R400C; S2P, M71T, D264G, T413A; S2P, M71T, D264G, E423D; S2P, M71T, D264G, L453P; S2P, M71T, D264G, F458S; S2P, M71T, D264G, E461G; S2P, M71T, D264G, F465C; S2P, M71T, D264G, N467T; S2P, M71T, D264G, N470S; S2P, M71T, D264G, A476T; S2P, M71T, D264G, Q494R; S2P, M71T, D264G, T496R; S2P, M71T, D264G, G504S; S2P, M71A, D264G, T283A; S2P, M71A, D264G, L289P; S2P, M71A, D264G, F312L; S2P, M71A, D264G, T348A; S2P, M71A, D264G, L380F; S2P, M71A, D264G, T394M; S2P, M71A, D264G, F396Y; S2P, M71A, D264G, R400C; S2P, M71A, D264G, T413A; S2P, M71A, D264G, E423D; S2P, M71A, D264G, L453P; S2P, M71A, D264G, F458S; S2P, M71A, D264G, E461G; S2P, M71A, D264G, F465C; S2P, M71A, D264G, N467T; S2P, M71A, D264G, N470S; S2P, M71A, D264G, A476T; S2P, M71A, D264G, Q494R; S2P, M71A, D264G, T496R; S2P, M71A, D264G, G504S; S2P, M71C, D264G, T283A; S2P, M71C, D264G, L289P; S2P, M71C, D264G, F312L; S2P, M71C, D264G, T348A; S2P, M71C, D264G, L380F; S2P, M71C, D264G, T394M; S2P, M71C, D264G, F396Y; S2P, M71C, D264G, R400C; S2P, M71C, D264G, T413A; S2P, M71C, D264G, E423D; S2P, M71C, D264G, L453P; S2P, M71C, D264G, F458S; S2P, M71C, D264G, E461G; S2P, M71C, D264G, F465C; S2P, M71C, D264G, N467T; S2P, M71C, D264G, N470S; S2P, M71C, D264G, A476T; S2P, M71C, D264G, Q494R; S2P, M71C, D264G, T496R; S2P, M71C, D264G, G504S; S2P, M71V, T283A, L289P; S2P, M71V, T283A, F312L; S2P, M71V, T283A, T348A; S2P, M71V, T283A, L380F; S2P, M71V, T283A, T394M; S2P, M71V, T283A, F396Y; S2P, M71V, T283A, R400C; S2P, M71V, T283A, T413A; S2P, M71V, T283A, E423D; S2P, M71V, T283A, L453P; S2P, M71V, T283A, F458S; S2P, M71V, T283A, E461G; S2P, M71V, T283A, F465C; S2P, M71V, T283A, N467T; S2P, M71V, T283A, N470S; S2P, M71V, T283A, A476T; S2P, M71V, T283A, Q494R; S2P, M71V, T283A, T496R; S2P, M71V, T283A, G504S; S2P, M71T, T283A, L289P; S2P, M71T, T283A, F312L; S2P, M71T, T283A, T348A; S2P, M71T, T283A, L380F; S2P, M71T, T283A, T394M; S2P, M71T, T283A, F396Y; S2P, M71T, T283A, R400C; S2P, M71T, T283A, T413A; S2P, M71T, T283A, E423D; S2P, M71T, T283A, L453P; S2P, M71T, T283A, F458S; S2P, M71T, T283A, E461G; S2P, M71T, T283A, F465C; S2P, M71T, T283A, N467T; S2P, M71T, T283A, N470S; S2P, M71T, T283A, A476T; S2P, M71T, T283A, Q494R; S2P, M71T, T283A, T496R; S2P, M71T, T283A, G504S; S2P, M71A, T283A, L289P; S2P, M71A, T283A, F312L; S2P, M71A, T283A, T348A; S2P, M71A, T283A, L380F; S2P, M71A, T283A, T394M; S2P, M71A, T283A, F396Y; S2P, M71A, T283A, R400C; S2P, M71A, T283A, T413A; S2P, M71A, T283A, E423D; S2P, M71A, T283A, L453P; S2P, M71A, T283A, F458S; S2P, M71A, T283A, E461G; S2P, M71A, T283A, F465C; S2P, M71A, T283A, N467T; S2P, M71A, T283A, N470S; S2P, M71A, T283A, A476T; S2P, M71A, T283A, Q494R; S2P, M71A, T283A, T496R; S2P, M71A, T283A, G504S; S2P, M71C, T283A, L289P; S2P, M71C, T283A, F312L; S2P, M71C, T283A, T348A; S2P, M71C, T283A, L380F; S2P, M71C, T283A, T394M; S2P, M71C, T283A, F396Y; S2P, M71C, T283A, R400C; S2P, M71C, T283A, T413A; S2P, M71C, T283A, E423D; S2P, M71C, T283A, L453P; S2P, M71C, T283A, F458S; S2P, M71C, T283A, E461G; S2P, M71C, T283A, F465C; S2P, M71C, T283A, N467T; S2P, M71C, T283A, N470S; S2P, M71C, T283A,

A476T; S2P, M71C, T283A, Q494R; S2P, M71C, T283A, T496R; S2P, M71C, T283A, G504S; S2P, M71V, L289P, F312L; S2P, M71V, L289P, T348A; S2P, M71V, L289P, L380F; S2P, M71V, L289P, T394M; S2P, M71V, L289P, F396Y; S2P, M71V, L289P, R400C; S2P, M71V, L289P, T413A; S2P, M71V, L289P, E423D; S2P, M71V, L289P, L453P; S2P, M71V, L289P, F458S; S2P, M71V, L289P, E461G; S2P, M71V, L289P, F465C; S2P, M71V, L289P, N467T; S2P, M71V, L289P, N470S; S2P, M71V, L289P, A476T; S2P, M71V, L289P, Q494R; S2P, M71V, L289P, T496R; S2P, M71V, L289P, G504S; S2P, M71T, L289P, F312L; S2P, M71T, L289P, T348A; S2P, M71T, L289P, L380F; S2P, M71T, L289P, T394M; S2P, M71T, L289P, F396Y; S2P, M71T, L289P, R400C; S2P, M71T, L289P, T413A; S2P, M71T, L289P, E423D; S2P, M71T, L289P, L453P; S2P, M71T, L289P, F458S; S2P, M71T, L289P, E461G; S2P, M71T, L289P, F465C; S2P, M71T, L289P, N467T; S2P, M71T, L289P, N470S; S2P, M71T, L289P, A476T; S2P, M71T, L289P, Q494R; S2P, M71T, L289P, T496R; S2P, M71T, L289P, G504S; S2P, M71A, L289P, F312L; S2P, M71A, L289P, T348A; S2P, M71A, L289P, L380F; S2P, M71A, L289P, T394M; S2P, M71A, L289P, F396Y; S2P, M71A, L289P, R400C; S2P, M71A, L289P, T413A; S2P, M71A, L289P, E423D; S2P, M71A, L289P, L453P; S2P, M71A, L289P, F458S; S2P, M71A, L289P, E461G; S2P, M71A, L289P, F465C; S2P, M71A, L289P, N467T; S2P, M71A, L289P, N470S; S2P, M71A, L289P, A476T; S2P, M71A, L289P, Q494R; S2P, M71A, L289P, T496R; S2P, M71A, L289P, G504S; S2P, M71C, L289P, F312L; S2P, M71C, L289P, T348A; S2P, M71C, L289P, L380F; S2P, M71C, L289P, T394M; S2P, M71C, L289P, F396Y; S2P, M71C, L289P, R400C; S2P, M71C, L289P, T413A; S2P, M71C, L289P, E423D; S2P, M71C, L289P, L453P; S2P, M71C, L289P, F458S; S2P, M71C, L289P, E461G; S2P, M71C, L289P, F465C; S2P, M71C, L289P, N467T; S2P, M71C, L289P, N470S; S2P, M71C, L289P, A476T; S2P, M71C, L289P, Q494R; S2P, M71C, L289P, T496R; S2P, M71C, L289P, G504S; S2P, M71V, F312L, T348A; S2P, M71V, F312L, L380F; S2P, M71V, F312L, T394M; S2P, M71V, F312L, F396Y; S2P, M71V, F312L, R400C; S2P, M71V, F312L, T413A; S2P, M71V, F312L, E423D; S2P, M71V, F312L, L453P; S2P, M71V, F312L, F458S; S2P, M71V, F312L, E461G; S2P, M71V, F312L, F465C; S2P, M71V, F312L, N467T; S2P, M71V, F312L, N470S; S2P, M71V, F312L, A476T; S2P, M71V, F312L, Q494R; S2P, M71V, F312L, T496R; S2P, M71V, F312L, G504S; S2P, M71T, F312L, T348A; S2P, M71T, F312L, L380F; S2P, M71T, F312L, T394M; S2P, M71T, F312L, F396Y; S2P, M71T, F312L, R400C; S2P, M71T, F312L, T413A; S2P, M71T, F312L, E423D; S2P, M71T, F312L, L453P; S2P, M71T, F312L, F458S; S2P, M71T, F312L, E461G; S2P, M71T, F312L, F465C; S2P, M71T, F312L, N467T; S2P, M71T, F312L, N470S; S2P, M71T, F312L, A476T; S2P, M71T, F312L, Q494R; S2P, M71T, F312L, T496R; S2P, M71T, F312L, G504S; S2P, M71A, F312L, T348A; S2P, M71A, F312L, L380F; S2P, M71A, F312L, T394M; S2P, M71A, F312L, F396Y; S2P, M71A, F312L, R400C; S2P, M71A, F312L, T413A; S2P, M71A, F312L, E423D; S2P, M71A, F312L, L453P; S2P, M71A, F312L, F458S; S2P, M71A, F312L, E461G; S2P, M71A, F312L, F465C; S2P, M71A, F312L, N467T; S2P, M71A, F312L, N470S; S2P, M71A, F312L, A476T; S2P, M71A, F312L, Q494R; S2P, M71A, F312L, T496R; S2P, M71A, F312L, G504S; S2P, M71C, F312L, T348A; S2P, M71C, F312L, L380F; S2P, M71C, F312L, T394M; S2P, M71C, F312L, F396Y; S2P, M71C, F312L, R400C; S2P, M71C, F312L, T413A; S2P, M71C, F312L, E423D; S2P, M71C, F312L, L453P; S2P, M71C, F312L, F458S; S2P, M71C, F312L, E461G; S2P, M71C, F312L, F465C; S2P, M71C, F312L, N467T; S2P, M71C, F312L, N470S; S2P, M71C, F312L, A476T; S2P, M71C, F312L, Q494R; S2P, M71C, F312L, T496R; S2P, M71C, F312L, G504S; S2P, M71V, T348A, L380F; S2P, M71V, T348A, T394M; S2P, M71V, T348A, F396Y; S2P, M71V, T348A, R400C; S2P, M71V, T348A, T413A; S2P, M71V, T348A, E423D; S2P, M71V, T348A, L453P; S2P, M71V, T348A, F458S; S2P, M71V, T348A, E461G; S2P, M71V, T348A, F465C; S2P, M71V, T348A, N467T; S2P, M71V, T348A, N470S; S2P, M71V, T348A, A476T; S2P, M71V, T348A, Q494R; S2P, M71V, T348A, T496R; S2P, M71V, T348A, G504S; S2P, M71T, T348A, L380F; S2P, M71T, T348A, T394M; S2P, M71T, T348A, F396Y; S2P, M71T, T348A, R400C; S2P, M71T, T348A, T413A; S2P, M71T, T348A, E423D; S2P, M71T, T348A, L453P; S2P, M71T, T348A, F458S; S2P, M71T, T348A, E461G; S2P, M71T, T348A, F465C; S2P, M71T, T348A, N467T; S2P, M71T, T348A, N470S; S2P, M71T, T348A, A476T; S2P, M71T, T348A, Q494R; S2P, M71T, T348A, T496R; S2P, M71T, T348A, G504S; S2P, M71A, T348A, L380F; S2P, M71A, T348A, T394M; S2P, M71A, T348A, F396Y; S2P, M71A, T348A, R400C; S2P, M71A, T348A, T413A; S2P, M71A, T348A, E423D; S2P, M71A, T348A, L453P; S2P, M71A, T348A, F458S; S2P, M71A, T348A, E461G; S2P, M71A, T348A, F465C; S2P, M71A, T348A, N467T; S2P, M71A, T348A, N470S; S2P, M71A, T348A, A476T; S2P, M71A, T348A, Q494R; S2P, M71A, T348A, T496R; S2P, M71A, T348A, G504S; S2P, M71C, T348A, L380F; S2P, M71C, T348A, T394M; S2P, M71C, T348A, F396Y; S2P, M71C, T348A, R400C; S2P, M71C, T348A, T413A; S2P, M71C, T348A, E423D; S2P, M71C, T348A, L453P; S2P, M71C, T348A, F458S; S2P, M71C, T348A, E461G; S2P, M71C, T348A, F465C; S2P, M71C, T348A, N467T; S2P, M71C, T348A, N470S; S2P, M71C, T348A, A476T; S2P, M71C, T348A, Q494R; S2P, M71C, T348A, T496R; S2P, M71C, T348A, G504S; S2P, M71V, L380F, T394M; S2P, M71V, L380F, F396Y; S2P, M71V, L380F, R400C; S2P, M71V, L380F, T413A; S2P, M71V, L380F, E423D; S2P, M71V, L380F, L453P; S2P, M71V, L380F, F458S; S2P, M71V, L380F, E461G; S2P, M71V, L380F, F465C; S2P, M71V, L380F, N467T; S2P, M71V, L380F, N470S; S2P, M71V, L380F, A476T; S2P, M71V, L380F, Q494R; S2P, M71V, L380F, T496R; S2P, M71V, L380F, G504S; S2P, M71T, L380F, T394M; S2P, M71T, L380F, F396Y; S2P, M71T, L380F, R400C; S2P, M71T, L380F, T413A; S2P, M71T, L380F, E423D; S2P, M71T, L380F, L453P; S2P, M71T, L380F, F458S; S2P, M71T, L380F, E461G; S2P, M71T, L380F, F465C; S2P, M71T, L380F, N467T; S2P, M71T, L380F, N470S; S2P, M71T, L380F, A476T; S2P, M71T, L380F, Q494R; S2P, M71T, L380F, T496R; S2P, M71T, L380F, G504S; S2P, M71A, L380F, T394M; S2P, M71A, L380F, F396Y; S2P, M71A, L380F, R400C; S2P, M71A, L380F, T413A; S2P, M71A, L380F, E423D; S2P, M71A, L380F, L453P; S2P, M71A, L380F, F458S; S2P, M71A, L380F, E461G; S2P, M71A, L380F, F465C; S2P, M71A, L380F, N467T; S2P, M71A, L380F, N470S; S2P, M71A, L380F, A476T; S2P, M71A, L380F, Q494R; S2P, M71A, L380F, T496R; S2P, M71A, L380F, G504S; S2P, M71C, L380F, T394M; S2P, M71C, L380F, F396Y; S2P, M71C, L380F, R400C; S2P, M71C, L380F, T413A; S2P, M71C, L380F, E423D; S2P, M71C, L380F, L453P; S2P, M71C, L380F, F458S; S2P, M71C, L380F, E461G; S2P, M71C, L380F, F465C; S2P, M71C, L380F, N467T; S2P, M71C, L380F, N470S; S2P, M71C, L380F, A476T; S2P, M71C, L380F, Q494R; S2P, M71C, L380F, T496R; S2P, M71C, L380F, G504S; S2P, M71V, T394M,

F396Y; S2P, M71V, T394M, R400C; S2P, M71V, T394M, T413A; S2P, M71V, T394M, E423D; S2P, M71V, T394M, L453P; S2P, M71V, T394M, F458S; S2P, M71V, T394M, E461G; S2P, M71V, T394M, F465C; S2P, M71V, T394M, N467T; S2P, M71V, T394M, N470S; S2P, M71V, T394M, A476T; S2P, M71V, T394M, Q494R; S2P, M71V, T394M, T496R; S2P, M71V, T394M, G504S; S2P, M71T, T394M, F396Y; S2P, M71T, T394M, R400C; S2P, M71T, T394M, T413A; S2P, M71T, T394M, E423D; S2P, M71T, T394M, L453P; S2P, M71T, T394M, F458S; S2P, M71T, T394M, E461G; S2P, M71T, T394M, F465C; S2P, M71T, T394M, N467T; S2P, M71T, T394M, N470S; S2P, M71T, T394M, A476T; S2P, M71T, T394M, Q494R; S2P, M71T, T394M, T496R; S2P, M71T, T394M, G504S; S2P, M71A, T394M, F396Y; S2P, M71A, T394M, R400C; S2P, M71A, T394M, T413A; S2P, M71A, T394M, E423D; S2P, M71A, T394M, L453P; S2P, M71A, T394M, F458S; S2P, M71A, T394M, E461G; S2P, M71A, T394M, F465C; S2P, M71A, T394M, N467T; S2P, M71A, T394M, N470S; S2P, M71A, T394M, A476T; S2P, M71A, T394M, Q494R; S2P, M71A, T394M, T496R; S2P, M71A, T394M, G504S; S2P, M71C, T394M, F396Y; S2P, M71C, T394M, R400C; S2P, M71C, T394M, T413A; S2P, M71C, T394M, E423D; S2P, M71C, T394M, L453P; S2P, M71C, T394M, F458S; S2P, M71C, T394M, E461G; S2P, M71C, T394M, F465C; S2P, M71C, T394M, N467T; S2P, M71C, T394M, N470S; S2P, M71C, T394M, A476T; S2P, M71C, T394M, Q494R; S2P, M71C, T394M, T496R; S2P, M71C, T394M, G504S; S2P, M71V, F396Y, R400C; S2P, M71V, F396Y, T413A; S2P, M71V, F396Y, E423D; S2P, M71V, F396Y, L453P; S2P, M71V, F396Y, F458S; S2P, M71V, F396Y, E461G; S2P, M71V, F396Y, F465C; S2P, M71V, F396Y, N467T; S2P, M71V, F396Y, N470S; S2P, M71V, F396Y, A476T; S2P, M71V, F396Y, Q494R; S2P, M71V, F396Y, T496R; S2P, M71V, F396Y, G504S; S2P, M71T, F396Y, R400C; S2P, M71T, F396Y, T413A; S2P, M71T, F396Y, E423D; S2P, M71T, F396Y, L453P; S2P, M71T, F396Y, F458S; S2P, M71T, F396Y, E461G; S2P, M71T, F396Y, F465C; S2P, M71T, F396Y, N467T; S2P, M71T, F396Y, N470S; S2P, M71T, F396Y, A476T; S2P, M71T, F396Y, Q494R; S2P, M71T, F396Y, T496R; S2P, M71T, F396Y, G504S; S2P, M71A, F396Y, R400C; S2P, M71A, F396Y, T413A; S2P, M71A, F396Y, E423D; S2P, M71A, F396Y, L453P; S2P, M71A, F396Y, F458S; S2P, M71A, F396Y, E461G; S2P, M71A, F396Y, F465C; S2P, M71A, F396Y, N467T; S2P, M71A, F396Y, N470S; S2P, M71A, F396Y, A476T; S2P, M71A, F396Y, Q494R; S2P, M71A, F396Y, T496R; S2P, M71A, F396Y, G504S; S2P, M71C, F396Y, R400C; S2P, M71C, F396Y, T413A; S2P, M71C, F396Y, E423D; S2P, M71C, F396Y, L453P; S2P, M71C, F396Y, F458S; S2P, M71C, F396Y, E461G; S2P, M71C, F396Y, F465C; S2P, M71C, F396Y, N467T; S2P, M71C, F396Y, N470S; S2P, M71C, F396Y, A476T; S2P, M71C, F396Y, Q494R; S2P, M71C, F396Y, T496R; S2P, M71C, F396Y, G504S; S2P, M71V, R400C, T413A; S2P, M71V, R400C, E423D; S2P, M71V, R400C, L453P; S2P, M71V, R400C, F458S; S2P, M71V, R400C, E461G; S2P, M71V, R400C, F465C; S2P, M71V, R400C, N467T; S2P, M71V, R400C, N470S; S2P, M71V, R400C, A476T; S2P, M71V, R400C, Q494R; S2P, M71V, R400C, T496R; S2P, M71V, R400C, G504S; S2P, M71T, R400C, T413A; S2P, M71T, R400C, E423D; S2P, M71T, R400C, L453P; S2P, M71T, R400C, F458S; S2P, M71T, R400C, E461G; S2P, M71T, R400C, F465C; S2P, M71T, R400C, N467T; S2P, M71T, R400C, N470S; S2P, M71T, R400C, A476T; S2P, M71T, R400C, Q494R; S2P, M71T, R400C, T496R; S2P, M71T, R400C, G504S; S2P, M71A, R400C, T413A; S2P, M71A, R400C, E423D; S2P, M71A, R400C, L453P; S2P, M71A, R400C, F458S; S2P, M71A, R400C, E461G; S2P, M71A, R400C, F465C; S2P, M71A, R400C, N467T; S2P, M71A, R400C, N470S; S2P, M71A, R400C, A476T; S2P, M71A, R400C, Q494R; S2P, M71A, R400C, T496R; S2P, M71A, R400C, G504S; S2P, M71C, R400C, T413A; S2P, M71C, R400C, E423D; S2P, M71C, R400C, L453P; S2P, M71C, R400C, F458S; S2P, M71C, R400C, E461G; S2P, M71C, R400C, F465C; S2P, M71C, R400C, N467T; S2P, M71C, R400C, N470S; S2P, M71C, R400C, A476T; S2P, M71C, R400C, Q494R; S2P, M71C, R400C, T496R; S2P, M71C, R400C, G504S; S2P, M71V, T413A, E423D; S2P, M71V, T413A, L453P; S2P, M71V, T413A, F458S; S2P, M71V, T413A, E461G; S2P, M71V, T413A, F465C; S2P, M71V, T413A, N467T; S2P, M71V, T413A, N470S; S2P, M71V, T413A, A476T; S2P, M71V, T413A, Q494R; S2P, M71V, T413A, T496R; S2P, M71V, T413A, G504S; S2P, M71T, T413A, E423D; S2P, M71T, T413A, L453P; S2P, M71T, T413A, F458S; S2P, M71T, T413A, E461G; S2P, M71T, T413A, F465C; S2P, M71T, T413A, N467T; S2P, M71T, T413A, N470S; S2P, M71T, T413A, A476T; S2P, M71T, T413A, Q494R; S2P, M71T, T413A, T496R; S2P, M71T, T413A, G504S; S2P, M71A, T413A, E423D; S2P, M71A, T413A, L453P; S2P, M71A, T413A, F458S; S2P, M71A, T413A, E461G; S2P, M71A, T413A, F465C; S2P, M71A, T413A, N467T; S2P, M71A, T413A, N470S; S2P, M71A, T413A, A476T; S2P, M71A, T413A, Q494R; S2P, M71A, T413A, T496R; S2P, M71A, T413A, G504S; S2P, M71C, T413A, E423D; S2P, M71C, T413A, L453P; S2P, M71C, T413A, F458S; S2P, M71C, T413A, E461G; S2P, M71C, T413A, F465C; S2P, M71C, T413A, N467T; S2P, M71C, T413A, N470S; S2P, M71C, T413A, A476T; S2P, M71C, T413A, Q494R; S2P, M71C, T413A, T496R; S2P, M71C, T413A, G504S; S2P, M71V, E423D, L453P; S2P, M71V, E423D, F458S; S2P, M71V, E423D, E461G; S2P, M71V, E423D, F465C; S2P, M71V, E423D, N467T; S2P, M71V, E423D, N470S; S2P, M71V, E423D, A476T; S2P, M71V, E423D, Q494R; S2P, M71V, E423D, T496R; S2P, M71V, E423D, G504S; S2P, M71T, E423D, L453P; S2P, M71T, E423D, F458S; S2P, M71T, E423D, E461G; S2P, M71T, E423D, F465C; S2P, M71T, E423D, N467T; S2P, M71T, E423D, N470S; S2P, M71T, E423D, A476T; S2P, M71T, E423D, Q494R; S2P, M71T, E423D, T496R; S2P, M71T, E423D, G504S; S2P, M71A, E423D, L453P; S2P, M71A, E423D, F458S; S2P, M71A, E423D, E461G; S2P, M71A, E423D, F465C; S2P, M71A, E423D, N467T; S2P, M71A, E423D, N470S; S2P, M71A, E423D, A476T; S2P, M71A, E423D, Q494R; S2P, M71A, E423D, T496R; S2P, M71A, E423D, G504S; S2P, M71C, E423D, L453P; S2P, M71C, E423D, F458S; S2P, M71C, E423D, E461G; S2P, M71C, E423D, F465C; S2P, M71C, E423D, N467T; S2P, M71C, E423D, N470S; S2P, M71C, E423D, A476T; S2P, M71C, E423D, Q494R; S2P, M71C, E423D, T496R; S2P, M71C, E423D, G504S; S2P, M71V, L453P, F458S; S2P, M71V, L453P, E461G; S2P, M71V, L453P, F465C; S2P, M71V, L453P, N467T; S2P, M71V, L453P, N470S; S2P, M71V, L453P, A476T; S2P, M71V, L453P, Q494R; S2P, M71V, L453P, T496R; S2P, M71V, L453P, G504S; S2P, M71T, L453P, F458S; S2P, M71T, L453P, E461G; S2P, M71T, L453P, F465C; S2P, M71T, L453P, N467T; S2P, M71T, L453P, N470S; S2P, M71T, L453P, A476T, S2P, M71T, L453P, Q494R; S2P, M71T, L453P, T496R; S2P, M71T, L453P, G504S; S2P, M71A, L453P, F458S; S2P, M71A, L453P, E461G; S2P, M71A, L453P, F465C; S2P, M71A, L453P, N467T; S2P, M71A, L453P, N470S; S2P, M71A, L453P, A476T; S2P, M71A, L453P, Q494R; S2P, M71A, L453P, T496R; S2P, M71A, L453P, G504S; S2P, M71C, L453P, F458S; S2P, M71C, L453P,

E461G; S2P, M71C, L453P, F465C; S2P, M71C, L453P, N467T; S2P, M71C, L453P, N470S; S2P, M71C, L453P, A476T; S2P, M71C, L453P, Q494R; S2P, M71C, L453P, T496R; S2P, M71C, L453P, G504S; S2P, M71V, F458S, E461G; S2P, M71V, F458S, F465C; S2P, M71V, F458S, N467T; S2P, M71V, F458S, N470S; S2P, M71V, F458S, A476T; S2P, M71V, F458S, Q494R; S2P, M71V, F458S, T496R; S2P, M71V, F458S, G504S; S2P, M71T, F458S, E461G; S2P, M71T, F458S, F465C; S2P, M71T, F458S, N467T; S2P, M71T, F458S, N470S; S2P, M71T, F458S, A476T; S2P, M71T, F458S, Q494R; S2P, M71T, F458S, T496R; S2P, M71T, F458S, G504S; S2P, M71A, F458S, E461G; S2P, M71A, F458S, F465C; S2P, M71A, F458S, N467T; S2P, M71A, F458S, N470S; S2P, M71A, F458S, A476T; S2P, M71A, F458S, Q494R; S2P, M71A, F458S, T496R; S2P, M71A, F458S, G504S; S2P, M71C, F458S, E461G; S2P, M71C, F458S, F465C; S2P, M71C, F458S, N467T; S2P, M71C, F458S, N470S; S2P, M71C, F458S, A476T; S2P, M71C, F458S, Q494R; S2P, M71C, F458S, T496R; S2P, M71C, F458S, G504S; S2P, M71V, E461G, F465C; S2P, M71V, E461G, N467T; S2P, M71V, E461G, N470S; S2P, M71V, E461G, A476T; S2P, M71V, E461G, Q494R; S2P, M71V, E461G, T496R; S2P, M71V, E461G, G504S; S2P, M71T, E461G, F465C; S2P, M71T, E461G, N467T; S2P, M71T, E461G, N470S; S2P, M71T, E461G, A476T; S2P, M71T, E461G, Q494R; S2P, M71T, E461G, T496R; S2P, M71T, E461G, G504S; S2P, M71A, E461G, F465C; S2P, M71A, E461G, N467T; S2P, M71A, E461G, N470S; S2P, M71A, E461G, A476T; S2P, M71A, E461G, Q494R; S2P, M71A, E461G, T496R; S2P, M71A, E461G, G504S; S2P, M71C, E461G, F465C; S2P, M71C, E461G, N467T; S2P, M71C, E461G, N470S; S2P, M71C, E461G, A476T; S2P, M71C, E461G, Q494R; S2P, M71C, E461G, T496R; S2P, M71C, E461G, G504S; S2P, M71V, F465C, N467T; S2P, M71V, F465C, N470S; S2P, M71V, F465C, A476T; S2P, M71V, F465C, Q494R; S2P, M71V, F465C, T496R; S2P, M71V, F465C, G504S; S2P, M71T, F465C, N467T; S2P, M71T, F465C, N470S; S2P, M71T, F465C, A476T; S2P, M71T, F465C, Q494R; S2P, M71T, F465C, T496R; S2P, M71T, F465C, G504S; S2P, M71A, F465C, N467T; S2P, M71A, F465C, N470S; S2P, M71A, F465C, A476T; S2P, M71A, F465C, Q494R; S2P, M71A, F465C, T496R; S2P, M71A, F465C, G504S; S2P, M71C, F465C, N467T; S2P, M71C, F465C, N470S; S2P, M71C, F465C, A476T; S2P, M71C, F465C, Q494R; S2P, M71C, F465C, T496R; S2P, M71C, F465C, G504S; S2P, M71V, N467T, N470S; S2P, M71V, N467T, A476T; S2P, M71V, N467T, Q494R; S2P, M71V, N467T, T496R; S2P, M71V, N467T, G504S; S2P, M71T, N467T, N470S; S2P, M71T, N467T, A476T; S2P, M71T, N467T, Q494R; S2P, M71T, N467T, T496R; S2P, M71T, N467T, G504S; S2P, M71A, N467T, N470S; S2P, M71A, N467T, A476T; S2P, M71A, N467T, Q494R; S2P, M71A, N467T, T496R; S2P, M71A, N467T, G504S; S2P, M71C, N467T, N470S; S2P, M71C, N467T, A476T; S2P, M71C, N467T, Q494R; S2P, M71C, N467T, T496R; S2P, M71C, N467T, G504S; S2P, M71V, N470S, A476T; S2P, M71V, N470S, Q494R; S2P, M71V, N470S, T496R; S2P, M71V, N470S, G504S; S2P, M71T, N470S, A476T; S2P, M71T, N470S, Q494R; S2P, M71T, N470S, T496R; S2P, M71T, N470S, G504S; S2P, M71A, N470S, A476T; S2P, M71A, N470S, Q494R; S2P, M71A, N470S, T496R; S2P, M71A, N470S, G504S; S2P, M71C, N470S, A476T; S2P, M71C, N470S, Q494R; S2P, M71C, N470S, T496R; S2P, M71C, N470S, G504S; S2P, M71V, A476T, Q494R; S2P, M71V, A476T, T496R; S2P, M71V, A476T, G504S; S2P, M71T, A476T, Q494R; S2P, M71T, A476T, T496R; S2P, M71T, A476T, G504S; S2P, M71A, A476T, Q494R; S2P, M71A, A476T, T496R; S2P, M71A, A476T, G504S; S2P, M71C, A476T, Q494R; S2P, M71C, A476T, T496R; S2P, M71C, A476T, G504S; S2P, M71V, Q494R, T496R; S2P, M71V, Q494R, G504S; S2P, M71T, Q494R, T496R; S2P, M71T, Q494R, G504S; S2P, M71A, Q494R, T496R; S2P, M71A, Q494R, G504S; S2P, M71C, Q494R, T496R; S2P, M71C, Q494R, G504S; S2P, M71V, T496R, G504S; S2P, M71T, T496R, G504S; S2P, M71A, T496R, G504S; S2P, M71C, T496R, G504S; S2P, M71T, N75K, E96V; S2P, M71A, N75K, E96V; S2P, M71C, N75K, E96V; S2P, N75K, E96V, D101G; S2P, N75K, E96V, G112S; S2P, N75K, E96V, L114P; S2P, N75K, E96V, S130L; S2P, N75K, E96V, K145M; S2P, N75K, E96V, N166S; S2P, N75K, E96V, F171I; S2P, N75K, E96V, D203A; S2P, N75K, E96V, D203G; S2P, N75K, E96V, T213A; S2P, N75K, E96V, V225I; S2P, N75K, E96V, K237E; S2P, N75K, E96V, V256I; S2P, N75K, E96V, T258A; S2P, N75K, E96V, D264G; S2P, N75K, E96V, T283A; S2P, N75K, E96V, L289P; S2P, N75K, E96V, F312L; S2P, N75K, E96V, T348A; S2P, N75K, E96V, L380F; S2P, N75K, E96V, T394M; S2P, N75K, E96V, F396Y; S2P, N75K, E96V, R400C; S2P, N75K, E96V, T413A; S2P, N75K, E96V, E423D; S2P, N75K, E96V, L453P; S2P, N75K, E96V, F458S; S2P, N75K, E96V, E461G; S2P, N75K, E96V, F465C; S2P, N75K, E96V, N467T; S2P, N75K, E96V, N470S; S2P, N75K, E96V, A476T; S2P, N75K, E96V, Q494R; S2P, N75K, E96V, T496R; S2P, N75K, E96V, G504S; M71V, N75K, E96V, D101G; M71V, N75K, E96V, G112S; M71V, N75K, E96V, L114P; M71V, N75K, E96V, S130L; M71V, N75K, E96V, K145M; M71V, N75K, E96V, N166S; M71V, N75K, E96V, F171I; M71V, N75K, E96V, D203A; M71V, N75K, E96V, D203G; M71V, N75K, E96V, T213A; M71V, N75K, E96V, V225I; M71V, N75K, E96V, K237E; M71V, N75K, E96V, V256I; M71V, N75K, E96V, T258A; M71V, N75K, E96V, D264G; M71V, N75K, E96V, T283A; M71V, N75K, E96V, L289P; M71V, N75K, E96V, F312L; M71V, N75K, E96V, T348A; M71V, N75K, E96V, L380F; M71V, N75K, E96V, T394M; M71V, N75K, E96V, F396Y; M71V, N75K, E96V, R400C; M71V, N75K, E96V, T413A; M71V, N75K, E96V, E423D; M71V, N75K, E96V, L453P; M71V, N75K, E96V, F458S; M71V, N75K, E96V, E461G; M71V, N75K, E96V, F465C; M71V, N75K, E96V, N467T; M71V, N75K, E96V, N470S; M71V, N75K, E96V, A476T; M71V, N75K, E96V, Q494R; M71V, N75K, E96V, T496R; M71V, N75K, E96V, G504S; M71T, N75K, E96V, D101G; M71T, N75K, E96V, G112S; M71T, N75K, E96V, L114P; M71T, N75K, E96V, S130L; M71T, N75K, E96V, K145M; M71T, N75K, E96V, N166S; M71T, N75K, E96V, F171I; M71T, N75K, E96V, D203A; M71T, N75K, E96V, D203G; M71T, N75K, E96V, T213A; M71T, N75K, E96V, V225I; M71T, N75K, E96V, K237E; M71T, N75K, E96V, V256I; M71T, N75K, E96V, T258A; M71T, N75K, E96V, D264G; M71T, N75K, E96V, T283A; M71T, N75K, E96V, L289P; M71T, N75K, E96V, F312L; M71T, N75K, E96V, T348A; M71T, N75K, E96V, L380F; M71T, N75K, E96V, T394M; M71T, N75K, E96V, F396Y; M71T, N75K, E96V, R400C; M71T, N75K, E96V, T413A; M71T, N75K, E96V, E423D; M71T, N75K, E96V, L453P; M71T, N75K, E96V, F458S; M71T, N75K, E96V, E461G; M71T, N75K, E96V, F465C; M71T, N75K, E96V, N467T; M71T, N75K, E96V, N470S; M71T, N75K, E96V, A476T; M71T, N75K, E96V, Q494R; M71T, N75K, E96V, T496R; M71T, N75K, E96V, G504S; M71A, N75K, E96V, D101G; M71A, N75K, E96V, G112S; M71A, N75K, E96V, L114P; M71A, N75K, E96V, S130L; M71A, N75K, E96V, K145M; M71A, N75K, E96V, N166S; M71A, N75K, E96V, F171I; M71A, N75K, E96V, D203A; M71A, N75K, E96V, D203G; M71A, N75K, E96V,

T213A; M71A, N75K, E96V, V225I; M71A, N75K, E96V, K237E; M71A, N75K, E96V, V256I; M71A, N75K, E96V, T258A; M71A, N75K, E96V, D264G; M71A, N75K, E96V, T283A; M71A, N75K, E96V, L289P; M71A, N75K, E96V, F312L; M71A, N75K, E96V, T348A; M71A, N75K, E96V, L380F; M71A, N75K, E96V, T394M; M71A, N75K, E96V, F396Y; M71A, N75K, E96V, R400C; M71A, N75K, E96V, T413A; M71A, N75K, E96V, E423D; M71A, N75K, E96V, L453P; M71A, N75K, E96V, F458S; M71A, N75K, E96V, E461G; M71A, N75K, E96V, F465C; M71A, N75K, E96V, N467T; M71A, N75K, E96V, N470S; M71A, N75K, E96V, A476T; M71A, N75K, E96V, Q494R; M71A, N75K, E96V, T496R; M71A, N75K, E96V, G504S; M71C, N75K, E96V, D101G; M71C, N75K, E96V, G112S; M71C, N75K, E96V, L114P; M71C, N75K, E96V, S130L; M71C, N75K, E96V, K145M; M71C, N75K, E96V, N166S; M71C, N75K, E96V, F171I; M71C, N75K, E96V, D203A; M71C, N75K, E96V, D203G; M71C, N75K, E96V, T213A; M71C, N75K, E96V, V225I; M71C, N75K, E96V, K237E; M71C, N75K, E96V, V256I; M71C, N75K, E96V, T258A; M71C, N75K, E96V, D264G; M71C, N75K, E96V, T283A; M71C, N75K, E96V, L289P; M71C, N75K, E96V, F312L; M71C, N75K, E96V, T348A; M71C, N75K, E96V, L380F; M71C, N75K, E96V, T394M; M71C, N75K, E96V, F396Y; M71C, N75K, E96V, R400C; M71C, N75K, E96V, T413A; M71C, N75K, E96V, E423D; M71C, N75K, E96V, L453P; M71C, N75K, E96V, F458S; M71C, N75K, E96V, E461G; M71C, N75K, E96V, F465C; M71C, N75K, E96V, N467T; M71C, N75K, E96V, N470S; M71C, N75K, E96V, A476T; M71C, N75K, E96V, Q494R; M71C, N75K, E96V, T496R; M71C, N75K, E96V, G504S; N75K, E96V, D101G, G112S; N75K, E96V, D101G, L114P; N75K, E96V, D101G, S130L; N75K, E96V, D101G, K145M; N75K, E96V, D101G, N166S; N75K, E96V, D101G, F171I; N75K, E96V, D101G, D203A; N75K, E96V, D101G, D203G; N75K, E96V, D101G, T213A; N75K, E96V, D101G, V225I; N75K, E96V, D101G, K237E; N75K, E96V, D101G, V256I; N75K, E96V, D101G, T258A; N75K, E96V, D101G, D264G; N75K, E96V, D101G, T283A; N75K, E96V, D101G, L289P; N75K, E96V, D101G, F312L; N75K, E96V, D101G, T348A; N75K, E96V, D101G, L380F; N75K, E96V, D101G, T394M; N75K, E96V, D101G, F396Y; N75K, E96V, D101G, R400C; N75K, E96V, D101G, T413A; N75K, E96V, D101G, E423D; N75K, E96V, D101G, L453P; N75K, E96V, D101G, F458S; N75K, E96V, D101G, E461G; N75K, E96V, D101G, F465C; N75K, E96V, D101G, N467T; N75K, E96V, D101G, N470S; N75K, E96V, D101G, A476T; N75K, E96V, D101G, Q494R; N75K, E96V, D101G, T496R; N75K, E96V, D101G, G504S; E96V, D101G, G112S, L114P; E96V, D101G, G112S, S130L; E96V, D101G, G112S, K145M; E96V, D101G, G112S, N166S; E96V, D101G, G112S, F171I; E96V, D101G, G112S, D203A; E96V, D101G, G112S, D203G; E96V, D101G, G112S, T213A; E96V, D101G, G112S, V225I; E96V, D101G, G112S, K237E; E96V, D101G, G112S, V256I; E96V, D101G, G112S, T258A; E96V, D101G, G112S, D264G; E96V, D101G, G112S, T283A; E96V, D101G, G112S, L289P; E96V, D101G, G112S, F312L; E96V, D101G, G112S, T348A; E96V, D101G, G112S, L380F; E96V, D101G, G112S, T394M; E96V, D101G, G112S, F396Y; E96V, D101G, G112S, R400C; E96V, D101G, G112S, T413A; E96V, D101G, G112S, E423D; E96V, D101G, G112S, L453P; E96V, D101G, G112S, F458S; E96V, D101G, G112S, E461G; E96V, D101G, G112S, F465C; E96V, D101G, G112S, N467T; E96V, D101G, G112S, N470S; E96V, D101G, G112S, A476T; E96V, D101G, G112S, Q494R; E96V, D101G, G112S, T496R; E96V, D101G, G112S, G504S; D101G, G112S, L114P, S130L; D101G, G112S, L114P, K145M; D101G, G112S, L114P, N166S; D101G, G112S, L114P, F171I; D101G, G112S, L114P, D203A; D101G, G112S, L114P, D203G; D101G, G112S, L114P, T213A; D101G, G112S, L114P, V225I; D101G, G112S, L114P, K237E; D101G, G112S, L114P, V256I; D101G, G112S, L114P, T258A; D101G, G112S, L114P, D264G; D101G, G112S, L114P, T283A; D101G, G112S, L114P, L289P; D101G, G112S, L114P, F312L; D101G, G112S, L114P, T348A; D101G, G112S, L114P, L380F; D101G, G112S, L114P, T394M; D101G, G112S, L114P, F396Y; D101G, G112S, L114P, R400C; D101G, G112S, L114P, T413A; D101G, G112S, L114P, E423D; D101G, G112S, L114P, L453P; D101G, G112S, L114P, F458S; D101G, G112S, L114P, E461G; D101G, G112S, L114P, F465C; D101G, G112S, L114P, N467T; D101G, G112S, L114P, N470S; D101G, G112S, L114P, A476T; D101G, G112S, L114P, Q494R; D101G, G112S, L114P, T496R; D101G, G112S, L114P, G504S; G112S, L114P, S130L, K145M; G112S, L114P, S130L, N166S; G112S, L114P, S130L, F171I; G112S, L114P, S130L, D203A; G112S, L114P, S130L, D203G; G112S, L114P, S130L, T213A; G112S, L114P, S130L, V225I; G112S, L114P, S130L, K237E; G112S, L114P, S130L, V256I; G112S, L114P, S130L, T258A; G112S, L114P, S130L, D264G; G112S, L114P, S130L, T283A; G112S, L114P, S130L, L289P; G112S, L114P, S130L, F312L; G112S, L114P, S130L, T348A; G112S, L114P, S130L, L380F; G112S, L114P, S130L, T394M; G112S, L114P, S130L, F396Y; G112S, L114P, S130L, R400C; G112S, L114P, S130L, T413A; G112S, L114P, S130L, E423D; G112S, L114P, S130L, L453P; G112S, L114P, S130L, F458S; G112S, L114P, S130L, E461G; G112S, L114P, S130L, F465C; G112S, L114P, S130L, N467T; G112S, L114P, S130L, N470S; G112S, L114P, S130L, A476T; G112S, L114P, S130L, Q494R; G112S, L114P, S130L, T496R; G112S, L114P, S130L, G504S; L114P, S130L, K145M, N166S; L114P, S130L, K145M, F171I; L114P, S130L, K145M, D203A; L114P, S130L, K145M, D203G; L114P, S130L, K145M, T213A; L114P, S130L, K145M, V225I; L114P, S130L, K145M, K237E; L114P, S130L, K145M, V256I; L114P, S130L, K145M, T258A; L114P, S130L, K145M, D264G; L114P, S130L, K145M, T283A; L114P, S130L, K145M, L289P; L114P, S130L, K145M, F312L; L114P, S130L, K145M, T348A; L114P, S130L, K145M, L380F; L114P, S130L, K145M, T394M; L114P, S130L, K145M, F396Y; L114P, S130L, K145M, R400C; L114P, S130L, K145M, T413A; L114P, S130L, K145M, E423D; L114P, S130L, K145M, L453P; L114P, S130L, K145M, F458S; L114P, S130L, K145M, E461G; L114P, S130L, K145M, F465C; L114P, S130L, K145M, N467T; L114P, S130L, K145M, N470S; L114P, S130L, K145M, A476T; L114P, S130L, K145M, Q494R; L114P, S130L, K145M, T496R; L114P, S130L, K145M, G504S; S130L, K145M, N166S, F171I; S130L, K145M, N166S, D203A; S130L, K145M, N166S, D203G; S130L, K145M, N166S, T213A; S130L, K145M, N166S, V225I; S130L, K145M, N166S, K237E; S130L, K145M, N166S, V256I; S130L, K145M, N166S, T258A; S130L, K145M, N166S, D264G; S130L, K145M, N166S, T283A; S130L, K145M, N166S, L289P; S130L, K145M, N166S, F312L; S130L, K145M, N166S, T348A; S130L, K145M, N166S, L380F; S130L, K145M, N166S, T394M; S130L, K145M, N166S, F396Y; S130L, K145M, N166S, R400C; S130L, K145M, N166S, T413A; S130L, K145M, N166S, E423D; S130L, K145M, N166S, L453P; S130L, K145M, N166S, F458S; S130L, K145M, N166S, E461G; S130L, K145M,

N166S, F465C; S130L, K145M, N166S, N467T; S130L, K145M, N166S, N470S; S130L K145M, N166S, A476T; S130L, K145M, N166S, Q494R; S130L, K145M, N166S, T496R; S130L, K145M, N166S, G504S; K145M, N166S, F171I, D203A; K145M, N166S, F171I, D203G; K145M, N166S, F171I, T213A; K145M, N166S, F171I, V225I; K145M, N166S, F171I, K237E; K145M, N166S, F171I, V256I; K145M, N166S, F171I, T258A; K145M, N166S, F171I, D264G; K145M, N166S, F171I, T283A; K145M, N166S, F171I, L289P; K145M, N166S, F171I, F312L; K145M, N166S, F171I, T348A; K145M, N166S, F171I, L380F; K145M, N166S, F171I, T394M; K145M, N166S, F171I, F396Y; K145M, N166S, F171I, R400C; K145M, N166S, F171I, T413A; K145M, N166S, F171I, E423D; K145M, N166S, F171I, L453P; K145M, N166S, F171I, F458S; K145M, N166S, F171I, E461G; K145M, N166S, F171I, F465C; K145M, N166S, F171I, N467T; K145M, N166S, F171I, N470S; K145M, N166S, F171I, A476T; K145M, N166S, F171I, Q494R; K145M, N166S, F171I, T496R; K145M, N166S, F171I, G504S; N166S, F171I, D203A, D203G; N166S, F171I, D203A, T213A; N166S, F171I, D203A, V225I; N166S, F171I, D203A, K237E; N166S, F171I, D203A, V256I; N166S, F171I, D203A, T258A; N166S, F171I, D203A, D264G; N166S, F171I, D203A, T283A; N166S, F171I, D203A, L289P; N166S, F171I, D203A, F312L; N166S, F171I, D203A, T348A; N166S, F171I, D203A, L380F; N166S, F171I, D203A, T394M; N166S, F171I, D203A, F396Y; N166S, F171I, D203A, R400C; N166S, F171I, D203A, T413A; N166S, F171I, D203A, E423D; N166S, F171I, D203A, L453P; N166S, F171I, D203A, F458S; N166S, F171I, D203A, E461G; N166S, F171I, D203A, F465C; N166S, F171I, D203A, N467T; N166S, F171I, D203A, N470S; N166S, F171I, D203A, A476T; N166S, F171I, D203A, Q494R; N166S, F171I, D203A, T496R; N166S, F171I, D203A, G504S; F171I, D203A, T213A, V225I; F171I, D203A, T213A, K237E; F171I, D203A, T213A, V256I; F171I, D203A, T213A, T258A; F171I, D203A, T213A, D264G; F171I, D203A, T213A, T283A; F171I, D203A, T213A, L289P; F171I, D203A, T213A, F312L; F171I, D203A, T213A, T348A; F171I, D203A, T213A, L380F; F171I, D203A, T213A, T394M; F171I, D203A, T213A, F396Y; F171I, D203A, T213A, R400C; F171I, D203A, T213A, T413A; F171I, D203A, T213A, E423D; F171I, D203A, T213A, L453P; F171I, D203A, T213A, F458S; F171I, D203A, T213A, E461G; F171I, D203A, T213A, F465C; F171I, D203A, T213A, N467T; F171I, D203A, T213A, N470S; F171I, D203A, T213A, A476T; F171I, D203A, T213A, Q494R; F171I, D203A, T213A, T496R; F171I, D203A, T213A, G504S; F171I, D203G, T213A, V225I; F171I, D203G, T213A, K237E; F171I, D203G, T213A, V256I; F171I, D203G, T213A, T258A; F171I, D203G, T213A, D264G; F171I, D203G, T213A, T283A; F171I, D203G, T213A, L289P; F171I, D203G, T213A, F312L; F171I, D203G, T213A, T348A; F171I, D203G, T213A, L380F; F171I, D203G, T213A, T394M; F171I, D203G, T213A, F396Y; F171I, D203G, T213A, R400C; F171I, D203G, T213A, T413A; F171I, D203G, T213A, E423D; F171I, D203G, T213A, L453P; F171I, D203G, T213A, F458S; F171I, D203G, T213A, E461G; F171I, D203G, T213A, F465C; F171I, D203G, T213A, N467T; F171I, D203G, T213A, N470S; F171I, D203G, T213A, A476T; F171I, D203G, T213A, Q494R; F171I, D203G, T213A, T496R; F171I, D203G, T213A, G504S; D203A, T213A, V225I, K237E; D203A, T213A, V225I, V256I; D203A, T213A, V225I, T258A; D203A, T213A, V225I, D264G; D203A, T213A, V225I, T283A; D203A, T213A, V225I, L289P; D203A, T213A, V225I, F312L; D203A, T213A, V225I, T348A; D203A, T213A, V225I, L380F; D203A, T213A, V225I, T394M; D203A, T213A, V225I, F396Y; D203A, T213A, V225I, R400C; D203A, T213A, V225I, T413A; D203A, T213A, V225I, E423D; D203A, T213A, V225I, L453P; D203A, T213A, V225I, F458S; D203A, T213A, V225I, E461G; D203A, T213A, V225I, F465C; D203A, T213A, V225I, N467T; D203A, T213A, V225I, N470S; D203A, T213A, V225I, A476T; D203A, T213A, V225I, Q494R; D203A, T213A, V225I, T496R; D203A, T213A, V225I, G504S; D203G, T213A, K237E, V256I; D203G, T213A, K237E, T258A; D203G, T213A, K237E, D264G; D203G, T213A, K237E, T283A; D203G, T213A, K237E, L289P; D203G, T213A, K237E, F312L; D203G, T213A, K237E, T348A; D203G, T213A, K237E, L380F; D203G, T213A, K237E, T394M; D203G, T213A, K237E, F396Y; D203G, T213A, K237E, R400C; D203G, T213A, K237E, T413A; D203G, T213A, K237E, E423D; D203G, T213A, K237E, L453P; D203G, T213A, K237E, F458S; D203G, T213A, K237E, E461G; D203G, T213A, K237E, F465C; D203G, T213A, K237E, N467T; D203G, T213A, K237E, N470S; D203G, T213A, K237E, A476T; D203G, T213A, K237E, Q494R; D203G, T213A, K237E, T496R; D203G, T213A, K237E, G504S; T213A, V225I, K237E, V256I; T213A, V225I, K237E, T258A; T213A, V225I, K237E, D264G; T213A, V225I, K237E, T283A; T213A, V225I, K237E, L289P; T213A, V225I, K237E, F312L; T213A, V225I, K237E, T348A; T213A, V225I, K237E, L380F; T213A, V225I, K237E, T394M; T213A, V225I, K237E, F396Y; T213A, V225I, K237E, R400C; T213A, V225I, K237E, T413A; T213A, V225I, K237E, E423D; T213A, V225I, K237E, L453P; T213A, V225I, K237E, F458S; T213A, V225I, K237E, E461G; T213A, V225I, K237E, F465C; T213A, V225I, K237E, N467T; T213A, V225I, K237E, N470S; T213A, V225I, K237E, A476T; T213A, V225I, K237E, Q494R; T213A, V225I, K237E, T496R; T213A, V225I, K237E, G504S; V225I, K237E, V256I, T258A; V225I, K237E, V256I, D264G; V225I, K237E, V256I, T283A; V225I, K237E, V256I, L289P; V225I, K237E, V256I, F312L; V225I, K237E, V256I, T348A; V225I, K237E, V256I, L380F; V225I, K237E, V256I, T394M; V225I, K237E, V256I, F396Y; V225I, K237E, V256I, R400C; V225I, K237E, V256I, T413A; V225I, K237E, V256I, E423D; V225I, K237E, V256I, L453P; V225I, K237E, V256I, F458S; V225I, K237E, V256I, E461G; V225I, K237E, V256I, F465C; V225I, K237E, V256I, N467T; V225I, K237E, V256I, N470S; V225I, K237E, V256I, A476T; V225I, K237E, V256I, Q494R; V225I, K237E, V256I, T496R; V225I, K237E, V256I, G504S; K237E, V256I, T258A, D264G; K237E, V256I, T258A, T283A; K237E, V256I, T258A, L289P; K237E, V256I, T258A, F312L; K237E, V256I, T258A, T348A; K237E, V256I, T258A, L380F; K237E, V256I, T258A, T394M; K237E, V256I, T258A, F396Y; K237E, V256I, T258A, R400C; K237E, V256I, T258A, T413A; K237E, V256I, T258A, E423D; K237E, V256I, T258A, L453P; K237E, V256I, T258A, F458S; K237E, V256I, T258A, E461G; K237E, V256I, T258A, F465C; K237E, V256I, T258A, N467T; K237E, V256I, T258A, N470S; K237E, V256I, T258A, A476T; K237E, V256I, T258A, Q494R; K237E, V256I, T258A, T496R; K237E, V256I, T258A, G504S; V256I, T258A, D264G, T283A; V256I, T258A, D264G, L289P; V256I, T258A, D264G, F312L; V256I, T258A, D264G, T348A; V256I, T258A, D264G, L380F; V256I, T258A, D264G, T394M; V256I, T258A, D264G, F396Y; V256I, T258A, D264G, R400C; V256I, T258A, D264G, T413A; V256I, T258A, D264G, E423D;

V256I, T258A, D264G, L453P; V256I, T258A, D264G, F458S; V256I, T258A, D264G, E461G; V256I, T258A, D264G, F465C; V256I, T258A, D264G, N467T; V256I, T258A, D264G, N470S; V256I, T258A, D264G, A476T; V256I, T258A, D264G, Q494R; V256I, T258A, D264G, T496R; V256I, T258A, D264G, G504S; T258A, D264G, T283A, L289P; T258A, D264G, T283A, F312L; T258A, D264G, T283A, T348A; T258A, D264G, T283A, L380F; T258A, D264G, T283A, T394M; T258A, D264G, T283A, F396Y; T258A, D264G, T283A, R400C; T258A, D264G, T283A, T413A; T258A, D264G, T283A, E423D; T258A, D264G, T283A, L453P; T258A, D264G, T283A, F458S; T258A, D264G, T283A, E461G; T258A, D264G, T283A, F465C; T258A, D264G, T283A, N467T; T258A, D264G, T283A, N470S; T258A, D264G, T283A, A476T; T258A, D264G, T283A, Q494R; T258A, D264G, T283A, T496R; T258A, D264G, T283A, G504S; D264G, T283A, L289P, F312L; D264G, T283A, L289P, T348A; D264G, T283A, L289P, L380F; D264G, T283A, L289P, T394M; D264G, T283A, L289P, F396Y; D264G, T283A, L289P, R400C; D264G, T283A, L289P, T413A; D264G, T283A, L289P, E423D; D264G, T283A, L289P, L453P; D264G, T283A, L289P, F458S; D264G, T283A, L289P, E461G; D264G, T283A, L289P, F465C; D264G, T283A, L289P, N467T; D264G, T283A, L289P, N470S; D264G, T283A, L289P, A476T; D264G, T283A, L289P, Q494R; D264G, T283A, L289P, T496R; D264G, T283A, L289P, G504S; T283A, L289P, F312L, T348A; T283A, L289P, F312L, L380F; T283A, L289P, F312L, T394M; T283A, L289P, F312L, F396Y; T283A, L289P, F312L, R400C; T283A, L289P, F312L, T413A; T283A, L289P, F312L, E423D; T283A, L289P, F312L, L453P; T283A, L289P, F312L, F458S; T283A, L289P, F312L, E461G; T283A, L289P, F312L, F465C; T283A, L289P, F312L, N467T; T283A, L289P, F312L, N470S; T283A, L289P, F312L, A476T; T283A, L289P, F312L, Q494R; T283A, L289P, F312L, T496R; T283A, L289P, F312L, G504S; L289P, F312L, T348A, L380F; L289P, F312L, T348A, T394M; L289P, F312L, T348A, F396Y; L289P, F312L, T348A, R400C; L289P, F312L, T348A, T413A; L289P, F312L, T348A, E423D; L289P, F312L, T348A, L453P; L289P, F312L, T348A, F458S; L289P, F312L, T348A, E461G; L289P, F312L, T348A, F465C; L289P, F312L, T348A, N467T; L289P, F312L, T348A, N470S; L289P, F312L, T348A, A476T; L289P, F312L, T348A, Q494R; L289P, F312L, T348A, T496R; L289P, F312L, T348A, G504S; F312L, T348A, L380F, T394M; F312L, T348A, L380F, F396Y; F312L, T348A, L380F, R400C; F312L, T348A, L380F, T413A; F312L, T348A, L380F, E423D; F312L, T348A, L380F, L453P; F312L, T348A, L380F, F458S; F312L, T348A, L380F, E461G; F312L, T348A, L380F, F465C; F312L, T348A, L380F, N467T; F312L, T348A, L380F, N470S; F312L, T348A, L380F, A476T; F312L, T348A, L380F, Q494R; F312L, T348A, L380F, T496R; F312L, T348A, L380F, G504S; T348A, L380F, T394M, F396Y; T348A, L380F, T394M, R400C; T348A, L380F, T394M, T413A; T348A, L380F, T394M, E423D; T348A, L380F, T394M, L453P; T348A, L380F, T394M, F458S; T348A, L380F, T394M, E461G; T348A, L380F, T394M, F465C; T348A, L380F, T394M, N467T; T348A, L380F, T394M, N470S; T348A, L380F, T394M, A476T; T348A, L380F, T394M, Q494R; T348A, L380F, T394M, T496R; T348A, L380F, T394M, G504S; L380F, T394M, F396Y, R400C; L380F, T394M, F396Y, T413A; L380F, T394M, F396Y, E423D; L380F, T394M, F396Y, L453P; L380F, T394M, F396Y, F458S; L380F, T394M, F396Y, E461G; L380F, T394M, F396Y, F465C; L380F, T394M, F396Y, N467T; L380F, T394M, F396Y, N470S; L380F, T394M, F396Y, A476T; L380F, T394M, F396Y, Q494R; L380F, T394M, F396Y, T496R; L380F, T394M, F396Y, G504S; T394M, F396Y, R400C, T413A; T394M, F396Y, R400C, E423D; T394M, F396Y, R400C, L453P; T394M, F396Y, R400C, F458S; T394M, F396Y, R400C, E461G; T394M, F396Y, R400C, F465C; T394M, F396Y, R400C, N467T; T394M, F396Y, R400C, N470S; T394M, F396Y, R400C, A476T; T394M, F396Y, R400C, Q494R; T394M, F396Y, R400C, T496R; T394M, F396Y, R400C, G504S; F396Y, R400C, T413A, E423D; F396Y, R400C, T413A, L453P; F396Y, R400C, T413A, F458S; F396Y, R400C, T413A, E461G; F396Y, R400C, T413A, F465C; F396Y, R400C, T413A, N467T; F396Y, R400C, T413A, N470S; F396Y, R400C, T413A, A476T; F396Y, R400C, T413A, Q494R; F396Y, R400C, T413A, T496R; F396Y, R400C, T413A, G504S; R400C, T413A, E423D, L453P; R400C, T413A, E423D, F458S; R400C, T413A, E423D, E461G; R400C, T413A, E423D, F465C; R400C, T413A, E423D, N467T; R400C, T413A, E423D, N470S; R400C, T413A, E423D, A476T; R400C, T413A, E423D, Q494R; R400C, T413A, E423D, T496R; R400C, T413A, E423D, G504S; T413A, E423D, L453P, F458S; T413A, E423D, L453P, E461G; T413A, E423D, L453P, F465C; T413A, E423D, L453P, N467T; T413A, E423D, L453P, N470S; T413A, E423D, L453P, A476T; T413A, E423D, L453P, Q494R; T413A, E423D, L453P, T496R; T413A, E423D, L453P, G504S; E423D, L453P, F458S, E461G; E423D, L453P, F458S, F465C; E423D, L453P, F458S, N467T; E423D, L453P, F458S, N470S; E423D, L453P, F458S, A476T; E423D, L453P, F458S, Q494R; E423D, L453P, F458S, T496R; E423D, L453P, F458S, G504S; L453P, F458S, E461G, F465C; L453P, F458S, E461G, N467T; L453P, F458S, E461G, N470S; L453P, F458S, E461G, A476T; L453P, F458S, E461G, Q494R; L453P, F458S, E461G, T496R; L453P, F458S, E461G, G504S; F458S, E461G, F465C, N467T; F458S, E461G, F465C, N470S; F458S, E461G, F465C, A476T; F458S, E461G, F465C, Q494R; F458S, E461G, F465C, T496R; F458S, E461G, F465C, G504S; E461G, F465C, N467T, N470S; E461G, F465C, N467T, A476T; E461G, F465C, N467T, Q494R; E461G, F465C, N467T, T496R; E461G, F465C, N467T, G504S; F465C, N467T, N470S, A476T; F465C, N467T, N470S, Q494R; F465C, N467T, N470S, T496R; F465C, N467T, N470S, G504S; N467T, N470S, A476T, Q494R; N467T, N470S, A476T, T496R; N467T, N470S, A476T, G504S; N470S, A476T, Q494R, T496R; N470S, A476T, Q494R, G504S; A476T, Q494R, T496R, G504S; S2P, M71V, K145M, E423D, E461G; S2P, M71V, K145M, N467T, L380F; S2P, M71V, K145M, N467T, V256I; S2P, M71V, K145M, N467T, G112S; S2P, M71V, K145M, N467T, L114P; S2P, M71V, K145M, E423D, E461G, Q494R; S2P, M71V, K145M, E423D, E461G, K237E; S2P, M71V, K145M, E423D, E461G, S130L; S2P, M71V, K145M, E423D, E461G, T496R; S2P, M71V, K145M, E423D, E461G, G504S; S2P, M71V, K145M, E461G, T258A, L289P; S2P, M71V, K145M, E423D, E461G, N166S; S2P, M71V, K145M, T348A, L453, P A476T; S2P, M71V, K145M, N467T, D101G, K237E; S2P, M71V, K145M, N467T, F171I, T283A; S2P, M71V, K145M, N467T, G112S, N470S; S2P, M71V, K145M, E423D, E461G, T413A, Q494R; S2P, M71V, K145M, E423D, E461G, Q494R, S130L; S2P, M71V, K145M, E423D, E461G, Q494R, N166S; S2P, M71V, K145M, E423D, E461G, S130L, N166S; S2P, M71V, K145M, N467T, G112S, N470S, L114P; S2P, M71V, K145M, N467T, G112S, N470S, R400C; S2P, M71V, K145M, N467T, G112S, N470S, D203G; S2P, M71V, K145M,

N467T, G112S, N470S, V225I; S2P, M71V, K145M, E423D, E461G, Q494R, S130L, N166S; S2P, M71V, K145M, E423D, E461G, Q494R, S130L, G112S; and S2P, M71V, K145M, E423D, E461G, Q494R, S130L, N467T, G112S, N470S. It is further understood that these combinations of substitutions described above may be equivalent substitutions in a polypeptide sequence that varies from SEQ ID NO:1, but at a position that is equivalent to the position set forth with respect to SEQ ID NO:1.

It is understood that embodiments also concern a nucleic acid encoding any of the RebH variants discussed herein. Accordingly, nucleic acid variants of SEQ ID NO:2 that encode a RebH variant are contemplated. Such nucleic acids may be DNA, RNA, isolated, purified, single-stranded, double-stranded, and/or in a vector or expression construct.

The terms "mutant" and "variant" are used interchangeably and are defined as a protein which includes at least one amino acid substitution compared to the wild-type protein. The term "coupled" is defined as connected, although not necessarily directly, and not necessarily mechanically. The terms "a" and "an" are defined as one or more unless this disclosure explicitly requires otherwise.

The term "substantially" is defined as being largely but not necessarily wholly what is specified (and include wholly what is specified) as understood by one of ordinary skill in the art. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a RebH variant that "comprises," "has," "includes" or "contains" one or more elements possesses those one or more elements, but is not limited to possessing only those one or more elements. Likewise, an element of a system or composition that "comprises," "has," "includes" or "contains" one or more features possesses those one or more features, but is not limited to possessing only those one or more features.

The term "regioselective" is defined as a chemical reaction that preferably created one chemical bond over other creatable chemical bonds. Catalytic efficiency is a measure of the rate of product formation and the ability of an enzyme to chemically transform every substrate molecule it encounters. The term "native substrate" is defined as a compound that is a usual chemical target of an enzyme in a physiological system. The term "non-native substrate" is defined as a compound that is not a usual chemical target of an enzyme in a physiological system.

The terms "aryl" and "aromatic" are used interchangeably herein and refer to covalently bound, cyclic or polycyclic compounds with a delocalized conjugated system of $\pi$ electrons, where the number of delocalized $\pi$ electrons is even but not a multiple of 4. Aryl and aromatic compounds are typically represented by cyclic Kekule structures with alternating single and double bonds, i.e. a conjugated electron system. The term "aryl" includes heteroatom-unsubstituted aryl, heteroatom-substituted aryl, heteroatom-unsubstituted $C_n$-aryl, heteroatom-substituted $C_n$-aryl, heteroaryl, heterocyclic aryl groups, carbocyclic aryl groups, biaryl groups, and single-valent radicals derived from polycyclic fused hydrocarbons (PAHs). The term "heteroatom-unsubstituted $C_n$-aryl" refers to an aromatic ring structure containing only carbon atoms and no heteroatoms. For example, a heteroatom-unsubstituted $C_6$-$C_{10}$-aryl has 6 to 10 carbon atoms. Non-limiting examples of heteroatom-unsubstituted aryl groups include phenyl (Ph), methylphenyl, (dimethyl) phenyl, —$C_6H_4CH_2CH_3$, —$C_6H_4CH_2CH_2CH_3$, —$C_6H_4CH(CH_3)_2$, —$C_6H_4CH(CH_2)_2$, —$C_6H_3(CH_3)CH_2CH_3$, —$C_6H_4CH=CH_2$, —$C_6H_4CH=CHCH_3$, —$C_6H_4C\equiv CH$, —$C_6H_4C\equiv CCH_3$, naphthyl, and the radical derived from biphenyl. Non-limiting examples of heteroatom-unsubstituted aryl compounds include benzene, toluene, ethylbenzene, naphthalene, and 1-methyl-2-ethylnaphthalene. The term "heteroatom-substituted $C_n$-aryl" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-aryl has 1 to 10 carbon atoms. Non-limiting examples of heteroatom-substituted aryl groups include the groups: —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OC(O)CH_3$, —$C_6H_4NH_2$, —$C_6H_4NHCH_3$, —$C_6H_4N(CH_3)_2$, —$C_6H_4CH_2OH$, —$C_6H_4CH_2OC(O)CH_3$, —$C_6H_4CH_2NH_2$, —$C_6H_4CF_3$, —$C_6H_4CN$, —$C_6H_4CHO$, —$C_6H_4CHO$, —$C_6H_4C(O)CH_3$, —$C_6H_4C(O)C_6H_5$, —$C_6H_4CO_2H$, —$C_6H_4CO_2CH_3$, —$C_6H_4CONH_2$, —$C_6H_4CONHCH_3$, and —$C_6H_4CON(CH_3)_2$. In certain embodiments, heteroatom-substituted aryl groups are contemplated. In certain embodiments, heteroatom-unsubstituted aryl groups are contemplated. In certain embodiments, an aryl group may be mono-, di-, tri-, tetra- or penta-substituted with one or more heteroatom-containing substituents. The term "substituted aryl" refers to a monovalent group with an aromatic carbon atom as the point of attachment, said carbon atom forming part of an aromatic ring structure wherein the ring atoms are all carbon, and wherein the monovalent group further has at least one atom independently selected from the group consisting of C, N, O, F, Cl, Br, I, Si, P, and S. Non-limiting examples of substituted aryl groups include the groups: —$C_6H_5F$, —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OC(O)CH_3$, —$C_6H_4NH_2$, —$C_6H_4NHCH_3$, —$C_6H_4N(CH_3)_2$, —$C_6H_4CH_2OH$, —$C_6H_4CH_2OC(O)CH_3$, —$C_6H_4CH_2NH_2$, —$C_6H_4CF_3$, —$C_6H_4CN$, —$C_6H_4CHO$, —$C_6H_4CHO$, —$C_6H_4C(O)CH_3$, —$C_6H_4C(O)C_6H_5$, —$C_6H_4CO_2H$, —$C_6H_4CO_2CH_3$, —$C_6H_4CONH_2$, —$C_6H_4CONHCH_3$, and —$C_6H_4CON(CH_3)_2$.

As used herein, "heteroaryl" and "heteroaromatic" may be used interchangeably and refer to an aromatic ring system containing at least one ring heteroatom selected from oxygen (O), nitrogen (N), sulfur (S), silicon (Si), and selenium (Se). Heteroaryl and heteroaromatic compounds may not include an alternating single/double bond system if the heteroatom(s) contributes one or more $\pi$ electrons to the delocalized conjugated system. An example of a heteroaromatic compound that does not include an alternating single/double bond system is pyrrole. The heteroaryl rings typically comprise a five or six membered aromatic ring, which may however be bonded to additional rings, so as to form a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

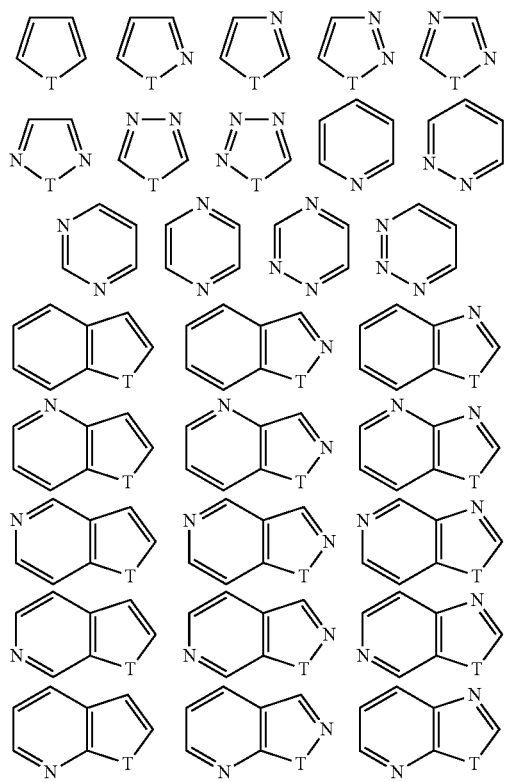

where T is O, S, NH, N-alkyl, N-aryl, N-(arylalkyl) (e.g., N-benzyl), $SiH_2$, SiH(alkyl), $Si(alkyl)_2$, SiH(arylalkyl), $Si(arylalkyl)_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuryl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyrdazinyl, thienothiazolyl, thienooxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein. The term "substituted heteroaryl" refers to a heteroaromatic compound or a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

In certain embodiments a protein or peptide may be isolated or purified. Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. An example of receptor protein purification by affinity chromatography is disclosed in U.S. Pat. No. 5,206,347, the entire text of which is incorporated herein by reference. A particularly efficient method of purifying peptides is fast performance liquid chromatography (FPLC) or high performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A particular method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

To purify a desired protein, polypeptide, or peptide a natural or recombinant composition comprising at least some specific proteins, polypeptides, or peptides may be subjected to fractionation to remove various other components from the composition. Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxyapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Furthermore, a structure or composition that is configured in a certain way is configured in at least that way, but may also be configured in ways that are not listed. Metric units may be derived from the English units provided by applying a conversion and rounding to the nearest millimeter.

The feature or features of one embodiment may be applied to other embodiments, even though not described or illustrated, unless expressly prohibited by this disclosure or the nature of the embodiments.

Any embodiment of any of the disclosed container assemblies and compositions can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-B. Residual activity following incubation at 49° C. for 2 hr. Tryptophan halogenation reactions were performed on tryptophan with 2% (FIG. 1A) and 0.5% (FIG. 1B) enzyme loading. The best variant (designated 1-PVM) from the first generation library contained three mutations: S2P, M71V, and K145M (FIG. 1A). The 1-PVM mutant was used as the parent for the second-generation random mutagenesis library. Variant 4G6 was identified as having 2.5-fold the activity of the parent and harbored the additional amino acid mutations E423D and E461G as well as a silent nucleotide mutation. The third-generation random mutagenesis library used 4G6 as the template. The three best-performing variants from the third round of screening each contained single amino acid mutations. Following recombination, the two best variants were identified as 3-LR and 3-LSR, which possess the additional mutations S130L and Q494R (3-RL) and S130L, N166S, and Q494R (3-LSR) (FIG. 1B).

FIG. 2. Unfolding transitions from thermal denaturation monitored using CD at 222 nm. The melting temperatures of the best mutants identified throughout the rounds of genetic diversification, screening, and recombination were analyzed to probe the relationship between residual activity and thermostability. Melting temperature measurements were conducted in 20 mM HEPES (pH 7.4), 150 mM NaCl, and 10% glycerol, with a protein concentration of 20 µM. Thermal denaturation was irreversible and monitored by circular dichroism spectroscopy using an AVIV 202 CD Spectrometer with Peltier temperature controller. Unfolding was monitored at 222 nm in 2° C. increments from 20-90° C. with 2 min equilibration at each temperature. The midpoint of the denaturation curve was determined with SigmaPlot (Systat Software, San Jose, Calif.) after fitting to a 4-parameter sigmoid. Wild-type RebH has a melting temperature of 52.4° C., and that of the most thermostable variant, 3-LSR, is 70.0° C. The 18° C. increase in $T_m$ indicates significant improvement in enzyme stability and is approximately equal to the difference between enzymes of mesophiles and those of thermophiles.

FIGS. 5A-E. Results (conversion %) of RebH variants tested for their ability to chlorinate tryptoline at different catalyst loads.

FIGS. 6A-E. Thermostability results of wild type RebH and RebH variants. Thermostability analyses were performed at different temperatures and catalyst loads for a set time period. The results are given as percent conversion of tryptophan to 7-chlorotryptophan.

FIGS. 7A-B. Thermostability results of wild type RebH and RebH variants. Thermostability analyses were performed at different temperatures and catalyst loads for a set time period. The results are given as percent conversion of tryptophan to 7-chlorotryptophan.

DESCRIPTION OF ILLUSTRATIVE EMBODIMENTS

Figure 3:
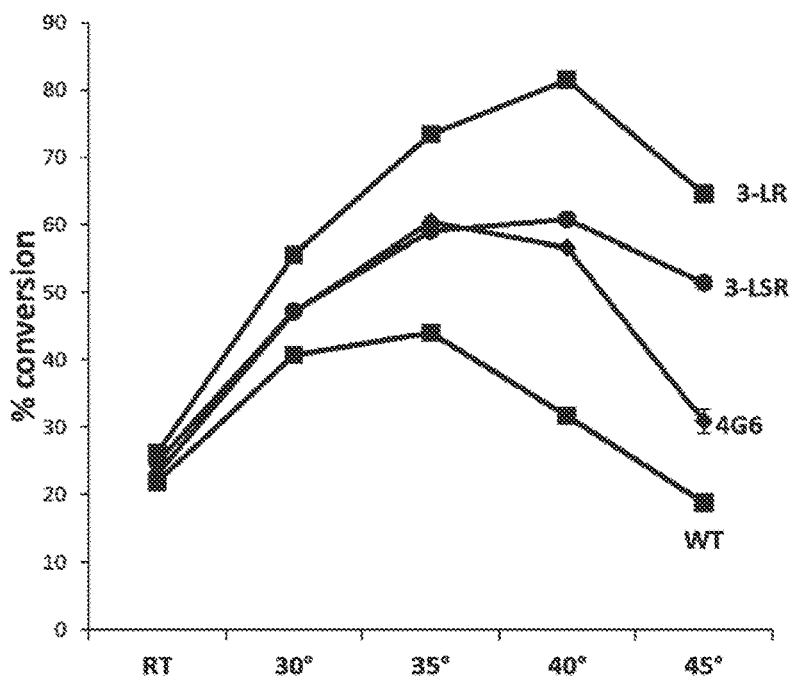
FIG. 3. Activity-temperature profiles of RebH enzymes. To determine if improved thermostability enables reactions at higher temperatures, activity-temperature profiles of RebH variants were constructed. Activity-temperature profiles were constructed using 0.4% purified enzyme with 75 µL reactions in 1.5-mL microcentrifuge tubes. Reactions were run in a buffer of 20 mM HEPES (pH 7.4), 6.7% glycerol, and 100 mM NaCl, with 0.5 mM L-tryptophan, 20 mM DTT, and 100 µM FAD. Reactions were run overnight at temperatures ranging from 21-45° C. and processed the following day. With the accumulation of beneficial mutations, the optimum temperature ($T_{opt}$) increased by at least 5° C., from between 30 and 35° C. for wild-type RebH to 40° C. for 3-LR. Mutant 3-LR was able to produce 100% more 7-chlorotryptophan than wild-type RebH when each acted at their respective $T_{opt}$.

The present embodiments provide compositions for the halogenation of arenes under mild conditions (aqueous solution, pH 6-8). Various features and advantageous details are explained more fully with reference to the non-limiting embodiments that are illustrated in the accompanying drawings and detailed in the following description. It should be understood, however, that the detailed description and the specific examples, while indicating embodiments of the invention, are given by way of illustration only, and not by way of limitation. Various substitutions, modifications, additions, and/or rearrangements will become apparent to those of ordinary skill in the art from this disclosure.

In the following description, numerous specific details are provided to provide a thorough understanding of the disclosed embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Biosynthesis offers an appealing alternative to the harsh chemical conditions required to halogenate aryl groups. RebH is a flavin-dependent halogenase which halogenates arenes by employing halide salts and air as the halogen source and terminal oxidant, respectively.

A new method for selective arene halogenation using the flavin-dependent halogenase RebH employs halide salts and air as the halogen source and terminal oxidant, respectively. Improved expression protocols for RebH and its cognate reductase, RebF, enable halogenation of a range of substituted indoles and naphthalenes. While the scope, selectivity, and mild reaction conditions employed highlight the synthetic utility of enzymatic halogenation, the low catalytic efficiency of RebH (the maximum $k_{cat}$ observed was 1.1 min$^{-1}$ on the native substrate, tryptophan) clearly hinders its practicality.

Over the course of preparative-scale bioconversions, extensive RebH precipitation was observed, which suggests that significant improvements in product yield might be possible by increasing the stability of this enzyme. Improving enzyme thermostability has multiple benefits, including prolonging catalyst lifetime, increasing enzyme tolerance to stresses such as proteolysis or organic solvents, and enabling reactions to be conducted at higher temperatures, which increases reaction rate and overall process efficiency. Stabilized RebH variants offer improved tolerance towards subsequent mutations aimed at altering other properties, such as substrate scope and specific activity, since mutations are generally destabilizing.

Directed evolution was employed to increase the thermostability of RebH without decreasing its activity. Three rounds of error-prone PCR and high-throughput screening combined with the recombination of stabilizing mutations yielded RebH variants with higher melting temperatures and increased optimum temperatures for activity. The crystal structure of the most thermostable mutant was solved and compared with the wild-type RebH structure in an effort to gain insight into the molecular basis for thermostability.

Stability is an important property of all enzymes, particularly those exposed to the harsh reactions conditions encountered in industrial processes or subjected to laboratory evolution experiments. Proteins use a variety of strategies for stabilization, and comparisons of homologous proteins from mesophiles and thermophiles has not yielded a unifying set of rules for thermostabilization. Increasing the number of hydrogen bonds, improving packing, decreasing surface to volume ratio, increasing the stability of α-helices, increasing the number of ionic interactions, and increasing the hydrophobic interactions in the protein core are all examples of mechanisms exploited for improving thermal stability (Petsko, 2001). No single factor seems to dominate, but many small contributions add to create a thermostable protein.

Given the myriad factors and combinations of factors responsible for thermostabilization, predicting beneficial mutations is challenging. Directed evolution based on random mutagenesis was employed to generate a thermostabilized halogenase. The present study improved the thermostability of the tryptophan halogenase RebH, for which there are no known homologues in thermophiles, while also increasing activity at elevated temperatures.

Three rounds of error-prone PCR, recombination, and screening resulted in variant 3-LRS with a $T_m$ 18° C. higher than that of wild type, and variant 3-LR with a $T_{opt}$ over 5° C. higher than wild type. Different mutants had the highest $T_m$ and $T_{opt}$ values, which indicates that thermostability and thermoactivity were not coupled strictly. Without wishing to be bound by theory, one hypothesis that might account for this difference is that increased rigidity helps stability but hinders activity. Examining the crystal structure of the most thermostable mutant, 3-LRS, yielded insights into the possible molecular mechanisms of stabilization. Variant 3-LRS, in comparison to wild-type RebH, modifies the charge distribution on the protein surface by removing a lysine from an already positively charged area and introducing an arginine in the place of a neutral glutamine, and increases the stability of the N-terminus with a Ser-to-Pro mutation.

RebH has been engineered for increased thermostability and activity at elevated temperatures, which addresses immediate concerns regarding catalyst efficiency. This work also establishes a robust protocol for further optimization of RebH.

Variants of RebH obtained using the directed evolution procedure outlined herein could be used to address several significant synthetic challenges, including selective and efficient electrophilic arene halogenation (e.g., X=Br, Cl). Panels of RebH variants with activity on model substrates can be used to rapidly identify active and selective enzymes for a wide range of small molecule substrates, such as drug candidates or natural products. These initial hits can be rapidly optimized using directed evolution, which allows for systematic late-stage halogenation of biologically active molecules to improve the activity of these compounds. Evolved FDH variants can also be used to catalyze non-natural oxidative halogenation reactions, including olefin halogenation, halocyclization, and iodination, that have proven challenging using small molecule catalysts.

EXAMPLES

Materials and Methods

The following examples are included to demonstrate embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Library Construction, Expression, and Screening—All genes encoding RebH were cloned into pET-28a between the NdeI and HindIII digestion sites. Mutant libraries were constructed by error-prone PCR, using Taq polymerase with 150 µM $MnCl_2$ (round 1) or 100 µM $MnCl_2$ (rounds 2 and 3). PCR was performed in a volume of 50 µL with conditions of 95° C. 30 s, (95° C. 30 s, 55° C. 30 s, 72° C. 90 s) for 20 cycles, 72° C. 10 min. Beneficial mutations were recombined via overlap extension (Heckman and Pease, 2007) with PCR conditions of 98° C. 30 s, (98° C. 10 s, 72° C. 50 s) for 35 cycles, 72° C. 10 min. Plasmids were transformed by electroporation into E. coli containing the chaperone pGro7. Library colonies were picked using an automated colony picker (Norgren Systems) and arrayed in 1-ml 96-well plates containing 300 µL LB with 50 µg/mL kanamycin and 20 µg/mL chloramphenicol. Cells were grown overnight at 37° C., 250 rpm, and 50-100 µL of overnight culture was used to inoculate 1 mL TB media (with 50 µg/mL kanamycin and 20 µg/mL chloramphenicol) in 2-mL 96-well plates. Following growth at 37° C., 250 rpm, to an $OD_{600}$=0.9-1, enzyme expression was induced with IPTG and arabinose to final concentrations of 10 µM and 0.2 mg/mL, respectively. Protein expression continued for ~20 h at 30° C., 250 rpm, after which cultures were harvested by centrifugation and stored at −80° C. until use.

Cell pellets were thawed and suspended in 100 µL 25 mM HEPES (pH 7.4) with 0.75 mg/mL lysozyme. After incubation at 37° C., 250 rpm, cells were flash frozen in liquid nitrogen and thawed in a 37° C. water bath. Ten microliters of DNaseI at 1 mg/mL were added and the cells incubated at 37° C., 250 rpm, for 15 min. After centrifugation, 50 µL of supernatant were transferred to a microtiter plate for screening.

Libraries were sealed (AeraSeal, Research Products International), incubated at 42° C. for 2 h (round 1), 51° C. for 2 h (round 2), or 54° C. for 3 h (round 3) and then immediately cooled in an ice water bath. Similar to what has been described previously (Payne, Andorfer and Lewis, 2013), tryptophan halogenation reactions of 75 µL total volume in 25 mM HEPES (pH 7.4) consisted of: 50 µL lysate, 0.5 mM L-tryptophan, 10 mM NaCl, 100 µM NAD, 100 µM FAD, 20 mM glucose, 2.5 µM RebF (reductase), and 50 U/mL glucose dehydrogenase. Reactions were mixed, the plates sealed, and left overnight on the benchtop. Reactions were quenched with an equal volume of methanol and centrifuged, and the supernatant was filtered and analyzed for 7-chlorotryptophan production via HPLC.

Enzyme Purification and Residual Activity Determination—Enzyme expression and purification procedures were adapted from a previous report (Payne, Andorfer and Lewis, 2013). An overnight starter culture was used to inoculate 50 mL TB media (with 50 µg/mL kanamycin and 20 µg/mL chloramphenicol). Following growth at 37° C., 250 rpm, until $OD_{600}$=0.6-0.8, enzyme expression was induced with IPTG and arabinose to final concentrations of 100 µM and 2 mg/mL, respectively. Protein expression continued for ~20 h at 30° C., 250 rpm, after which cultures were harvested by centrifugation and stored at −80° C. until use. Cell pellets were thawed, suspended in 15 mL 20 mM HEPES (pH 7.4), 150 mM NaCl, and lysed by sonication. After clarification by centrifugation, halogenases were purified by Ni-NTA affinity chromatography and exchanged into a buffer of 20 mM HEPES (pH 7.4), 150 mM NaCl, and 10% glycerol. For crystallography, mutant RebH was further purified by gel filtration chromatography using a HiLoad 16/600 Superdex 200 column (GE Healthcare Life Sciences) into a buffer of 20 mM HEPES (pH 7.4). Protein concentration was determined using $A_{280}$ and extinction coefficients calculated based on amino acid composition.

The residual activity was determined following incubation of 50 µL of pure protein at 49° C. for 2 h in 1.5-mL microcentrifuge tubes. Tryptophan halogenation reactions consisted of the same reagents described above with the following exceptions: pure protein was substituted for lysate, and the buffer was 20 mM HEPES (pH 7.4), 6.7% glycerol, and 100 mM NaCl. Reactions were run overnight on the benchtop and processed the following day as above.

$T_m$ and $T_{opt}$ analyses—Melting temperature measurements were conducted in 20 mM HEPES (pH 7.4), 150 mM NaCl, and 10% glycerol, with a protein concentration of 20 µM. Thermal denaturation was irreversible and monitored by circular dichroism spectroscopy using an AVIV 202 CD Spectrometer with Peltier temperature controller. Unfolding was monitored at 222 nm in 2° C. increments from 20-90° C. with 2 min equilibration at each temperature. The midpoint of the denaturation curve was determined with SigmaPlot (Systat Software, San Jose, Calif.) after fitting to a 4-parameter sigmoid.

Activity-temperature profiles were constructed using purified enzyme with 75 µL reactions in 1.5-mL microcentrifuge tubes. Reactions were run in a buffer of 20 mM HEPES (pH 7.4), 6.7% glycerol, and 100 mM NaCl, with 0.5 mM L-tryptophan, 20 mM DTT, and 100 µM FAD. Reactions were run overnight at temperatures ranging from 21-45° C. and processed the following day as above.

Crystallization and structure determination—Purified protein was concentrated to 11 mg/mL, and crystals were grown at 20° C. using the hanging drop vapor diffusion method with a reservoir solution of 1.4 M Na/K phosphate buffer (pH 6.8). Rod-like crystals grew in 2-3 weeks and were flash frozen in liquid nitrogen following cryoprotection with the reservoir solution supplemented with 16% glycerol. Data were collected at NE-CAT beamline 24-ID-E at the Advanced Photon Source at Argonne National Laboratory, and processed using HKL2000 (Otwinowski and Minor, 1997). Phases were determined via molecular replacement using Phaser (McCoy, 2007) and wild-type RebH (PDB ID 2OAM) as the search model. Manual model building was performed in Coot (Emsley and Cowtan, 2004), and the structure was refined with PHENIX (Adams, 2010). Figures were prepared with PyMOL (The PyMOL Molecular Graphics System, Version 1.3, Schrödinger, LLC).

Results

Directed evolution for thermostable RebH mutants—The thermostability of RebH was increased by random mutagenesis and screening followed by recombination of the beneficial mutations. In order to improve thermostability without losing catalytic activity, the screen involved incubating libraries of RebH mutants at elevated temperature and then testing for residual activity. Error-prone PCR was used to generate a library of RebH variants with an average of 2 residue mutations/sequence. The library was expressed in $E.$ $coli$ in 96-well expression plates, the cells lysed, and the supernatant transferred to microtiter plates for heat treatment. Following tryptophan halogenation reactions, residual activity was determined by HPLC analysis.

The first-generation mutant library was constructed using wild-type RebH as the parent, and 1,365 colonies were screened. Mutants with twice the activity of wild type were identified and their improved activities confirmed following purification. The screen emphasizes catalytic activity following heat treatment, therefore the correlation between heat treatment and thermostability was investigated. To test this, the melting temperature of an improved mutant with a single amino acid mutation, S2P, was analyzed by circular dichroism (CD) spectroscopy. The S2P mutant has a $T_m$ 2° C. higher than that of wild-type RebH, indicative of increased stability. The six mutations identified in improved variants from the first round were recombined using overlap extension PCR, and the best variant (designated 1-PVM) from this library contained three mutations: S2P, M71V, and K145M (Table 1, FIG. 1A).

TABLE 1

| Improved Thermostability Variants From First Round | Overlap Extension PCR-Recombined Variants From First Round Variants |
| --- | --- |
| S2P | M71V T213A |
| K145M | S2P D203A |
| D203A | S2P K145M |
| F396Y | S2P F396Y |
| T213A | S2P M71V |
| M71V | S2P T213A |
|  | S2P M71V K145M (1-PVM) |

The 1-PVM mutant was used as the parent for the second-generation random mutagenesis library. Of the 1,008 colonies screened, variant 4G6 was identified as having 2.5-fold the activity of the parent and harbored the additional amino acid mutations E423D and E461G as well as a silent nucleotide mutation. The third-generation random mutagenesis library used 4G6 as the template and contained another 1,008 colonies. The three best-performing variants from the third round of screening each contained single amino acid mutations. Following recombination, the two best variants were identified as 3-LR and 3-LSR, which possess the additional mutations S130L and Q494R (3-RL) and S130L, N166S, and Q494R (3-LSR) (Table 2, FIG. 1B).

TABLE 2

| Improved Thermostability Variants From Second Round | Improved Thermostability Variants From Third Round |
| --- | --- |
| S2P M71V K145M T394M | S2P M71V K145M E423D E461G T413A Q494R |
| S2P M71V K145M E423D E461G (4-G6) | S2P M71V K145M E423D E461G Q494R |
| S2P M71V K145M D264G | S2P M71V K145M E423D E461G K237E |
|  | S2P M71V K145M E423D E461G S130L |
|  | S2P M71V K145M E423D E461G T496R |
|  | S2P M71V K145M E423D E461G G504S |
|  | S2P M71V K145M E461G T258A L289P |
|  | S2P M71V K145M E423D E461G N166S |
|  | S2P M71V K145M E423D E461G Q494R S130L N166S (3-LR) |
|  | S2P M71V K145M E423D E461G Q494R N166S |
|  | S2P M71V K145M E423D E461G Q494R S130L N166S (3-LSR) |
|  | S2P M71V K145M E423D E461G S130L N166S |

Characterization of evolved RebH mutants—The melting temperatures of the best mutants identified throughout the rounds of genetic diversification, screening, and recombination were analyzed to probe the relationship between residual activity and thermostability (FIG. 2). Wild-type RebH has a melting temperature of 52.4° C., and that of the most thermostable variant, 3-LSR, is 70.0° C. The 18° C. increase in $T_m$ indicates significant improvement in enzyme stability and is approximately equal to the difference between enzymes of mesophiles and those of thermophiles.

TABLE 3

Melting Temperatures (° C.) of WT RebH and Best Variants

| wt | 52.4 |
| --- | --- |
| S2P M71V K145M E423D E461G (4-G6) | 59.9 |
| S2P M71V K145M E423D E461G Q494R S130L (3-LR) | 65.6 |
| S2P M71V K145M E423D E461G S130L N166S | 67.8 |
| S2P M71V K145M E423D E461G Q494R S130L N166S (3-LSR) | 70 |

To determine if improved thermostability enables reactions at higher temperatures, activity-temperature profiles of RebH variants were constructed (FIG. 3). With the accumulation of beneficial mutations, the optimum temperature ($T_{opt}$) increased by at least 5° C., from between 30 and 35° C. for wild-type RebH to 40° C. for 3-LR. Mutant 3-LR was able to produce 100% more 7-chlorotryptophan than wild-type RebH when each acted at their respective $T_{opt}$.

RebH has been shown to halogenate a variety of non-native substrates (Payne, Andorfer and Lewis, 2013; Vaillancourt, et al., 2006; Blasiak and Drennan, 2009; Butler and Sandy, 2009; Anderson and Chapman, 2006). The ability of thermostable variants to halogenate the native substrate L-tryptophan as well as non-native substrates tryptamine and tryptoline was investigated. Several variants displayed chlorinating activity towards L-tryptophan non-native substrates tryptamine and tryptoline (Tables 4 and 5). Through methods analogous to the directed evolution of RebH for increased thermostability, further mutations were added to mutant 1-PVM (S2P M71V K145M) to increase activity on L-tryptophan, tryptoline, and desbromodeformylflustrabromine. Variants were also tested for their ability to chlorinate tryptoline at different catalyst loads (FIGS. 5A-5E).

TABLE 4

Ability of WT RebH and Variants to Chlorinate Native and Non-Native Substrates (% conversion)

|  | L-tryptophan (0.2% load) | 2-methyl tryptamine (1% load) | tryptoline (4.7% load) |
|---|---|---|---|
| wt | 27 | 39 | 15 |
| S2P | 40 | 63 | 62 |
| S2P M71V K145M | 42 | 59 | 50 |
| S2P M71V K145M N467T | 69 | 63 | 90 |
| S2P M71V K145M F458S | 39 | 24 | 9 |
| S2P M71V K145M T394M | 57 | 60 | 51 |
| S2P M71V K145M E423D E461G | 29 | 9 | 6 |
| S2P M71V K145M T348A L453P A476T | 27 | 41 | 41 |
| S2P M71V K145M D264G | 46 | 62 | 30 |
| S2P F465C | 15 | 63 | 30 |

TABLE 5

Ability of WT RebH and Variants to Halogenate Native and Non-Native Substrates (% conversion)

|  | L-tryptophan (0.2% load) | tryptoline (4.7% load) |
|---|---|---|
| wt | 39 | 8 |
| S2P M71V K145M | 57 | 22 |
| S2P M71V K145M N467T | 99 | 44 |
| S2P M71V K145M N467T L380F | 79 | 40 |
| S2P M71V K145M N467T D101G K237E | 60 | 37 |
| S2P M71V K145M N467T N470S | 41 | 98 |
| S2P M71V K145M N467T F171I T283A | 94 | 33 |
| S2P M71V K145M N467T L114P | 31 | 42 |
| S2P M71V K145M N467T G112S | 50 | 76 |
| S2P M71V K145M N467T V256I | 83 | 45 |

TABLE 6

Ability of WT RebH and Variants to Halogenate Native and Non-Native Substrates (% conversion)

|  | L-tryptophan (0.2% load) | Tryptoline (0.5% load) | Debromo-desformyl-flustrabromine (5% load) | Evodiamine (5% load) |
|---|---|---|---|---|
| wt | 53 | 3 | 0 | 2 |
| S2P M71V K145M (1-PVM) | 43 | 6 | 0 | 9 |
| S2P M71V K145M N467T (2-T) | 53 | 8 | 0 | 8 |
| S2P M71V K145M N467T G112S N470S (3-SS) | 22 | 64 | 6 | 26 |
| S2P M71V K145M N467T N470S | 48 | 50 | 29 | 27 |
| S2P M71V K145M N467T N470S A442V (4-V) | 42 | 43 | 48 | 28 |
| S2P M71V K145M N467T N470S D203G | — | — | 38 | — |

Table 6 presents data obtained from a second set of the activity experiments described in Table 5, in which the activities of the mutants were tested against L-tryptophan, Tryptoline, Debromo-desformyl-flustrabromine, and Evodiamine.

Some of the mutants described above were able to chlorinate a broad range of substrates. These substrates are illustrated in FIG. 8.

Potentially key mutations: FIG. 8 indicates that mutant 4-V accepts a wide range of very large substrates, including carvedilol and yohimbine. Mutation A442V appears to be broadly useful for large substrates, especially those with MW>>200 g/mol (the approximate MW of L-tryptophan). The top four substrates shown in FIG. 8, all of which have tricyclic tryptoline-like structures, were chlorinated best by mutant 3-SS. For these substrates, the G112S and N470S mutations appeared to be especially important. The high activities obtained with mutant 4-V applied to large substrates worked well with the removal of the G112S mutation, suggesting that this mutation can be detrimental to high activity on large substrates.

Figure 8:
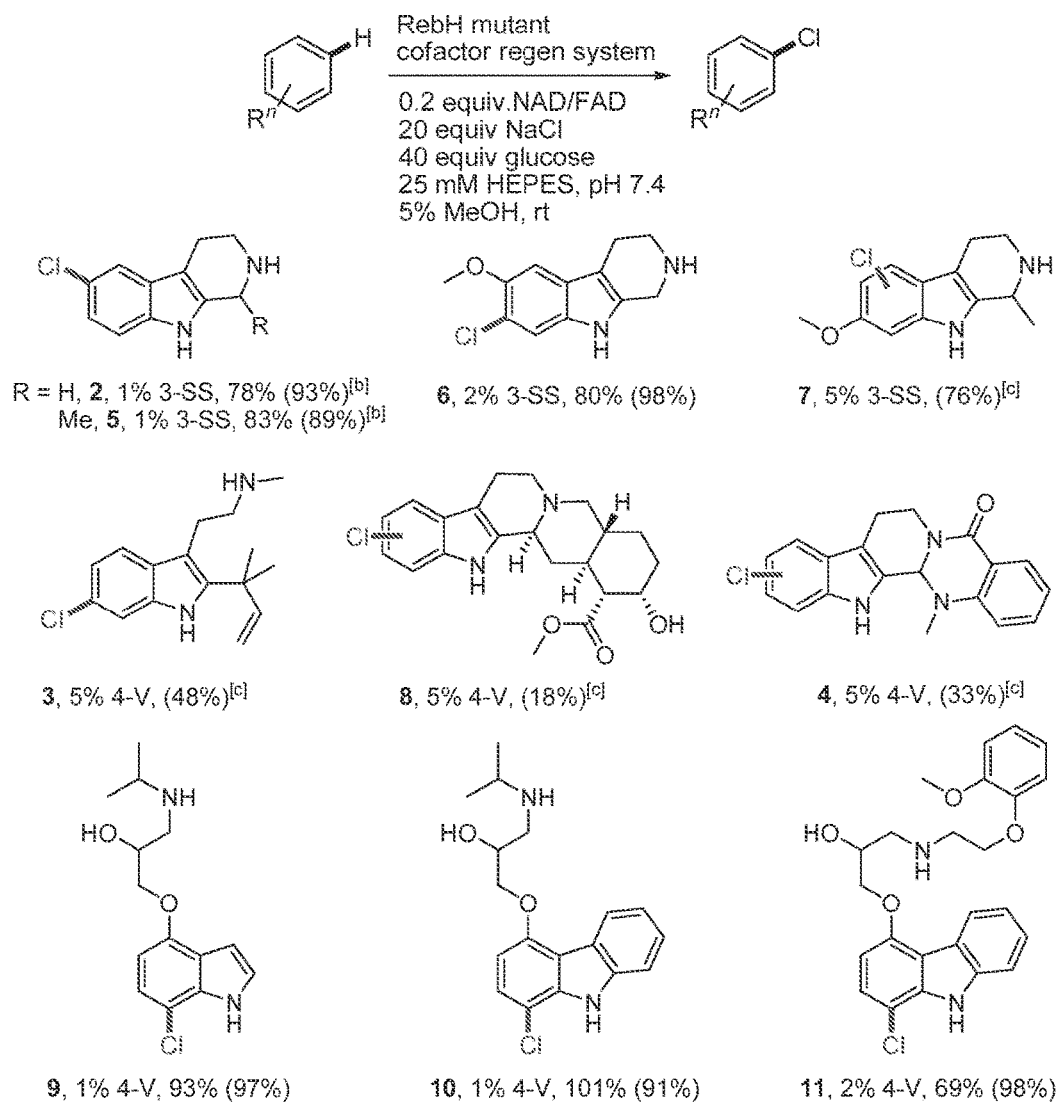
FIG. 8. General reaction scheme for preparative RebH mutant-catalyzed halogenation reactions and synthesized compounds. Cofactor regen system consisted of 0.5 mol % MBP-RebF and 50 U mL-1 glucose dehydrogenase. [a] Yields of isolated products and HPLC conversions are provided in parentheses. [b] In addition to the major product shown, approximately 10% of the 6-chlorinated compound was observed as well. [c] Only HPLC conversions are shown. Chlorination substrates include: 2=tryptoline, 5=eleagnine, 6=pinoline, 7=tetrahydroharmine, 3=debromodesformylflustrabromine, 8=yohimbine, 4=evodiamine, 9=pindolol, 10=carazolol, and 11=carvedilol.

The activities of mutants 4-V and 3-SS were compared to the activity of the wild-type RebH for each substrate shown in FIG. 8. These ratios are listed in Table 7:

TABLE 7

| Substrate | Mutant | Mol % Enzyme | Activity Ratio[a] |
|---|---|---|---|
| Tryptoline (2) | 3-SS | 0.5 | 65.5 |
| Eleagnine (5) | 3-SS | 0.5 | 67.1 |
| Pinoline (6) | 3-SS | 0.5 | 2.0 |
| Tetrahydroharmine (7) | 3-SS | 5 | 17.6 |
| Debromo-dFBr (3) | 4-V | 5 | N/A[b] |
| Yohimbine (8) | 4-V | 5 | N/A[b] |
| Evodiamine (4) | 4-V | 5 | 16.5 |
| Pindolol (9) | 4-V | 0.2 | 1.3 |
| Carazolol (10) | 4-V | 0.2 | 4.9 |
| Carvedilol (11) | 4-V | 0.5 | 8.2 |

Table 1
[a]Activity ratio is ratio of conversion seen with mutant tested vs. WT. Reaction conditions were those shown in Scheme 2.
[b]WT showed no detectable activity, and thus a ratio cannot be determined.

Solvent tolerance—Solvent tolerance analyses were run under the same conditions as the characterization of evolved RebH mutants, with the exception that 30% DMSO was added as a co-solvent (Table 8).

TABLE 8

Solvent Tolerance, 30% DMSO as co-solvent, 1% load (% conversion)

| wt | 27 |
|---|---|
| N75K | 17 |
| E96V | 19 |
| F312L | 16 |
| S2P | 28 |
| S2P, M71V | 67 |
| S2P, T213A | 29 |
| S2P, K145M | 33 |

TABLE 8-continued

Solvent Tolerance, 30% DMSO as
co-solvent, 1% load (% conversion)

| | |
|---|---|
| S2P, D203A | 48 |
| S2P, F396Y | 44 |
| F396Y | 7 |
| M71V | 33 |
| M71T | 23 |
| M71A | 65 |
| M71C | 35 |
| M71V, T213A | 20 |

Crystal structure of thermostable 3-LSR—The crystal structure of 3-LSR (PDB ID 4LU6) was solved by molecular replacement using wild-type RebH (PDB ID 2OAM) as the search model. The model was refined to 3.05 Å with a final $R_{work}$=18% and $R_{free}$=24%. Wild-type RebH and 3-LSR are similar overall with a backbone root mean square deviation (rmsd) of 0.32 Å. The differences in the structures are localized in the eight amino acid changes between the two enzymes.

Figure 4:
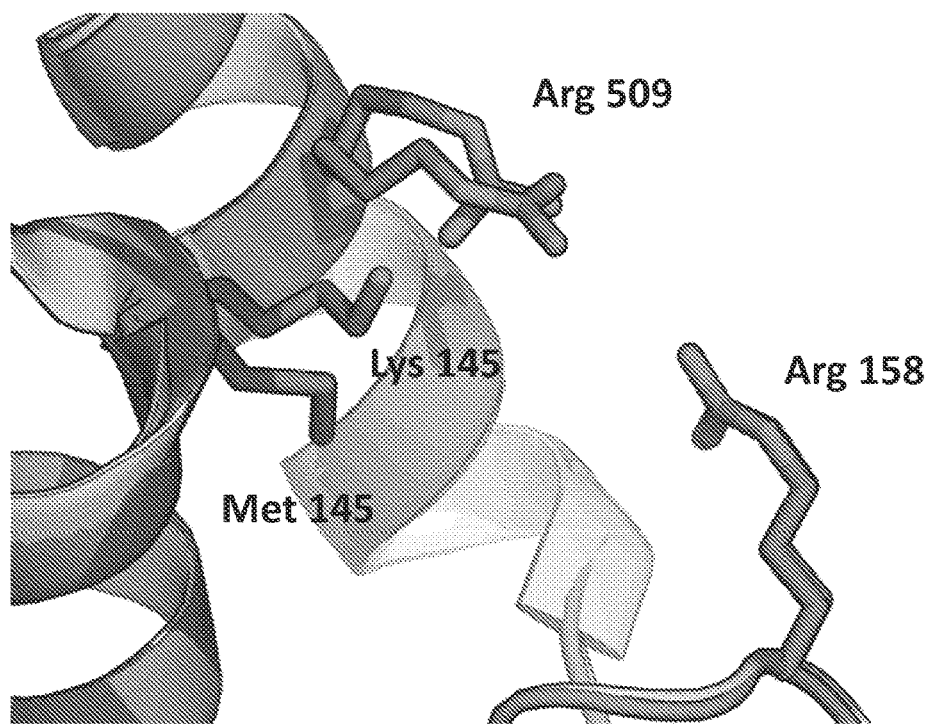
FIG. 4. Local environment of the K145M mutation. Overlay of wild-type RebH (grey backbone and cyan side-chain carbon atoms and blue side-chain nitrogen atoms) and 3-LSR (light blue backbone and yellow side-chain carbon atoms, blue nitrogen atoms, and green sulfur atom). Mutation K145M is located near the surface of the protein and in the area of two arginine residues. Without wishing to be bound by theory, it is thought that wild-type RebH increases the density of positive charge in the area with lysine, and 3-LSR might be stabilized by reducing this density by substituting a methionine at this position and the side chain of methionine adopts a conformation that increases its packing with neighboring residues, which might enhance thermostability.

Investigating the location and nature of the mutations in the structure of 3-LSR may provide a molecular basis for the increase in thermostability and $T_{opt}$. Mutation Q494R is located on the protein surface and converts the neutral side chain of glutamine into the positively charged side chain of arginine. Increasing the amount of surface charge is a deterrent to protein aggregation. The serine-to-proline mutation of S2P is located right at the N-terminus, and proline residues generally increase protein rigidity by decreasing the flexibility of the polypeptide chain. Indeed, the five other RebH structures in the PDB start their models at amino acid number two or three; in 3-LSR, the electron density map extends to amino acid number one, indicating increased order at the N-terminus. The increased rigidity of the N-terminus might also help stabilize the protein by preventing it from acting as a fraying point for thermal denaturation. Mutation K145M is located near the surface of the protein and in the area of two arginine residues (FIG. 4). Wild-type RebH increases the density of positive charge in the area with lysine, and 3-LSR might be stabilized by reducing this density by substituting a methionine at this position. Also, the side chain of methionine adopts a conformation that increases its packing with neighboring residues, which might enhance thermostability.

Changing the regioselectivity of RebH through directed evolution—Through methods analogs to the directed evolution of RebH for increased thermostability, the regioselectivity of RebH has been altered on the unnatural substrate tryptamine (ratio of 7-6-5 selectivity, Table 10). This is important in broadening the scope of RebH to chlorination of C—H bonds within a molecule beyond its natural regioselectivity, and can be applied to changing the regioselectivity on other substrates in the future. The first variant for this evolution was RebH-N470S.

TABLE 9

| Variant with Increased Activity on Tryptamine | |
|---|---|
| N470S | |
| Variant with Altered Selectivity on Tryptamine - Rd 1 | |
| N470S, S448P | |
| Variants with Increased Activity on Tryptamine - Rd 2 | Overlap Extension PCR-Recombined Variant From Second Round Variants |
| N470S, S448P, L380F, Q494R<br>N470S, S448P, R509Q | N470S, S448P, L380F, Q494R, R509Q |
| Variant with Altered Selectivity on Tryptamine - Rational point mutation | |
| N470S, S448P, L380F, Q494R, R509Q, Y455W | |
| Variant with Increased Activity on Tryptamine - Rd 3 | |
| N470S, S448P, L380F, Q494R, R509Q, Y455W, S110P | |
| Variant with Altered Selectivity on Tryptamine - Rd 3 | Overlap Extension PCR-Recombined Variant From Third Round Variants |
| N470S, S448P, L380F, Q494R, R509Q, Y455W, F111L | N470S, S448P, L380F, Q494R, R509Q, Y455W, S110P, F111L |
| Variants with Increased Actvity on Tryptamine - thermostability mutation additions | Overlap Extension PCR-Recombined Variants From Thermostability Mutants |
| N470S, S448P, L380F, Q494R, R509Q, Y455W, S110P, F111L, S130L<br>N470S, S448P, L380F, Q494R, R509Q, Y455W, S110P, F111L, N166S | N470S, S448P, L380F, Q494R, R509Q, Y455W, S110P, F111L, S130L, N166S |

TABLE 9-continued

| Variants with Altered Selectivity on Tryptamine - Rd 4 | Overlap Extension PCR-Recombined Variants From Fourth Round Variants |
|---|---|
| N470S, S448P, L380F, Q494R, R509Q, Y455W, S110P, F111L, S130L, N166S, T322I, F458L, F465L, V481A | N470S, S448P, L380F, Q494R, R509Q, Y455W, S110P, F111L, S130L, N166S, F465L |
| N470S, S448P, L380F, Q494R, R509Q, Y455W, S110P, F111L, S130L, N166S, I52T, T496A | N470S, S448P, L380F, Q494R, R509Q, Y455W, S110P, F111L→L111S, S130L, N166S |
| N470S, S448P, L380F, Q494R, R509Q, Y455W, S110P, F111L→L111S, S130L, N166S, A58V | N470S, S448P, L380F, Q494R, R509Q, Y455W, S110P, F111L→L111S, S130L, N166S, F465L |
| | N470S, S448P, L380F, Q494R, R509Q, Y455W, S110P, F111L, S130L, N166S, F465L, I52T |
| | N470S, S448P, L380F, Q494R, R509Q, Y455W, S110P, F111L→L111S, S130L, N166S, I52T |
| | N470S, S448P, L380F, Q494R, R509Q, Y455W, S110P, F111L→L111S, S130L, N166S, F465L, I52T |

| Variants with Altered Selectivity on Tryptamine - NDT library | |
|---|---|
| N470S, S448P, L380F, Q494R, R509Q, Y455W, S110P, F111L→L111S, S130L, N166S, G112D, L113N | |
| N470S, S448P, L380F, Q494R, R509Q, Y455W, S110P, F111L→L111S, S130L, N166S, G112D, L113D | |

| Variants with Altered Selectivity on Trytpamine - Rd 5 | Overlap Extension PCR-Recombined Variant From Fifth Round Variants |
|---|---|
| N470S, S448P, L380F, Q494R, R509Q, Y455W, S110P→P110L, F111L, S130L, N166S, F465L, I52T | N470S, S448P, L380F, Q494R, R509Q, Y455W, S110P→P110L, F111L, S130L, N166S, F465L, I52T, K145R, A476V |
| N470S, S448P, L380F, Q494R, R509Q, Y455W, S110P, F111L, S130L, N166S, F465L, I52T, K145R, A476V | N470S, S448P, L380F, Q494R, R509Q, Y455W, S110P→P110L, F111L, S130L, N166S, F465L, I52T, K187R, F396L |
| N470S, S448P, L380F, Q494R, R509Q, Y455W, S110P, F111L, S130L, N166S, F465L, I52T, K187R, F396L | |

S110P→P110L and F111L→L111S denote secondary mutations, which means the S110P and/or F111L mutations from one round were further mutated to give the respective P110L and L111S mutations. The effective mutations from WT are S110L and F111S.

TABLE 10

| Best Actvity and Selectivity Variants | % Loading of RebH relative to tryptamine | % Conversion | Ratio of 7-6-5 selectivity |
|---|---|---|---|
| N470S | 1.67 | 86 | 99-1-0 |
| N470S, S448P | 1.67 | 55 | 94-4-2 |
| N470S, S448P, L380F, Q494R, R509Q | 1.67 | 91 | 94-4-2 |
| N470S, S448P, L380F, Q494R, R509Q, Y455W | 1.67 | 76 | 91-6-3 |
| N470S, S448P, L380F, Q494R, R509Q, Y455W, S110P, F111L | 1.67 | 50 | 85-10-5 |
| N470S, S448P, L380F, Q494R, R509Q, Y455W, S110P, F111L, S130L, N166S | 1.67 | 68 | 85-10-5 |
| N470S, S448P, L380F, Q494R, R509Q, Y455W, S110P, F111L→L111S, S130L, N166S | 1.67 | 24 | 25-75-0 |
| N470S, S448P, L380F, Q494R, R509Q, Y455W, S110P, F111L, S130L, N166S, F465L, I52T | 5 | 33 | 34-35-31 |
| N470S, S448P, L380F, Q494R, R509Q, Y455W, S110P, F111L→L111S, S130L, N166S, G112D, L113N | 1.67 | 51 | 18-82-0 |
| N470S, S448P, L380F, Q494R, R509Q, Y455W, S110P→P110L, F111L, S130L, N166S, F465L, I52T | 5 | 29 | 25-36-39 |

S110P→P110L and F111L→L111S denote secondary mutations. The S110P and/or F111L mutations from one round were further mutated to give the respective P110L and/or L111S mutations. The effective mutations from WT RebH are S110L and F111S.

REFERENCES

Adams, P. D., Afonine, P. V., Bunkóczi, G., Chen, V. B., Davis, I. W., Echols, N., Headd, J. J., Hung, L. W., Kapral, G. J., Grosse-Kunstleve, R. W., McCoy, A. J., Moriarty, N. W., Oeffher, R., Read, R. J., Richardson, D. C., Richardson, J. S., Terwilliger, T. C., and Zwart, P. H. (2010) *Acta Crystallographica, D*66, 213-221.

Anderson, J. L. R., Chapman, S. K. (2006) *Molecular Biosystems*, 2, 350-357.
Blasiak, L. C. and Drennan, C. L., (2009) *Accounts of Chemical Research*, 42, 147-155.
Butler, A. and Sandy, M. (2009) *Nature*, 460, 848-854.
Emsley, P. and Cowtan, K. (2004) *Acta Crystallographica*, D60, 2126-2132.
Heckman, K. L. and Pease, L. R. (2007) *Nature Protocols*, 2, 924-932.
McCoy, A. J., Grosse-Kunstleve, R. W., Adams, P. D., Winn, M. D., Storoni L. C., and Read. R. J. J. (2007) *Applied Crystallography*, 40, 658-674.
Otwinowski, Z. and Minor, W. (1997) *Methods in Enzymology*, 276, 307-326.
Payne, J. T., Andorfer, M. C. and Lewis, J. C. (2013) *Angewandte Chemie International Edition*, 125, 5379-5382.
Petsko, G. A. (2001) *Methods in Enzymology*, 334, 469-478
Vaillancourt, F. H., Yeh, E., Vosburg, D. A., Garneau-Tsodikova, S. and Walsh, C. T. (2006) *Chemical Reviews*, 106, 3364-3378.

---

The invention claimed is:

1. An isolated RebH variant polypeptide of SEQ ID NO: 1 comprising at least one amino acid substitution, wherein the at least one amino acid substitution results in improved halogenating activity; and wherein the at least one amino acid substitution is selected from the group consisting of S2P, I52T, A58V, M71V, M71T, M71A, M71C, N75K, E96V, D101G, S110P, S110L, F111S, G112S, G112D, L113D, L113N, L114P, S130L, K145M, K145R, N166S, F171I, K187R, D203A, D203G, T213A, V225I, K237E, V256I, T258A, D264G, T283A, L289P, F312L, T322I, T348A, L380F, T394M, F396Y, F396L, R400C, T413A, E423D, A442V, S448P, L453P, F458S, F458L, E461G, F465C, F465L, N467T, N470S, A476T, A476V, V481A, Q494R, T496R, T496A, G504S, and R509Q, wherein the RebH variant polypeptide is at least 85% identical to SEQ ID NO:1.

2. The RebH variant of claim 1 comprising the amino acid substitutions S2P, M71V, K145M, N467T, N470S, and G112S.

3. The RebH variant polypeptide of claim 1, wherein the polypeptide halogenates an aromatic substrate.

4. The RebH variant polypeptide of claim 1, wherein the polypeptide halogenates a substrate regioselectively.

5. The RebH variant polypeptide of claim 1, wherein the polypeptide displays improved thermostability over wild-type RebH.

6. The RebH variant polypeptide of claim 1, wherein the polypeptide displays increased halogenating activity at an elevated temperature.

7. The RebH variant polypeptide of claim 1, wherein the polypeptide halogenates the wild-type RebH native substrate tryptophan.

8. The RebH variant polypeptide of claim 1, wherein the polypeptide halogenates non-native substrates.

9. The RebH variant polypeptide of claim 1, wherein the polypeptide halogenates a substrate and wherein the substrate comprises a molecule selected from the group consisting of indole, tryptoline, 2-methyltryptamine, eleagnine, pinoline, tetrahydroharmine, debromodesformylflustrabromine, yohimbine, evodiamine, pindolol, carazolol, and carvedilol.

10. The RebH variant polypeptide of claim 1, wherein the polypeptide halogenates using a halogen selected from the group consisting of fluoride, chloride, bromide and iodide.

11. The RebH variant polypeptide of claim 1, wherein the polypeptide displays a prolonged catalyst lifetime.

12. The RebH variant polypeptide of claim 1, wherein the polypeptide displays an increased tolerance to proteolysis.

13. The RebH variant polypeptide of claim 1, wherein the polypeptide displays an increased tolerance to organic solvents.

14. The RebH variant polypeptide of claim 1, wherein the RebH variant polypeptide halogenates in the absence of a harsh chemical oxidant.

15. A RebH variant polypeptide comprising at least one amino acid substitution at position 2, 52, 58, 71, 75, 96, 101, 110, 111, 112, 113, 114, 130, 145, 166, 171, 187, 203, 213, 225, 237, 256, 258, 264, 283, 289, 312, 322, 348, 380, 394, 396, 400, 413, 423, 448, 453, 455, 458, 461, 465, 467, 470, 476, 481, 494, 496, 504 and/or 509 in SEQ ID NO:1, wherein the RebH variant polypeptide is at least 85% identical to SEQ ID NO:1.

16. The isolated RebH variant polypeptide of claim 1, wherein the variant comprises at least a S2P substitution.

* * * * *

SEQUENCE LISTING

<160> NUMBER OF SEQ ID NOS: 2

<210> SEQ ID NO 1
<211> LENGTH: 530
<212> TYPE: PRT
<213> ORGANISM: Lechevalieria aerocolonigenes

<400> SEQUENCE: 1

```
Met Ser Gly Lys Ile Asp Lys Ile Leu Ile Val Gly Gly Gly Thr Ala
1               5                   10                  15

Gly Trp Met Ala Ala Ser Tyr Leu Gly Lys Ala Leu Gln Gly Thr Ala
            20                  25                  30

Asp Ile Thr Leu Leu Gln Ala Pro Asp Ile Pro Thr Leu Gly Val Gly
        35                  40                  45

Glu Ala Thr Ile Pro Asn Leu Gln Thr Ala Phe Phe Asp Phe Leu Gly
    50                  55                  60

Ile Pro Glu Asp Glu Trp Met Arg Glu Cys Asn Ala Ser Tyr Lys Val
65                  70                  75                  80

Ala Ile Lys Phe Ile Asn Trp Arg Thr Ala Gly Glu Gly Thr Ser Glu
                85                  90                  95

Ala Arg Glu Leu Asp Gly Gly Pro Asp His Phe Tyr His Ser Phe Gly
            100                 105                 110

Leu Leu Lys Tyr His Glu Gln Ile Pro Leu Ser His Tyr Trp Phe Asp
        115                 120                 125

Arg Ser Tyr Arg Gly Lys Thr Val Glu Pro Phe Asp Tyr Ala Cys Tyr
    130                 135                 140

Lys Glu Pro Val Ile Leu Asp Ala Asn Arg Ser Pro Arg Arg Leu Asp
145                 150                 155                 160

Gly Ser Lys Val Thr Asn Tyr Ala Trp His Phe Asp Ala His Leu Val
                165                 170                 175

Ala Asp Phe Leu Arg Arg Phe Ala Thr Glu Lys Leu Gly Val Arg His
            180                 185                 190

Val Glu Asp Arg Val Glu His Val Gln Arg Asp Ala Asn Gly Asn Ile
        195                 200                 205

Glu Ser Val Arg Thr Ala Thr Gly Arg Val Phe Asp Ala Asp Leu Phe
    210                 215                 220

Val Asp Cys Ser Gly Phe Arg Gly Leu Leu Ile Asn Lys Ala Met Glu
225                 230                 235                 240

Glu Pro Phe Leu Asp Met Ser Asp His Leu Leu Asn Asp Ser Ala Val
                245                 250                 255

Ala Thr Gln Val Pro His Asp Asp Ala Asn Gly Val Glu Pro Phe
            260                 265                 270

Thr Ser Ala Ile Ala Met Lys Ser Gly Trp Thr Trp Lys Ile Pro Met
        275                 280                 285
```

| | | | | | | | | | | | |
|---|---|---|---|---|---|---|---|---|---|---|---|
|Leu|Gly|Arg|Phe|Gly|Thr|Gly|Tyr|Val|Tyr|Ser|Ser|Arg|Phe|Ala|Thr|
| |290| | | | |295| | | |300| |

Leu Gly Arg Phe Gly Thr Gly Tyr Val Tyr Ser Ser Arg Phe Ala Thr
    290                 295                 300

Glu Asp Glu Ala Val Arg Glu Phe Cys Glu Met Trp His Leu Asp Pro
305                 310                 315                 320

Glu Thr Gln Pro Leu Asn Arg Ile Arg Phe Arg Val Gly Arg Asn Arg
                325                 330                 335

Arg Ala Trp Val Gly Asn Cys Val Ser Ile Gly Thr Ser Ser Cys Phe
            340                 345                 350

Val Glu Pro Leu Glu Ser Thr Gly Ile Tyr Phe Val Tyr Ala Ala Leu
        355                 360                 365

Tyr Gln Leu Val Lys His Phe Pro Asp Lys Ser Leu Asn Pro Val Leu
    370                 375                 380

Thr Ala Arg Phe Asn Arg Glu Ile Glu Thr Met Phe Asp Asp Thr Arg
385                 390                 395                 400

Asp Phe Ile Gln Ala His Phe Tyr Phe Ser Pro Arg Thr Asp Thr Pro
                405                 410                 415

Phe Trp Arg Ala Asn Lys Glu Leu Arg Leu Ala Asp Gly Met Gln Glu
            420                 425                 430

Lys Ile Asp Met Tyr Arg Ala Gly Met Ala Ile Asn Ala Pro Ala Ser
        435                 440                 445

Asp Asp Ala Gln Leu Tyr Tyr Gly Asn Phe Glu Glu Phe Arg Asn
450                 455                 460

Phe Trp Asn Asn Ser Asn Tyr Tyr Cys Val Leu Ala Gly Leu Gly Leu
465                 470                 475                 480

Val Pro Asp Ala Pro Ser Pro Arg Leu Ala His Met Pro Gln Ala Thr
                485                 490                 495

Glu Ser Val Asp Glu Val Phe Gly Ala Val Lys Asp Arg Gln Arg Asn
            500                 505                 510

Leu Leu Glu Thr Leu Pro Ser Leu His Glu Phe Leu Arg Gln Gln His
        515                 520                 525

Gly Arg
    530

<210> SEQ ID NO 2
<211> LENGTH: 1593
<212> TYPE: DNA
<213> ORGANISM: Lechevalieria aerocolonigenes

<400> SEQUENCE: 2

```
atgtccggca agattgacaa gatcctcatc gtcggcggcg gcaccgccgg atggatggcc      60
gcgtcctatc tcggcaaggc cctgcagggc accgcggaca tcacactgct gcaggcaccc     120
gacatcccga cgctcggggt cggcgaggcc acgatcccca atctgcagac ggcgttcttc     180
gacttcctcg gaatccccga ggacgagtgg atgcgggagt gcaacgcgag ctacaaggtc     240
gccatcaagt tcatcaactg cgcaccgcg ggcgagggga cgtccgaggc ccgcgagctc     300
gacggagggc ccgaccactt ctaccactcc ttcggtctgc tcaagtacca cgagcagatt     360
ccgctgtcgc actactggtt cgaccgttcg taccggggga agaccgtcga ccgttcgac     420 tacgcctgct acaaggaacc cgtcatcctc gacgccaaca ggtcaccgcg caggctcgac     480
ggttccaagg tgacgaacta cgcgtggcac ttcgacgcgc acctcgtcgc cgacttcctg     540
cgccggttcg ccaccgagaa gctcggcgtg cgccacgtcg aggaccgcgt cgagcacgtc     600
cagcgcgacg ccaacggcaa catcgagtcg gttcgcacgg caacggggcg tgtcttcgat     660
gccgacctct tcgtcgactg ctcgggcttc cgcgggctgc tgatcaacaa ggcgatggag     720
```

```
gagcccttcc tcgacatgag cgatcacctg ctcaacgaca gcgccgtcgc cacccaggtg    780
ccgcacgacg acgacgcgaa cggtgtggaa ccgttcacct cggcgatcgc catgaagtcg    840
ggctggacgt ggaagatccc gatgctcggc aggttcggca ccgggtacgt ctactcgagc    900
cggttcgcca ccgaggacga ggcggtgcgc gagttctgcg agatgtggca cctcgacccg    960
gagacccagc ccctcaacag gatccggttc cgggtcggcc gcaaccggcg cgcgtgggtc   1020
ggcaactgcg tcagcatcgg cacgtcgtcg tgcttcgtgg aaccactgga gtcgacgggc   1080
atctacttcg tctacgccgc gctgtaccag ctggtgaagc acttccccga caagagcctc   1140
aaccccgtgc tgaccgccag gttcaaccgc gagatcgaga cgatgttcga cgacacgcgc   1200
gacttcatcc aggcgcactt ctacttctcg ccgcgcacgg acacccgtt  ctggagggcc   1260 aacaaggagc tgcgcctggc ggacggcatg caggagaaga tcgacatgta ccgcgcgggc   1320
atggcgatca acgcgcccgc gtccgacgac gcccagctct actacggcaa cttcgaggag   1380
gagttccgca acttctggaa caacagcaac tactactgcg tgctggccgg cctcggtctg   1440
gtgcccgacg caccctcacc acgcctggcg cacatgccac aggcgacgga gtcggtggac   1500
gaggtcttcg gcgccgtcaa ggaccggcag cggaacctgc tcgagaccct gccgagcctc   1560
cacgagttcc tgaggcaaca gcacggccgc tga                               1593
```